(12) United States Patent
Scharenberg et al.

(10) Patent No.: US 12,215,337 B2
(45) Date of Patent: Feb. 4, 2025

(54) VIRAL VECTORS AND PACKAGING CELL LINES

(71) Applicant: Umoja Biopharma, Inc., Seattle, WA (US)

(72) Inventors: Andrew Scharenberg, Seattle, WA (US); Laurie Beitz, Seattle, WA (US)

(73) Assignee: Umoja Biopharma, Inc., Seattle, WA (US)

( * ) Notice: Subject to any disclaimer, the term of this patent is extended or adjusted under 35 U.S.C. 154(b) by 1150 days.

(21) Appl. No.: 17/046,701

(22) PCT Filed: Apr. 11, 2019

(86) PCT No.: PCT/US2019/026923
§ 371 (c)(1),
(2) Date: Oct. 9, 2020

(87) PCT Pub. No.: WO2019/200056
PCT Pub. Date: Oct. 17, 2019

(65) Prior Publication Data
US 2021/0147871 A1 May 20, 2021

Related U.S. Application Data

(60) Provisional application No. 62/656,823, filed on Apr. 12, 2018.

(51) Int. Cl.
| | | |
|---|---|---|
| *C12N 15/86* | (2006.01) |
| *A61K 9/00* | (2006.01) |
| *A61K 31/436* | (2006.01) |
| *A61K 38/13* | (2006.01) |
| *A61K 38/17* | (2006.01) |
| *A61K 39/395* | (2006.01) |
| *C07K 14/55* | (2006.01) |
| *C07K 14/705* | (2006.01) |
| *C07K 16/28* | (2006.01) |

(52) U.S. Cl.
CPC .......... *C12N 15/86* (2013.01); *A61K 9/0019* (2013.01); *A61K 9/0053* (2013.01); *A61K 31/436* (2013.01); *A61K 38/13* (2013.01); *A61K 38/177* (2013.01); *A61K 38/1774* (2013.01); *A61K 38/1793* (2013.01); *A61K 39/3955* (2013.01); *C07K 14/55* (2013.01); *C07K 14/70532* (2013.01); *C07K 14/70578* (2013.01); *C07K 16/2809* (2013.01); *C07K 2317/622* (2013.01); *C07K 2317/76* (2013.01); *C07K 2319/02* (2013.01); *C07K 2319/30* (2013.01); *C12N 2740/15032* (2013.01); *C12N 2740/15041* (2013.01); *C12N 2740/15043* (2013.01); *C12N 2740/15052* (2013.01); *C12N 2740/16032* (2013.01); *C12N 2740/16041* (2013.01); *C12N 2740/16052* (2013.01)

(58) Field of Classification Search
CPC .......... C12N 15/86; C12N 2740/15032; C12N 2740/15041; C12N 2740/15043; C12N 2740/15052; C12N 2740/16032; C12N 2740/16041; C12N 2740/16052; A61K 38/177; A61K 38/1774; A61K 38/1793; A61K 39/3955; C07K 14/55; C07K 14/70532; C07K 14/70578; C07K 16/2809; C07K 2317/622; C07K 2317/76; C07K 2319/02; C07K 2319/30
See application file for complete search history.

(56) References Cited

U.S. PATENT DOCUMENTS

| | | | |
|---|---|---|---|
| 5,739,018 | A | 4/1998 | Miyanohara et al. |
| 5,994,136 | A | 11/1999 | Naldini et al. |
| 6,013,516 | A | 1/2000 | Verma et al. |
| 6,136,597 | A | 10/2000 | Hope et al. |
| 6,207,455 | B1 | 3/2001 | Chang |
| 6,277,633 | B1 | 8/2001 | Olsen |
| 6,830,892 | B2 | 12/2004 | Marasco et al. |
| 7,439,066 | B2 | 10/2008 | McCray, Jr. et al. |
| 7,939,059 | B2 | 5/2011 | Yang et al. |
| 8,093,042 | B2 | 1/2012 | Charneau et al. |
| 8,163,893 | B2 | 4/2012 | Schaffer et al. |
| 10,273,280 | B2 | 4/2019 | Ma et al. |
| 10,301,370 | B2 | 5/2019 | Payne et al. |

(Continued)

FOREIGN PATENT DOCUMENTS

| | | |
|---|---|---|
| CN | 104395463 A | 3/2015 |
| CN | 107406860 A | 11/2017 |

(Continued)

OTHER PUBLICATIONS

Suarez ER, Chang de K, Sun J, Sui J, Freeman GJ, Signoretti S, Zhu Q, Marasco WA. Chimeric antigen receptor T cells secreting anti-PD-L1 antibodies more effectively regress renal cell carcinoma in a humanized mouse model. Oncotarget. Jun. 7, 2016;7(23):34341-55. (Year: 2016).*

Kloss CC, Lee J, Zhang A, Chen F, Melenhorst JJ, Lacey SF, Maus MV, Fraietta JA, Zhao Y, June CH. Dominant-Negative TGF-β Receptor Enhances PSMA-Targeted Human CAR T Cell Proliferation And Augments Prostate Cancer Eradication. Mol Ther. Jul. 5, 2018;26(7):1855-1866. (Year: 2018).*

Yang H, Joo KI, Ziegler L, Wang P. Cell type-specific targeting with surface-engineered lentiviral vectors co-displaying OKT3 antibody and fusogenic molecule. Pharm Res. Jun. 2009;26(6):1432-45. (Year: 2009).*

Paszkiet et al. Blood. Poster Sessions, Nov. 16, 2004. (Year: 2004).*

(Continued)

*Primary Examiner* — Janet L Andres
*Assistant Examiner* — Ruixue Wang
(74) *Attorney, Agent, or Firm* — Mintz, Levin, Cohn, Ferris, Glovsky and Popeo, P.C.

(57) ABSTRACT

The disclosure relates generally to nucleic acid vectors and packaging cell lines for in vivo expansion of T-cells. More particularly, the disclosure relates to direct intratumoral injection of a lentiviral vector adapted for transduction and drug-mediated expansion of tumor-infiltrating lymphocytes in vivo.

22 Claims, 15 Drawing Sheets

Specification includes a Sequence Listing.

(56) References Cited

U.S. PATENT DOCUMENTS

| | | | |
|---|---|---|---|
| 10,301,389 | B2 | 5/2019 | Ho et al. |
| 10,533,055 | B2 | 1/2020 | Chen et al. |
| 11,517,814 | B2 | 12/2022 | Chalmers et al. |
| 2015/0320799 | A1 | 11/2015 | Low et al. |
| 2016/0311907 | A1* | 10/2016 | Brogdon .............. C12Y 502/00 |
| 2017/0081411 | A1 | 3/2017 | Engels et al. |
| 2017/0253857 | A1 | 9/2017 | Sentman |
| 2019/0091308 | A1 | 3/2019 | Low et al. |
| 2019/0224237 | A1 | 7/2019 | Jensen et al. |
| 2019/0255109 | A1 | 8/2019 | Low et al. |
| 2019/0330343 | A1 | 10/2019 | Maus et al. |
| 2020/0023009 | A1 | 1/2020 | Low et al. |
| 2020/0054676 | A1 | 2/2020 | Low et al. |
| 2020/0087399 | A1 | 3/2020 | Jensen et al. |
| 2020/0123224 | A1 | 4/2020 | Scharenberg |
| 2020/0283729 | A1 | 9/2020 | Loew et al. |
| 2020/0354477 | A1 | 11/2020 | Jensen et al. |
| 2020/0405760 | A1 | 12/2020 | Low et al. |
| 2021/0308267 | A1 | 10/2021 | Low et al. |
| 2021/0317407 | A1 | 10/2021 | Jensen et al. |
| 2022/0000996 | A1 | 1/2022 | Low |
| 2022/0017920 | A1 | 1/2022 | Scharenberg |
| 2022/0031746 | A1 | 2/2022 | Gillenwater et al. |
| 2023/0407330 | A1 | 12/2023 | Scharenberg et al. |

FOREIGN PATENT DOCUMENTS

| | | |
|---|---|---|
| CN | 107531800 A | 1/2018 |
| CN | 108884460 A | 11/2018 |
| CN | 109937050 A | 6/2019 |
| CN | 111971053 A | 11/2020 |
| CN | 112262214 A | 1/2021 |
| EP | 3265570 B1 | 5/2021 |
| GB | 1503500.9 | 3/1978 |
| JP | 2021505621 A | 2/2021 |
| WO | WO 2006/007539 A1 | 1/2006 |
| WO | WO 2007/131092 A2 | 11/2007 |
| WO | WO 2009/014726 A1 | 1/2009 |
| WO | WO 2011/067553 A1 | 6/2011 |
| WO | WO 2015/090229 A1 | 6/2015 |
| WO | WO 2016/009326 A1 | 1/2016 |
| WO | WO 2006/030690 A1 | 3/2016 |
| WO | WO 2016/118775 A1 | 7/2016 |
| WO | WO 2016/139463 A1 | 9/2016 |
| WO | WO 2016/147182 A1 | 9/2016 |
| WO | WO 2017/015427 A1 | 1/2017 |
| WO | WO 2017/029512 A1 | 2/2017 |
| WO | 2017165245 A2 | 9/2017 |
| WO | 2017201432 A2 | 11/2017 |
| WO | 2018111834 A1 | 6/2018 |
| WO | 2018148224 A1 | 8/2018 |
| WO | 2019055946 A1 | 3/2019 |
| WO | 2019156795 A1 | 8/2019 |
| WO | 2019200056 A2 | 10/2019 |
| WO | 2020106992 A1 | 5/2020 |
| WO | 2021076788 A2 | 4/2021 |
| WO | WO2021242719 A1 | 12/2021 |
| WO | 2022164935 A1 | 8/2022 |
| WO | 2023215848 A1 | 11/2023 |

OTHER PUBLICATIONS

Macdonald DC, Hotblack A, Akbar S, Britton G, Collins MK, Rosenberg WC. 4-1BB ligand activates bystander dendritic cells to enhance immunization in trans. J Immunol. Nov. 15, 2014;193(10):5056-64. (Year: 2014).*

International Preliminary Report on Patentability issued he International Searching Authorigy for Application No. PCT/US2019/062675, mailed on May 25, 2021, 7 Pages.

Kafri et al. (Jan. 1999) "A Packaging Cell Line for Lentivirus Vectors", Journal of Virology, 73(1):576-584.

Kim et al. (Apr. 29, 2011) "High Cleavage Efficiency of a 2A Peptide Derived from Porcine Teschovirus-1 in Human Cell Lines, Zebrafish and Mice", PLoS ONE, e18556, 6(4):8 Pages.

Liu et al. (May 19, 2017) "Systematic Comparison Of 2A Peptides For Cloning Multi-Genes In A Polycistronic Vector", Scientific Reports, 7(1):2193 (9 pages).

Milone et al. (2018) "Clinical Use of Lentiviral Vectors", Leukemia, 32(7):1529-1541.

Schlabach et al. (Feb. 1, 2008) "Cancer Proliferation Gene Discovery Through Functional Genomics", Science, 319(5863):620-624.

Wootton et al. (Jun. 1993) "Statistics of Local Complexity in Amino Acid Sequences and Sequence Databases", Computers & Chemistry, 17(2):149-163.

Allan e tal., "Systematic improvements in lentiviral transduction of primary human natural killer cells undergoing ex vivo expansion," Molecular Therapy Method & Clinical Development 20:559-571 (2021).

Derdak et al., "Direct stimulation of T lymphocytes by immunosomes: Virus-like particles decorated with T cell receptor/CD3 ligands plus costimulatory molecules," PNAS 103(35):13144-13149 (2006).

Gerstmayer et al., "Construction and expression in the yeast Pichia pastoris of functionally active soluble forms of the human costimulatory molecules B7-1 and B7-2 and the B7 counter-receptor CTLA-4," FEBS Letters 407:63-68 (1997).

Goodier et al., "CD28 is not directly involved in the response of human CD3-CD56+ natural killer cells to lipopolysaccharide: a role for T cells," Immunology 111:384-390 (2004).

International Search Report and Written Opinion issued by the International Searching Authority for Application No. PCT/US2020/055826, dated May 28, 2021, 11 pages.

Lee et al., "Regulation of CAR T cell-mediated cytokine release syndrome-like toxicity using low molecular weight adapters," Nature Communications 10(1), pp. 1-11 (2019).

Maurice et al., "Efficient gene transfer into human primary blood lymphocytes by surface-engineered lentiviral vectors that display a T cell-activating polypeptide," Blood 99(7):2342-2350 (2002).

Moloney Murine Leukmia Virus Fact Sheet, dated Nov. 19, 2021, 2 pages.

Mosca et al., "Antigen-presenting particular technology using inactivated surface-engineered viruses: induction of immune responses against infectious agents," Retrovirology 4:32, pp. 1-18 (2007).

Ogawa et al., "Construction of Unnatural Heterodimeric Receptors Based on IL-2 and IL-6 Receptor Subunits," Biotechnol Prog 29_1512-1518 (2013).

Opposition to European Patent No. 3265570, ( Patent Application No. 16709502.5), by Margaret Dixon Limited, dated Feb. 4, 2022, 31 pages.

Patentee Response to Office Action issued on Apr. 1, 2019, for European Patent Application No. 16709502.5, dated Oct. 18, 2019, 3 pages.

Paszkiet et al., "CD86 and CD54 Co-Expression on VSV-G Pseudotyped HIV-1 Based Vectors Improves Transduction and Activation of Human Primany CD4+ Lymphocytes," Blood 104(11):1754, 6 pages (2004).

Ridell et al., "The use of anti-CD3 and anti-CD28 monoclonal antibodies to clone and expand human antigen-specific T cells," J. Immunol. Meth. 128 189-201 (1990).

Sharma et al., Efficient infection of a human T-cell line and of human primary peripheral blood leukocytes with a pseudotyped retrovirus vector, Proc. Natl. Acad. Sci. USA 93:11842-11874 (1996).

Sogo et al., "Selective expansion of genetically modified T cells using an antibody/interleukin-2 receptor chimera," J. Immunological Methods 337:16-23 (2008).

Tsuji et al., "Generation of tumor-specific, HLA class I-restricted human Th1 and Tc1 cells by cell engineering with tumor peptide-specific T-cell receptor genes," Blood 106(2):470-476 (2005).

Verhoeyen et al., "Surface-engineering of lentiviral vectors," The Journal of Gene Medicine 6:S83-S94 (2004).

Verhoeyen et al., "IL-7 surface-engineered lentiviral vectors prom te survival and efficient gene transfer in resting primary T lymphocytes," Blood 101(6):2167-2174 (2003).

(56) References Cited

OTHER PUBLICATIONS

Wang et al., "Phenotypic and functional attributes of lentivirus-modified CD19-specific human CD8+ central memory T cells manufactured at clinical scale," J. Immunol Ther 35(9):689-701 (2012).
Yang et al., "Cell Type-Specific Targeting with Surface-Engineered Lentiviral Vectors Co-displaying OKT3 Antibody and Fusogenic Moleculre," Pharm Res. 26(6):1432-1445 (2009).
Altschul et al., "Gapped BLAST and PSI-BLAST: a new generation of protein database search programs," Nucleic Acids Res. 25(17):3389-3402 (1997).
Altschul, et al., "Basic Local Alignment Search Tool," J. Mol. Biol. 215:403-410 (1990).
Anderson et al., "Tim-3: An Emerging Target in the Cancer Immunotherapy Landscape," Cancer Immunol Res. 2(5):393-398 (2014).
Blomer et al., "Highly Efficient and Sustained Gene Transfer in Adult Neurons with a Lentivirus Vector," Journal of Virology 71(9):6641-6649 (1997).
Brewin et al., "Generation of EBV-specific cytotoxic T cells that are resistant to calcineurin inhibitors for the treatment of posttransplantation lymphoproliferative disease," Blood 114:4792-4803 (2009).
Das et al., "Tim-3 and its role in regulating anti-tumor immunity", Immunological Reviews. 276(1):97-111 (2017).
Donnelly et al., "The 'cleavage' activities of foot-and-mouth disease virus 2A site-directed mutants and naturally occurring '2A-like' sequences," J Gen Virol. 82:1027-1041 (2001).
Dull et al., "A third-generation lentivirus vector with a conditional packaging system," J Virol. 72(11):8463-8471 (1998).
Gaererts et al., "Comparison of lentiviral vector titration methods," BMC Biotechnol. 6:34, pp. 1-10 (2006).
Humbert et al. Development of Third generation Cocal Envelope Producer Cell Lines for Robust Lentiviral Gene Transfer into Hematopoietic Stem Cells and T-cells, The Journal of The American Society of Gene Therapy 24(7): 1237-1246 (2016).
Hunter et al. "Chimeric γc cytokine receptors confer cytokine independent engraftment of human T lymphocytes," Mol Immunol. 56(1-2):1-11 (2013).
International Search Report and Written Opinion issued by the International Searching Authority for Application No. PCT/US2019/062675, dated Feb. 5, 2020, 15 pages.
International Search Report and Written Opinion issued by the International Searching Authority for Application No. PCT/US2019/026923, dated Oct. 12, 2019, 23 pages.
Invitation to Pay issued by the International Searching Authority for Application No. PCT/US2019/026923, dated Aug. 30, 2019, 17 pages.
Joglekar et al., "Pseudotyped Lentiviral Vectors: One Vector, Many Guises," Human Gene Therapy Methods 28:291-301 (2017).
Jones et al., "Lentiviral vector design for optimal T cell receptor gene expression in the transduction of peripheral blood lymphocytes and tumor-infiltrating lymphocytes," Hum Gene Ther. 2009 20(6):630-640.
Kafri et al., "Sustained expression of genes delivered directly into liver and muscle by lentiviral vectors," Nature Genetics 17:314-317 (1997).
Karlin and Altschul, "Applications and statistics for multiple high-scoring segments in molecular sequences," Proc. Natl. Acad. Sci. USA 90:5873-5877 (1993).
Karlin and Altschul, "Methods for assessing the statistical significance of molecular sequence features by using general scoring schemes," Proc. Natl. Acad. Sci. USA 87:2264-2268 (1990).
Lee et al. "Optimizing regulatable gene expression using adenoviral vectors," Exp Physiol. 90 (1): 33-37 (2005).
Love et al., "ITAM-mediated Signaling by the T-Cell Antigen Receptor," Cold Spring Harbor Perspectives in Biology, 2(6):a002485-a002485 (2010).
Milone et al. Leukemia, Nature Publishing Group UK, London 32(7):1529-1541 (2018).
Miyoshi et al., "Development of a self-inactivating lentivirus vector," J Virol. 72:8150-8157 (1998).
Naldini et al., "In vivo gene delivery and stable transduction of nondividing cells by a lentiviral vector," Science 272:263-267 (1996).
Naldini et al., "Lentiviruses as gene transfer agents for delivery to non-dividing cells," Expression Vectors and Delivery Systems 9(5):457-463 (1998).
Rosenberg et al., "Adoptive cell transfer as personalized immunotherapy for human cancer", Science 348(6230):62-68 (2015).
Sakuma et al., "Lentiviral vectors: basic to translational," Biochemical Journal 443(3):603-618 (2012).
Schlabach et al., "Synthetic design of strong promoters," Proc Natl Acad Sci USA10:2538-2543 (2010).
Shum et al., "Constitutive Signaling from an Engineered IL7 Receptor Promotes Durable Tumor Elimination by Tumor Redirected T Cells," Cancer Discov. 7(11): 1238-1247 (2017).
Singh et al., "Safe and Effective Gene Therapy for Murine Wiskott-Aldrich Syndrome Using an Insulated Lentiviral Vector," Molecular Therapy—Methods & Clinical Develop 4(1-16) (2017).
Szymczak et al., "Correction of multi-gene deficiency in vivo using a single 'self-cleaving' 2A peptide-based retroviral vector", Nature Biotechnology 22(5):589-594 (2004).
Szymczak-Workman et al., "Design and construction of 2A peptide-linked multicistronic vectors," Cold Spring Harb. Protoc. 2012:199-204 (2012).
Trobridge et al., "Cocal-pseudotyped lentiviral vectors resist inactivation by human serum and efficiently transduce primate hematopoietic repopulating cells", Molecular Therapy: The Journal of the American Society of Gene Therapy, Cell Press, US 18(4):725-733 (2010).
Volpato et al., "Selectively weakened binding of methotrexate by human dihydrofolate reductase allows rapid ex vivo selection of mammalian cells," J Mol Recognition 24:188-198 (2011).
Yam et al., "Ex Vivo Selection and Expansion of Cells Based on Expression of a Mutated Inosine Monophosphate Dehydrogenase 2 after HIV Vector Transduction: Effects on Lymphocytes, Monocytes, and CD34+ Stem Cells," Mol Ther 14(2):236-244 (2006).
Zufferey et al., "Self-Inactivating Lentivirus Vector for Safe and Efficient In Vivo Gene Delivery," J Virol. 72:9873-9880 (1998).
De Felipe et al., (Feb. 2010) "Inhibition of 2A-mediated 'cleavage' of certain artificial polyproteins bearing N-terminal signal sequences", Biotechnology Journal, 5(2):213-223.
Du et al., (Sep. 6, 2016) "Co-Expansion of Cytokine-Induced Killer Cells and Vγ9Vδ2 T Cells for CAR T-Cell Therapy", PLoS One, 11(9):e0161820 (22 pages).
Majumdar et al., (Nov. 15, 2008) "Phage Display of Functional, Full-Length Human and Viral Membrane Proteins", Bioorganic & Medicinal Chemistry Letters, 18(22):5937-5940 (8 pages).
Stogios et al., (Jan. 21, 2011) "Structure and Function of APH(4)-Ia, a Hygromycin B Resistance Enzyme", Journal of Biological Chemistry, 286(3):1966-1975.

* cited by examiner 293T no stim 293T stim 1x sorted HATSE (no stim)

2x sorted HATSE (no stim)

Payload: prom-GFP
Package: pMD2.G (std)

Payload: prom-Cherry
Package: pVT-SEC

Payload: prom-RACCR
Package: pVT-SEC

SEQUENCE LISTING

```
<160> NUMBER OF SEQ ID NOS: 17

<210> SEQ ID NO 1
<211> LENGTH: 1485
<212> TYPE: DNA
<213> ORGANISM: Artificial Sequence
<220> FEATURE:
<223> OTHER INFORMATION: TCP1 - murine Tce1 core enhancer with Dap10
      minimal promoter

<400> SEQUENCE: 1
gtgcacagtc caggcaggtc tccagcttgc aaacctcctg actcagtggc tgggattaca      60
gatttgtgtg agcagcaggc atagattttt ctttaaaaaa aataaaataa aataaaaaat     120
aaagcccagt gttttttcac atggtctggg aagggcctaa caagtgggtt tcctgcagag     180
gaagaggaga gcgttgccct gactctcacc tgctggaggg ggtagagagg ggcctgcagc     240
caagtcatca tttttgaatg tgtgtcagtt acaactacaa aggcaaccaa aaggaggtct     300
tatccgttgt ctgtgagctt cagttgggaa cagcaggcag catttaggtt tggggttttt     360
tttgttgttt ttttttcacc cccaaagcta taaatagccc agcatgtggg gcatcctggc     420
tgctctacct tacacttgag atccaagcag gtagccaccc ccttctcccc tgcagacatt     480
```

```
ttccacaaca cgtatgtgat gagaagaaat gtctcccgga gtggggtgtg tgtgtgtatt      540
cgtatgttgt tattttggtc ttaactttga tgcatgccac ccacgctctc agccaggggt      600
gcgagtcctc cttgatgcct taacgaagtg gtgggcttcg aaggaagaga ggaaggaaga      660
aaacaactct actgtccaga tatgctctta ctttaagttt tgttacttaa agtttgttg       720 atagtctata aactgacttt gttctatgtg tctctaggaa gctatgcttt ctgcagattt      780
tcttaactac ctcccaactc tttggtgaag aaaatggtct ttactctttg ccctttatga      840
gtgagtgtgt gtgtgtgtgt gtgtgtgtgt gtgtgtgtgt atgcaacagt tgttgtcctt      900
gcttattctc catcattttt ttccacatag actagctggc gaatgagctg caggatttca      960
agtctttcta ccctgacccc agtgccgggg ttacggacat gcctgcctgc aacatgagga     1020
cttttcaagt ggacgctgag ggcgctgatc tcaggccctt gtgttctcgt ggaaaacact     1080
ttacaaacag aaccatctcc caagcctgtc ttctcacagt tcatgaactc aggggcgtgt     1140
ctctctgtgg ttagactatg aagccactgt gtcaacgcca ttctcctcga gttttcttgg     1200
ccctacctcc aaaatatttc cagatctccc tagcctgcac accct tgcca cctgtcattc     1260 ccacttggac caggccagca gcctccctgg tctctctgac cctcccccctg agttcgttca    1320 ccaaaggcag taacggagac accccctcaa cacacacagg aagcagatgg ccttgacacc     1380
agcagggtga catccgctat tgctacttct ctgctccccc acagttcctc tggacttctc     1440
tggaccacag tcctctgcca gaccctgcc agaccccagt ccacc                      1485
```

<210> SEQ ID NO 2
<211> LENGTH: 1540
<212> TYPE: DNA
<213> ORGANISM: Artificial Sequence
<220> FEATURE:
<223> OTHER INFORMATION: TCP1 - murine Tce1 core enhancer with Dap10
      minimal promoter

<400> SEQUENCE: 2

```
cacaatactt tggtataaat ttgggattaa ttcgaaagtt cttgattgta aataataaac       60
tttccccaag aaaaggagta cgatgaactt tctttaagaa aaaaaaaaaa aatccaatgc      120
atttcacatg accaaggatt gcacagatgc atttctggac caaggaggag aagattgaac      180
gttggagggg ggctgcccgt ctgacttcct cacctgttcg aggggtcgg gaagggggt       240 taccgctaag tcatcacttt tttatgtgtg tcggttaaaa ctacaaaggc aaccaaaagg      300
aggtcttatc cgttttttgt gagcttcagt tgggagcagc aggtagaaga agctgcactc      360
tggttttact ttttcaccac cgggacctat aaatagatga ggctgtgtgg ctttctcgct     420
gagttacctc caccttcttg cctgggacct cacgatccag gcggctctaa ctcccacatg      480
aacattcgca gctcactgcc cccgcagtca ttttccacaa catgtgtgtg acatgaagaa      540
gtgcgtctca gcatggtgtg tttgtgtgtg tgttgttat ttttgtttta gcgttgagtt      600
ctagatgtct tccgcccaca ctgccaactc tggaagcaag gctttctaaa tgtctcgaag      660
aggtcctcga tatttgttga aggaagaaaa cattgctctt ggttattttt gctccccatg      720
tatccaaaaa tacactaact tttatgtttc ataactattc aatactagtc cctcggccgc      780
tcttacatga tgatgtacag tgtttatctg ccaggccgcg ttttgtacaa actgccttta      840
ctctccccaa ctatttggta aagaaaatta ttttcacttt ttttgttgtt gttgtttgtt      900
tttgtttgtt ttgagaggga atattgctct gttgccaggc tggagtgcag tggagtgatc      960
tcggcttact gcaacctcca cctcccgggt tcaagcgatt ctcctgcctc agcctcctga     1020
```

| | |
|---|---|
| gtcactggga ttacaggcgt gcgccaacac acacagctaa ttttttgtatt tttagtagag | 1080 |
| ctggggtttc accatgttgg ccaggatgat ctcaatctcc tgacctcgtg atctgcccgc | 1140 |
| ttcagcctcc caaagtgctg ggattacagg cgtgagccac cgcgcccggc ctattttcac | 1200 |
| ttttagtaaa tggaaatctg gtatcaaga aagtcagtt tctatttttt cttggcccta | 1260 |
| cctccaaaat atttccagat ctccctagcc tgcacaccct tgccacctgt cattcccact | 1320 |
| tggaccaggc cagcagcctc cctggtctct ctgaccctcc ccctgagttc gttcaccaaa | 1380 |
| ggcagtaacg gagacacccc ctcaacacac acaggaagca gatggccttg acaccagcag | 1440 |
| ggtgacatcc gctattgcta cttctctgct cccccacagt tcctctggac ttctctggac | 1500 |
| cacagtcctc tgccagaccc ctgccagacc ccagtccacc | 1540 |

<210> SEQ ID NO 3
<211> LENGTH: 2416
<212> TYPE: DNA
<213> ORGANISM: Artificial Sequence
<220> FEATURE:
<223> OTHER INFORMATION: TCP3 - full CD2 enhancer with Dap10 minimal
      promoter

<400> SEQUENCE: 3

| | |
|---|---|
| agctttgact agacccgtgt ctgctcattg tgtgaaggat cccagtgtcg aggagaggaa | 60 |
| gctgccgaat aagaaagagc ctcgctggtg tgacagcagg atcaaattca gtcaactcaa | 120 |
| tccggctgag acctccttag tcctcaccag aatgacccga acatgctccc caggtctcag | 180 |
| ctgcaaagct gggtccaaca acctatttgt agatttccat aatgaattaa agcctccatg | 240 |
| cacaaacgtt aacaggagtc accagaaaac ttaacatttt aggtcttact ttcttgactg | 300 |
| ttcagacacg gtcataatga cctgtactgt catccttcaa acaagggaa tctatggata | 360 |
| ctggaggtgt catgaactca tcagatgaca tacaaaaaga taggctaaga acaactcag | 420 |
| ttgaatcaaa tcttaagtgt cttaaatgac tatgattaaa aggtcagacc ccatccccag | 480 |
| ctagcagtca tgcagctgta ctttgaggga agtggggaga aaaaaatagt tttcagttag | 540 |
| agttctaaaa caataggtgg tgagaaggca cctgctttga aatgctggtg ccttgtctgt | 600 |
| ggtcctgtct gcccgccttc tccttggctt cttagacttg ctaaaccttg ttacactctg | 660 |
| gcaggaagct ctgagggcta aaccacaaaa actaagtaca ttcaggactt cctgtgacag | 720 |
| ctcactgagg attgaactac ttttttcctct gaatctgaga gtctattttt ccagcaacca | 780 |
| gagttaatta ctaagggcaa tgatgaatga aacctcatcg cctcccaaaa ttcaaacaca | 840 |
| aaatccagct aggtaacaat tgccacagga tctacccagt agagagatga gggctctggc | 900 |
| cgggcatggt ggctcgtgcc agtaatccta acactttggg aggccaaagc aggtagatca | 960 |
| cctgaggtca ggagtttgag accagcctgg ccaacatggt gaaacccctt ctctacttaa | 1020 |
| aaaaaaaaa aaaaaaatta gccgggcatc gtggcacgca cctataaccc cagctactcg | 1080 |
| ggaggttgag gcagaataat tgcttgaacc ctggggtgtg gaggttgcag tgaggtgaga | 1140 |
| tcgtgtcact tcgctctagc ctgggcaaaa gagcaaaact ccgtctaaaa aaaaaaagga | 1200 |
| gagagagaga gagagagaga gagagatgag ggtcctagct ctgcccnttt ctcattcttc | 1260 |
| atgatacccca tgagtgattt cattggctat ctcaccagaa cagctcatac gccattccct | 1320 |
| taagaaaatc ttccctggtc tattcagccc tgggctctgc cttttcttctg aactcctgtg | 1380 |
| gcattacata tggtacaaaa cacatacacc ctattcaatc cttcatcgtt cattcattca | 1440 |
| acgaacattt attgaacttc tactatgtgt caggctctgt gctaggcact aggaaaacag | 1500 |

```
aggtgtacaa ttgcatctct gctttcaagg agctcaccac ctggtaggca agaaacggac    1560
caaccatggg acaaatgcaa tgcagtatga taaatatagg tcagaggcaa gtgcatgaac    1620
ccagaggaag gactttgaac ccagactgag tggtaagact ggggtgacaa agagggcttc    1680
ctagaggagg gacgtttggg ttgcgttgta atagattaat tgaactggtg aagcagaggt    1740
acagaattac ccatgtagag gcaacagcat gagcaaggct catttggctt tctgtttaca    1800
caaacatgta gtttcttttt caactactgt atttaactga tttgaagatg tcattgattt    1860
ttcaactact gttttcaact ttttgtattt cttttctttt tttaacaact atatttaact    1920
aatttgaaga tggcattgat tttaagtggc atcattcttt tacatgccac taagaaagag    1980
aagaacactt ctcagttgca ttgtaacaaa tactaagata cagtcaactt tcagtcacaa    2040
tcccattcct gagatattaa aatgtgaaaa aatgttattt tatgttagtg cattttagaa    2100
ttgatgaaat gcatagtaaa gattttcttg gccctacctc caaaatattt ccagatctcc    2160
ctagcctgca cacccttgcc acctgtcatt cccacttgga ccaggccagc agcctccctg    2220
gtctctctga ccctccccct gagttcgttc accaaaggca gtaacggaga cacccccctca   2280 acacacacag gaagcagatg gccttgacac cagcagggtg acatccgcta ttgctacttc    2340
tctgctcccc cacagttcct ctggacttct ctggaccaca gtcctctgcc agacccctgc    2400
cagaccccag tccacc                                                    2416

<210> SEQ ID NO 4
<211> LENGTH: 824
<212> TYPE: DNA
<213> ORGANISM: Artificial Sequence
<220> FEATURE:
<223> OTHER INFORMATION: TCP4 - full CD2 enhancer with Dap10 minimal
      promoter

<400> SEQUENCE: 4
ttaagtgtct taaatgacta tgattaaaag gtcagacccc atccccagct agcagtcatg      60
cagctgtact ttgagggaag tggggagaaa aaaatagttt tcagttagag ttctaaaaca     120
ataggtggtg agaaggcacc tgctttgaaa tgctggtgcc ttgtctgtgg tcctgtctgc     180
ccgccttctc cttggcttct tagacttgct aaaccttgtt acactctggc aggaagctct     240
gagggctaaa ccacaaaaac taagtacatt caggacttcc tgtgacagct cactgaggat     300
tgaactactt tttcctctga atctgagagt ctattttttcc agcaaccaga gttaattact     360
aagggcaatg atgaatgaaa cctcatcgcc tcccaaaatt caaacacaaa atccagctag     420
gtaacaattg ccacaggatc tacccagtag agagatgagg gctctggccg ggcatggtgg     480
ctcgtgccag taatcctaac actttgggag gccaaagcag gtagatcacc ttttcttggc     540
cctacctcca aaatatttcc agatctccct agcctgcaca cccttgccac ctgtcattcc     600
cacttggacc aggccagcag cctccctggt ctctctgacc ctcccccctga gttcgttcac     660 caaaggcagt aacggagaca cccccctcaac acacacagga agcagatggc cttgacacca     720
gcagggtgac atccgctatt gctacttctc tgctccccca cagttcctct ggacttctct     780
ggaccacagt cctctgccag acccctgcca gacccccagtc cacc                    824

<210> SEQ ID NO 5
<211> LENGTH: 347
<212> TYPE: DNA
<213> ORGANISM: Artificial Sequence
<220> FEATURE:
<223> OTHER INFORMATION: MND Promoter
```

<400> SEQUENCE: 5

```
gaacagagaa acaggagaat atgggccaaa caggatatct gtggtaagca gttcctgccc      60
cggctcaggg ccaagaacag ttggaacagc agaatatggg ccaaacagga tatctgtggt     120
aagcagttcc tgccccggct cagggccaag aacagatggt ccccagatgc ggtcccgccc     180
tcagcagttt ctagagaacc atcagatgtt tccagggtgc cccaaggacc tgaaatgacc     240
ctgtgcctta tttgaactaa ccaatcagtt cgcttctcgc ttctgttcgc gcgcttctgc     300
tccccgagct ctatataagc agagctcgtt tagtgaaccg tcagatc                   347
```

<210> SEQ ID NO 6
<211> LENGTH: 9859
<212> TYPE: DNA
<213> ORGANISM: Artificial Sequence
<220> FEATURE:
<223> OTHER INFORMATION: lentiviral vector vivo-TIL 104 - LNGFR

<400> SEQUENCE: 6

```
agcttaatgt agtcttatgc aatactcttg tagtcttgca acatggtaac gatgagttag      60
caacatgcct tacaaggaga gaaaaagcac cgtgcatgcc gattggtgga agtaaggtgg     120
tacgatcgtg ccttattagg aaggcaacag acgggtctga catggattgg acgaaccact     180
gaattgccgc attgcagaga tattgtattt aagtgcctag ctcgatacaa taaacgggtc     240
tctctggtta gaccagatct gagcctggga gctctctggc taactaggga acccactgct     300
taagcctcaa taaagcttgc cttgagtgct tcaagtagtg tgtgcccgtc tgttgtgtga     360
ctctggtaac tagagatccc tcagaccctt ttagtcagtg tggaaaatct ctagcagtgg     420
cgcccgaaca gggacttgaa agcgaaaggg aaaccagagg agctctctcg acgcaggact     480
cggcttgctg aagcgcgcac ggcaagaggc gaggggcggc gactggtgag tacgccaaaa     540
attttgacta gcggaggcta aaggagaga tgggtgcg agagcgtcag tattaagcgg      600
gggagaatta gatcgcgatg ggaaaaaatt cggttaaggc caggggggaaa gaaaaaatat     660
aaattaaaac atatagtatg ggcaagcagg gagctagaac gattcgcagt taatcctggc     720
ctgttagaaa catcagaagg ctgtagacaa atactgggac agctacaacc atcccttcag     780
acaggatcag aagaacttag atcattatat aatacagtag caaccctcta ttgtgtgcat     840
caaaggatag agataaaaga caccaaggaa gctttagaca gatagagga agagcaaaac     900
aaaagtaaga ccaccgcaca gcaagcggcc gctgatcttc agacctggag gaggagatat     960
gagggacaat tggagaagtg aattatataa atataaagta gtaaaaattg aaccattagg    1020
agtagcaccc accaaggcaa agagaagagt ggtgcagaga gaaaaaagag cagtgggaat    1080
aggagctttg ttccttgggt tcttgggagc agcaggaagc actatgggcg cagcctcaat    1140
gacgctgacg gtacaggcca gacaattatt gtctggtata gtgcagcagc agaacaattt    1200
gctgagggct attgaggcgc aacagcatct gttgcaactc acagtctggg gcatcaagca    1260
gctccaggca agaatcctgg ctgtggaaag atacctaaag gatcaacagc tcctggggat    1320
ttggggttgc tctggaaaac tcatttgcac cactgctgtg ccttggaatg ctagttggag    1380
taataaatct ctggaacaga tttgaatca cacgacctgg atgagtggg acagagaaat    1440
taacaattac acaagcttaa tacactcctt aattgaagaa tcgcaaaacc agcaagaaaa    1500
gaatgaacaa gaattattgg aattagataa atgggcaagt ttgtggaatt ggtttaacat    1560
aacaaattgg ctgtggtata taaaattatt cataatgata gtaggaggct tggtaggttt    1620
```

```
aagaatagtt tttgctgtac tttctatagt gaatagagtt aggcagggat attcaccatt    1680
atcgtttcag acccacctcc caaccccgag gggacccgac aggcccgaag gaatagaaga    1740
agaaggtgga gagagagaca gagacagatc cattcgatta gtgaacggat ctcgacggta    1800
tcggttaact tttaaaagaa aagggggggat tgggggggtac agtgcagggg aaagaatagt   1860
agacataata gcaacagaca tacaaactaa agaattacaa aacaaatta caaaaattca    1920
aaattttatc gatcacgaga ctagcctcga gaagcttgat atcgaattcc cacgggttg     1980
gacgcgtagg aacagagaaa caggagaata tgggccaaac aggatatctg tggtaagcag   2040
ttcctgcccc ggctcagggc caagaacagt tggaacagca gaatatgggc caaacaggat    2100
atctgtggta agcagttcct gccccggctc agggccaaga acagatggtc cccagatgcg    2160
gtcccgccct cagcagtttc tagagaacca tcagatgttt ccagggtgcc ccaaggacct   2220
gaaatgaccc tgtgccttat ttgaactaac caatcagttc gcttctcgct tctgttcgcg    2280
cgcttctgct ccccgagctc tatataagca gagctcgttt agtgaaccgt cagatcgcta    2340
gcaccggtcc tgcagggccg ccaccatgcc tctgggcctg ctgtggctgg gcctggccct    2400
gctgggcgcc ctgcacgccc aggccggcgt gcaggtggag acaatctccc caggcgacgg    2460
acgcacattc cctaagcggg gccagacctg cgttgtgcac tatacaggca tgctggagga    2520
tggcaagaag tttgacagct cccgggatag aaacaagcca ttcaagttta tgctgggcaa   2580
gcaggaagtg atcagaggct gggagggagggg cgtggcccag atgtctgtgg ccagagggc    2640
caagctgacc atcagcccag actacgccta tggagcaaca ggccacccag gaatcatccc    2700
acctcacgcc accctggtgt cgatgtggga gctgctgaag ctgggcgagg atccaacac     2760
atcaaaagag aacccctttc tgttcgcatt ggaggccgta gtcatatctg ttggatccat    2820
gggacttatt atctccctgt tgtgtgtgta cttctggctg gaacggacta tgcccaggat    2880
ccccacgctc aagaatctgg aagatctcgt cacagaatac catggtaatt tcagcgcctg    2940
gagcggagtc tctaagggtc tggccgaatc cctccaaccc gattattctg aacgttgtg     3000
cctcgtatcc gaaataccac caaaaggcgg ggctctgggt gagggcccag ggcgagtcc     3060
gtgcaatcaa cacagcccgt attgggcccc tccttgttat acgttgaagc ccgaaactgg    3120
aagcggagct actaacttca gcctgctgaa gcaggctgga gacgtggagg agaaccctgg    3180
acctatggca ctgcccgtga ccgccctgct gctgcctctg gccctgctgc tgcacgcagc    3240
ccggcctatc ctgtggcacg agatgtggca cgagggcctg gaggaggcca gcaggctgta    3300
ttttggcgag cgcaacgtga agggcatgtt cgaggtgctg gagcctctgc acgccatgat    3360
ggagagaggc ccacagaccc tgaaggagac atccttttaac caggcctatg gacgggacct    3420
gatggaggca caggagtggt gcagaaagta catgaagtct ggcaatgtga aggacctgct    3480
gcaggcctgg gatctgtact atcacgtgtt tcggagaatc tccaagggca aagacacgat    3540
tccgtggctt gggcatctgc tcgttgggct gagtggtgcg tttggttttca tcatcttggt    3600
ctatctcttg atcaattgca gaaatacagg cccttggctg aaaaaagtgc tcaagtgtaa   3660
tacccccgac ccaagcaagt tcttctccca gctttcttca gagcatggag gcgatgtgca    3720
gaaatggctc tcttcacctt tccctcctc aagcttctcc ccgggagggc tggcgcccga    3780
gatttcacct cttgaggtac ttgaacgaga caaggttacc caacttctcc ttcaacagga    3840
taaggtaccc gaacctgcga gcctttagctc caaccactct cttacgagct gcttcaccaa    3900
tcagggatac ttcttttttcc accttcccga tgcgctggaa atcgaagctt gtcaagttta    3960
ctttacctat gatccatata gcgaggaaga tcccgacgaa ggagtcgccg gtgcgcccac    4020
```

```
gggttcctca ccccaacctc tccagcctct ctcaggagaa gatgatgctt attgcacttt    4080
tcccagtaga gacgatctcc tcctcttttc tccatctctt ttgggggggac cttccccccc    4140 ttctacggca cctggcgggt ctggtgctgg cgaggagcgg atgccgccgt ccctccagga    4200
gcgagtacca cgagattggg atccccagcc acttggaccc cccaccccg gcgtacctga    4260 ccttgtcgat tttcaacctc ccctgaatt ggtgctgcga gaggctgggg aggaagttcc    4320
ggacgctggg ccgagggagg gcgtgtcctt tccatggagt aggcctccag gtcaaggcga    4380
gtttagggct ctcaacgcgc ggctgccgtt gaatacagac gcttatctct cactgcagga    4440
actgcaaggt caggacccaa cacatcttgt aggatctggt gctactaatt tttctctttt    4500
gaagcaagct ggagatgttg aagagaaccc cggtccggag atgtggcatg agggtctgga    4560
agaagcgtct cgactgtact ttggtgagcg caatgtgaag gcatgtttg aagtcctcga    4620 accccttcat gccatgatgg aacgcggacc ccagaccttg aaggagacaa gttttaacca    4680
agcttacgga agagacctga tggaagccca ggaatggtgc aggaaataca tgaaaagcgg    4740
gaatgtgaag gacttgctcc aagcgtggga cctgtactat catgtcttta ggcgcattag    4800
taagggcagc ggcgccacca acttcagcct gctgaagcag gccggcgacg tggaggagaa    4860
ccccggcccc ggtgctggcg caactggacg cgctatggat ggacctcgct tgctgcttct    4920
tctgcttctc ggggtctctt tgggtggtgc taaggaagca tgcccaacgg gactttatac    4980
gcatagcgga gagtgttgca aagcttgtaa cctgggcgaa ggcgtcgcgc aaccttgtgg    5040
tgcaaatcaa accgtctgcg agccatgttt ggactctgtt acgtttagtg acgtagtatc    5100
tgcgacagag ccatgcaagc cttgtacgga atgtgtagga ttgcagagca tgtctgcccc    5160
ttgtgtagaa gccgacgatg cagttttcag gtgcgcgtat ggctattacc aagacgaaac    5220
aaccggacga tgtgaagctt gccgagtttg tgaagcgggt tccgggcttg tattctcctg    5280
tcaggataag cagaacaccg tctgcgaaga gtgccccgat ggtacctaca gcgatgaagc    5340
gaaccatgta gacccatgcc tgccttgcac cgtttgtgaa gacacggaac gacagttgcg    5400
ggaatgtacc cggtgggcag acgccgagtg cgaagagatt ccaggccgct ggatcacgcg    5460
aagtaccccg ccagaaggtt ccgacagtac tgcaccaagc acccaagaac cagaggcgcc    5520
ccccgagcag gacctgattg cctccaccgt ggcgggtgtt gttactacgg ttatgggctc    5580
atcccagccc gttgttaccc gaggaactac agacaacctg attccggtat attgttctat    5640
cttggcggct gtagtagttg gcttggtcgc gtacatcgct ttcaaaagat gaacgccggc    5700
gctagtgtcg acaatcaacc tctggattac aaaatttgtg aaagattgac tggtattctt    5760
aactatgttg ctccttttac gctatgtgga tacgctgctt taatgccttt gtatcatgct    5820
attgcttccc gtatgctttc attttctcc tccttgtata atcctggtt gctgtctctt    5880 tatgaggagt tgtggcccgt tgtcaggcaa cgtggcgtgg tgtgcactgt gtttgctgac    5940
gcaaccccca ctggttgggg cattgccacc acctgtcagc tcctttccgg actttcgct    6000 ttccccctcc ctattgccac ggcggaactc atcgccgcct gccttgcccg ctgctggaca    6060
ggggctcggc tgttgggcac tgacaattcc gtggtgttgt cggggaagct gacgtccttt    6120
ccatggctgc tcgcctgtgt tgccacctgg attctgcgcg gacgtccctt ctgctacgtc    6180
ccttcggccc tcaatccagc ggaccttcct tcccgcggcc tgctgccggc tctgcggcct    6240
cttccgcgtc ttcgccttcg ccctcagacg agtcggatct ccctttgggc cgcctccccg    6300
cctggaattc gagctcggta cctttaagac caatgactta caaggcagct gtagatctta    6360
```

-continued

```
gccactttt  taaagaaaag  gggggactgg  aagggctaat  tcactcccaa  cgaagacaag    6420
atctgctttt  tgcttgtact  gggtctctct  ggttagacca  gatctgagcc  tgggagctct    6480
ctggctaact  agggaaccca  ctgcttaagc  ctcaataaag  cttgccttga  gtgcttcaag    6540
tagtgtgtgc  ccgtctgttg  tgtgactctg  gtaactagag  atccctcaga  ccctttagt     6600 cagtgtggaa  aatctctagc  agtagtagtt  catgtcatct  tattattcag  tatttataac    6660
ttgcaaagaa  atgaatatca  gagagtgaga  ggaacttgtt  tattgcagct  tataatggtt    6720
acaaataaag  caatagcatc  acaaatttca  caaataaagc  attttttca   ctgcattcta    6780 gttgtggttt  gtccaaactc  atcaatgtat  cttatcatgt  ctggctctag  ctatcccgcc    6840
cctaactccg  cccagttccg  cccattctcc  gccccatggc  tgactaattt  tttttattta    6900
tgcagaggcc  gaggccgcct  cggcctctga  gctattccag  aagtagtgag  gaggcttttt    6960
tggaggccta  ggcttttgcg  tcgagacgta  cccaattcgc  cctatagtga  gtcgtattac    7020
gcgcgctcac  tggccgtcgt  tttacaacgt  cgtgactggg  aaaaccctgg  cgttacccaa    7080
cttaatcgcc  ttgcagcaca  tccccctttc  gccagctggc  gtaatagcga  agaggcccgc    7140
accgatcgcc  cttcccaaca  gttgcgcagc  ctgaatggcg  aatggcgcga  cgcgccctgt    7200
agcggcgcat  taagcgcggc  gggtgtggtg  gttacgcgca  gcgtgaccgc  tacacttgcc    7260
agcgccctag  cgcccgctcc  tttcgctttc  ttcccttcct  ttctcgccac  gttcgccggc    7320
tttccccgtc  aagctctaaa  tcggggctc   cctttagggt  tccgatttag  tgctttacgg    7380
cacctcgacc  ccaaaaaact  tgattagggt  gatggttcac  gtagtgggcc  atcgccctga    7440
tagacggttt  ttcgcccttt  gacgttggag  tccacgttct  ttaatagtgg  actcttgttc    7500
caaactggaa  caacactcaa  ccctatctcg  gtctattctt  ttgatttata  agggattttg    7560
ccgatttcgg  cctattggtt  aaaaaatgag  ctgatttaac  aaaaatttaa  cgcgaatttt    7620
aacaaaatat  taacgtttac  aatttcccag  gtggcacttt  tcggggaaat  gtgcgcggaa    7680
cccctatttg  tttattttc   taaatacatt  caaatatgta  tccgctcatg  agacaataac    7740
cctgataaat  gcttcaataa  tattgaaaaa  ggaagagtat  gagtattcaa  catttccgtg    7800
tcgcccttat  tccctttttt  gcggcatttt  gccttcctgt  ttttgctcac  ccagaaacgc    7860
tggtgaaagt  aaaagatgct  gaagatcagt  tgggtgcacg  agtgggttac  atcgaactgg    7920
atctcaacag  cggtaagatc  cttgagagtt  ttcgccccga  agaacgtttt  ccaatgatga    7980
gcacttttaa  agttctgcta  tgtggcgcgg  tattatcccg  tattgacgcc  gggcaagagc    8040
aactcggtcg  ccgcatacac  tattctcaga  atgacttggt  tgagtactca  ccagtcacag    8100
aaaagcatct  tacggatggc  atgacagtaa  gagaattatg  cagtgctgcc  ataaccatga    8160
gtgataacac  tgcggccaac  ttacttctga  caacgatcgg  aggaccgaag  gagctaaccg    8220
cttttttgca  caacatgggg  gatcatgtaa  ctcgccttga  tcgttgggaa  ccggagctga    8280
atgaagccat  accaaacgac  gagcgtgaca  ccacgatgcc  tgtagcaatg  caacaacgt     8340 tgcgcaaact  attaactggc  gaactactta  ctctagcttc  ccggcaacaa  ttaatagact    8400
ggatggaggc  ggataaagtt  gcaggaccac  ttctgcgctc  ggcccttccg  gctggctggt    8460
ttattgctga  taaatctgga  gccggtgagc  gtgggtctcg  cggtatcatt  gcagcactgg    8520
ggccagatgg  taagccctcc  cgtatcgtag  ttatctacac  gacggggagt  caggcaacta    8580
tggatgaacg  aaatagacag  atcgctgaga  taggtgcctc  actgattaag  cattggtaac    8640
tgtcagacca  agtttactca  tatatacttt  agattgattt  aaaacttcat  ttttaattta    8700
aaaggatcta  ggtgaagatc  cttttgata   atctcatgac  caaaatccct  taacgtgagt    8760
```

```
tttcgttcca ctgagcgtca gacccgtag aaaagatcaa aggatcttct tgagatcctt    8820
tttttctgcg cgtaatctgc tgcttgcaaa caaaaaaacc accgctacca gcggtggttt    8880
gtttgccgga tcaagagcta ccaactcttt ttccgaaggt aactggcttc agcagagcgc    8940
agataccaaa tactgtcctt ctagtgtagc cgtagttagg ccaccacttc aagaactctg    9000
tagcaccgcc tacatacctc gctctgctaa tcctgttacc agtggctgct gccagtggcg    9060
ataagtcgtg tcttaccggg ttggactcaa gacgatagtt accggataag cgcagcggt    9120 cgggctgaac ggggggttcg tgcacacagc ccagcttgga gcgaacgacc tacaccgaac    9180
tgagatacct acagcgtgag ctatgagaaa gcgccacgct cccgaaggg agaaaggcgg    9240 acaggtatcc ggtaagcggc agggtcggaa caggagagcg cacgagggag cttccagggg    9300
gaaacgcctg gtatctttat agtcctgtcg ggtttcgcca cctctgactt gagcgtcgat    9360
ttttgtgatg ctcgtcaggg gggcggagcc tatgaaaaaa cgccagcaac gcggcctttt    9420
tacggttcct ggccttttgc tggccttttg ctcacatgtt ctttcctgcg ttatcccctg    9480
attctgtgga taaccgtatt accgcctttg agtgagctga taccgctcgc cgcagccgaa    9540
cgaccgagcg cagcgagtca gtgagcgagg aagcggaaga gcgcccaata cgcaaaccgc    9600
ctctccccgc gcgttggccg attcattaat gcagctggca cgacaggttt cccgactgga    9660
aagcgggcag tgagcgcaac gcaattaatg tgagttagct cactcattag gcaccccagg    9720
ctttacactt tatgcttccg gctcgtatgt tgtgtggaat tgtgagcgga taacaatttc    9780
acacaggaaa cagctatgac catgattacg ccaagcgcgc aattaaccct cactaaaggg    9840
aacaaaagct ggagctgca                                                  9859

<210> SEQ ID NO 7
<211> LENGTH: 10997
<212> TYPE: DNA
<213> ORGANISM: Artificial Sequence
<220> FEATURE:
<223> OTHER INFORMATION: lentiviral vector vivo-TIL 105 - TCP1

<400> SEQUENCE: 7
agcttaatgt agtcttatgc aatactcttg tagtcttgca acatggtaac gatgagttag      60
caacatgcct tacaaggaga gaaaaagcac cgtgcatgcc gattggtgga agtaaggtgg     120
tacgatcgtg ccttattagg aaggcaacag acgggtctga catggattgg acgaaccact     180
gaattgccgc attgcagaga tattgtattt aagtgcctag ctcgatacaa taaacgggtc     240
tctctggtta gaccagatct gagcctggga gctctctggc taactaggga acccactgct     300
taagcctcaa taaagcttgc cttgagtgct tcaagtagtg tgtgcccgtc tgttgtgtga     360
ctctggtaac tagagatccc tcagaccctt ttagtcagtg tggaaaatct ctagcagtgg     420
cgcccgaaca gggacttgaa agcgaaaggg aaaccagagg agctctctcg acgcaggact     480
cggcttgctg aagcgcgcac ggcaagaggc gaggggcggc gactggtgag tacgccaaaa     540
attttgacta gcggaggcta agaagagaga gatgggtgcg agagcgtcag tattaagcgg     600
gggagaatta gatcgcgatg ggaaaaaatt cggttaaggc caggggggaa gaaaaaatat     660
aaattaaaac atatagtatg ggcaagcagg gagctagaac gattcgcagt taatcctggc     720
ctgttagaaa catcagaagg ctgtagacaa atactgggac agctacaacc atcccttcag     780
acaggatcag aagaacttag atcattatat aatacagtag caaccctcta ttgtgtgcat     840
caaaggatag agataaaaga caccaaggaa gctttagaca agatagagga agagcaaaac     900
```

-continued

```
aaaagtaaga ccaccgcaca gcaagcggcc gctgatcttc agacctggag gaggagatat     960
gagggacaat tggagaagtg aattatataa atataaagta gtaaaaattg aaccattagg    1020
agtagcaccc accaaggcaa agagaagagt ggtgcagaga gaaaaaagag cagtgggaat    1080
aggagctttg ttccttgggt tcttgggagc agcaggaagc actatgggcg cagcctcaat    1140
gacgctgacg gtacaggcca gacaattatt gtctggtata gtgcagcagc agaacaattt    1200
gctgagggct attgaggcgc aacagcatct gttgcaactc acagtctggg gcatcaagca    1260
gctccaggca agaatcctgg ctgtggaaag atacctaaag gatcaacagc tcctggggat    1320
ttggggttgc tctggaaaac tcatttgcac cactgctgtg ccttggaatg ctagttggag    1380
taataaatct ctggaacaga tttggaatca cacgacctgg atggagtggg acagagaaat    1440
taacaattac acaagcttaa tacactcctt aattgaagaa tcgcaaaacc agcaagaaaa    1500
gaatgaacaa gaattattgg aattagataa atgggcaagt ttgtggaatt ggtttaacat    1560
aacaaattgg ctgtggtata taaaattatt cataatgata gtaggaggct tggtaggttt    1620
aagaatagtt tttgctgtac tttctatagt gaatagagtt aggcagggat attcaccatt    1680
atcgtttcag acccacctcc caaccccgag gggacccgac aggcccgaag gaatagaaga    1740
agaaggtgga gagagagaca gagacagatc cattcgatta gtgaacggat ctcgacggta    1800
tcggttaact tttaaaagaa aagggggggat tggggggtac agtgcagggg aaagaatagt    1860
agacataata gcaacagaca tacaaactaa agaattacaa aaacaaatta caaaaattca    1920
aaattttatc gatcacgaga ctagcctcga gaagcttgat atcgaattcc cacggggttg    1980
gacgcgtagg tgcacagtcc aggcaggtct ccagcttgca aacctcctga ctcagtggct    2040
gggattacag atttgtgtga gcagcaggca tagatttttc tttaaaaaaa ataaaataaa    2100
ataaaaaata aagcccagtg ttttttcaca tggtctggga agggcctaac aagtgggttt    2160
cctgcagagg aagaggagag cgttgccctg actctcacct gctggagggg gtagagaggg    2220
gcctgcagcc aagtcatcat ttttgaatgt gtgtcagtta caactacaaa ggcaaccaaa    2280
aggaggtctt atccgttgtc tgtgagcttc agttgggaac agcaggcagc atttaggttt    2340
gggtttttt ttgttgtttt tttttcaccc ccaaagctat aaatagccca gcatgtgggg    2400
catcctggct gctctacctt acacttgaga tccaagcagg tagccacccc cttctcccct    2460
gcagacattt tccacaacac gtatgtgatg agaagaaatg tctcccggag tggggtgtgt    2520
gtgtgtattc gtatgttgtt attttggtct taactttgat gcatgccacc cacgctctca    2580
gccaggggtg cgagtcctcc ttgatgcctt aacgaagtgg tgggcttcga aggaagagag    2640
gaaggaagaa aacaactcta ctgtccagat atgctcttac tttaagtttt tgttacttaa    2700
agtttgttga tagtctataa actgactttg ttctatgtgt ctctaggaag ctatgctttc    2760
tgcagatttt cttaactacc tcccaactct ttggtgaaga aaatggtctt tactctttgc    2820
cctttatgag tgagtgtgtg tgtgtgtgtg tgtgtgtgtg tgtgtgtgta tgcaacagtt    2880
gttgtccttg cttattctcc atcattttt tccacataga ctagctggcg aatgagctgc    2940
aggatttcaa gtcttttctac cctgacccca gtgccggggt tacggacatg cctgcctgca    3000
acatgaggac ttttcaagtg gacgctgagg gcgctgatct caggcccttg tgttctcgtg    3060
gaaaacactt tacaaacaga accatctccc aagcctgtct tctcacagtt catgaactca    3120
ggggcgtgtc tctctgtggt tagactatga agccactgtg tcaacgccat tctcctcgag    3180
ttttcttggc cctacctcca aaatatttcc agatctccct agcctgcaca cccttgccac    3240
ctgtcattcc cacttggacc aggccagcag cctccctggt ctctctgacc ctcccccctga   3300
```

```
gttcgttcac caaaggcagt aacggagaca cccctcaac acacacagga agcagatggc    3360
cttgacacca gcagggtgac atccgctatt gctacttctc tgctccccca cagttcctct    3420
ggacttctct ggaccacagt cctctgccag acccctgcca gaccccagtc caccgctagc    3480
accggtcctg cagggccgcc accatgcctc tgggcctgct gtggctgggc ctggccctgc    3540
tgggcgccct gcacgcccag gccggcgtgc aggtggagac aatctcccca ggcgacggac    3600
gcacattccc taagcggggc cagacctgcg ttgtgcacta tacaggcatg ctggaggatg    3660
gcaagaagtt tgacagctcc cgggatagaa acaagccatt caagtttatg ctgggcaagc    3720
aggaagtgat cagaggctgg gaggagggcg tggcccagat gtctgtgggc cagagggcca    3780
agctgaccat cagcccagac tacgcctatg agcaacagg ccacccagga atcatcccac    3840
ctcacgccac cctggtgttc gatgtggagc tgctgaagct gggcgaggga tccaacacat    3900
caaaagagaa cccttttctg ttcgcattgg aggccgtagt catatctgtt ggatccatgg    3960
gacttattat ctccctgttg tgtgtgtact tctggctgga acggactatg cccaggatcc    4020
ccacgctcaa gaatctggaa gatctcgtca cagaatacca tggtaatttc agcgcctgga    4080
gcggagtctc taagggtctg gccgaatccc tccaacccga ttattctgaa cggttgtgcc    4140
tcgtatccga ataccacca aaaggcgggg ctctgggtga gggcccaggg gcgagtccgt    4200
gcaatcaaca cagcccgtat tgggcccctc cttgttatac gttgaagccc gaaactggaa    4260
gcggagctac taacttcagc ctgctgaagc aggctggaga cgtggaggag aaccctggac    4320
ctatggcact gcccgtgacc gccctgctgc tgcctctggc cctgctgctg cacgcagccc    4380
ggcctatcct gtggcacgag atgtggcacg agggcctgga ggaggccagc aggctgtatt    4440
ttggcgagcg caacgtgaag ggcatgttcg aggtgctgga gcctctgcac gccatgatgg    4500
agagaggccc acagaccctg aaggagacat cctttaacca ggcctatgga cgggacctga    4560
tggaggcaca ggagtggtgc agaaagtaca tgaagtctgg caatgtgaag gacctgctgc    4620
aggcctggga tctgtactat cacgtgtttc ggagaatctc caagggcaaa gacacgattc    4680
cgtggcttgg gcatctgctc gttgggctga gtggtgcgtt tggtttcatc atcttggtct    4740
atctcttgat caattgcaga aatacaggcc cttggctgaa aaaagtgctc aagtgtaata    4800
cccccgaccc aagcaagttc ttctcccagc tttcttcaga gcatggaggc gatgtgcaga    4860
aatggctctc ttcaccttt ccctcctcaa gcttctcccc ggaggggctg gcgcccgaga    4920
tttcacctct tgaggtactt gaacgagaca aggttaccca acttctcctt caacaggata    4980
aggtacccga acctgcgagc cttagctcca accactctct tacgagctgc ttcaccaatc    5040
agggatactt cttttccac cttcccgatg cgctggaaat cgaagcttgt caagtttact    5100
ttacctatga tccatatagc gaggaagatc ccgacgaagg agtcgccggt gcgcccacgg    5160
gttcctcacc ccaacctctc cagcctctct caggagaaga tgatgcttat tgcacttttc    5220
ccagtagaga cgatcctcc ctcttttctc catctctttt gggggacctt cccccctt    5280
ctacggcacc tggcgggtct ggtgctggcg aggagcggat gccgccgtcc ctccaggagc    5340
gagtaccacg agattgggat ccccagccac ttggaccccc cacccccggc gtacctgacc    5400
ttgtcgattt tcaacctccc cctgaattgg tgctgcgaga ggctggggag gaagttccgg    5460
acgctgggcc gagggagggc gtgtcctttc catggagtag gcctccaggt caaggcgagt    5520
ttagggctct caacgcgcgg ctgccgttga atacagacgc ttatctctca ctgcaggaac    5580
tgcaaggtca ggacccaaca catcttgtag gatctggtgc tactaatttt tctcttttga    5640
```

```
agcaagctgg agatgttgaa gagaaccccg gtccggagat gtggcatgag ggtctggaag    5700
aagcgtctcg actgtacttt ggtgagcgca atgtgaaggg catgtttgaa gtcctcgaac    5760
cccttcatgc catgatggaa cgcggacccc agaccttgaa ggagacaagt tttaaccaag    5820
cttacggaag agacctgatg gaagcccagg aatggtgcag gaaatacatg aaaagcggga    5880
atgtgaagga cttgctccaa gcgtgggacc tgtactatca tgtctttagg cgcattagta    5940
agggcagcgg cgccaccaac ttcagcctgc tgaagcaggc cggcgacgtg gaggagaacc    6000
ccggccccgg tgctggcgca actggacgcg ctatggatgg acctcgcttg ctgcttcttc    6060
tgcttctcgg ggtctctttg ggtggtgcta aggaagcatg cccaacggga ctttatacgc    6120
atagcggaga gtgttgcaaa gcttgtaacc tgggcgaagg cgtcgcgcaa ccttgtggtg    6180
caaatcaaac cgtctgcgag ccatgtttgg actctgttac gtttagtgac gtagtatctg    6240
cgacagagcc atgcaagcct tgtacggaat gtgtaggatt gcagagcatg tctgcccctt    6300
gtgtagaagc cgacgatgca gtttgcaggt gcgcgtatgg ctattaccaa gacgaaacaa    6360
ccggacgatg tgaagcttgc cgagtttgtg aagcgggttc cgggcttgta ttctcctgtc    6420
aggataagca gaacaccgtc tgcgaagagt gccccgatgg tacctacagc gatgaagcga    6480
accatgtaga cccatgcctg ccttgcaccg tttgtgaaga cacggaacga cagttgcggg    6540
aatgtacccg gtgggcagac gccgagtgcg aagagattcc aggccgctgg atcacgcgaa    6600
gtaccccgcc agaaggttcc gacagtactg caccaagcac caagaaccaa gaggcgcccc    6660
ccgagcagga cctgattgcc tccaccgtgg cgggtgttgt tactacggtt atgggctcat    6720
cccagcccgt tgttacccga ggaactacag acaacctgat tccggtatat tgttctatct    6780
tggcggctgt agtagttggc ttggtcgcgt acatcgcttt caaaagatga cgccggcgac    6840
tagtgtcgac aatcaacctc tggattacaa aatttgtgaa agattgactg gtattcttaa    6900
ctatgttgct ccttttacgc tatgtggata cgctgcttta atgcctttgt atcatgctat    6960
tgcttcccgt atggctttca ttttctcctc cttgtataaa tcctggttgc tgtctcttta    7020
tgaggagttg tggcccgttg tcaggcaacg tggcgtggtg tgcactgtgt ttgctgacgc    7080 aaccccccact ggttggggca ttgccaccac ctgtcagctc ctttccggga ctttcgcttt    7140 cccccctccct attgccacgg cggaactcat cgccgcctgc cttgcccgct gctggacagg    7200
ggctcggctg ttgggcactg acaattccgt ggtgttgtcg gggaagctga cgtccttttcc   7260 atggctgctc gcctgtgttg ccacctggat tctgcgcggg acgtccttct gctacgtccc    7320
ttcggccctc aatccagcgg accttccttc ccgcggcctg ctgccggctc tgcggcctct    7380
tccgcgtctt cgccttcgcc ctcagacgag tcggatctcc ctttgggccg cctccccgcc    7440
tggaattcga gctcggtacc tttaagacca atgacttaca aggcagctgt agatcttagc    7500
cactttttaa aagaaaaggg gggactggaa gggctaattc actcccaacg aagacaagat    7560 ctgcttttg cttgtactgg gtctctctgg ttagaccaga tctgagcctg ggagctctct    7620
ggctaactag ggaacccact gcttaagcct caataaagct tgccttgagt gcttcaagta    7680
gtgtgtgccc gtctgttgtg tgactctggt aactagagat ccctcagacc cttttagtca    7740
gtgtggaaaa tctctagcag tagtagttca tgtcatctta ttattcagta tttataactt    7800
gcaaagaaat gaatatcaga gagtgagagg aacttgttta ttgcagctta taatggttac    7860
aaataaagca atagcatcac aaatttcaca aataaagcat ttttttcact gcattctagt    7920
tgtggtttgt ccaaactcat caatgtatct tatcatgtct ggctctagct atcccgcccc    7980
taactccgcc cagttccgcc cattctccgc cccatggctg actaatttt tttatttatg    8040
```

```
cagaggccga ggccgcctcg gcctctgagc tattccagaa gtagtgagga ggcttttttg    8100
gaggcctagg cttttgcgtc gagacgtacc caattcgccc tatagtgagt cgtattacgc    8160
gcgctcactg gccgtcgttt tacaacgtcg tgactgggaa aaccctggcg ttacccaact    8220
taatcgcctt gcagcacatc ccccttcgc cagctggcgt aatagcgaag aggcccgcac     8280
cgatcgccct tcccaacagt tgcgcagcct gaatggcgaa tggcgcgacg cgcctgtag     8340
cggcgcatta agcgcggcgg gtgtggtggt tacgcgcagc gtgaccgcta cacttgccag    8400
cgccctagcg cccgctcctt tcgctttctt cccttccttt ctcgccacgt tcgccggctt    8460
tccccgtcaa gctctaaatc gggggctccc tttagggttc cgatttagtg ctttacggca    8520
cctcgacccc aaaaaacttg attagggtga tggttcacgt agtgggccat cgccctgata    8580
gacggttttt cgccctttga cgttggagtc cacgttcttt aatagtggac tcttgttcca    8640
aactggaaca cactcaacc ctatctcggt ctattctttt gatttataag ggattttgcc     8700
gatttcggcc tattggttaa aaatgagct gatttaacaa aaatttaacg cgaattttaa     8760
caaaatatta acgtttacaa tttcccaggt ggcactttc ggggaaatgt gcgcggaacc     8820
cctatttgtt tatttttcta aatacattca aatatgtatc cgctcatgag acaataaccc    8880
tgataaatgc ttcaataata ttgaaaaagg aagagtatga gtattcaaca tttccgtgtc    8940
gcccttattc ccttttttgc ggcattttgc cttcctgttt ttgctcaccc agaaacgctg    9000
gtgaaagtaa aagatgctga agatcagttg ggtgcacgag tgggttacat cgaactggat    9060
ctcaacagcg gtaagatcct tgagagtttt cgccccgaag aacgttttcc aatgatgagc    9120
acttttaaag ttctgctatg tggcgcggta ttatcccgta ttgacgccgg gcaagagcaa    9180
ctcggtcgcc gcatacacta ttctcagaat gacttggttg agtactcacc agtcacagaa    9240
aagcatctta cggatggcat gacagtaaga gaattatgca gtgctgccat aaccatgagt    9300
gataacactg cggccaactt acttctgaca acgatcggag gaccgaagga gctaaccgct    9360
tttttgcaca acatggggga tcatgtaact cgccttgatc gttgggaacc ggagctgaat    9420
gaagccatac caaacgacga gcgtgacacc acgatgcctg tagcaatggc aacaacgttg    9480
cgcaaactat taactggcga actacttact ctagcttccc ggcaacaatt aatagactgg    9540
atggaggcgg ataaagttgc aggaccactt ctgcgctcgg cccttccggc tggctggttt    9600
attgctgata atctggagcc ggtgagcgt gggtctcgcg gtatcattgc agcactgggg     9660
ccagatggta agccctcccg tatcgtagtt atctacacga cggggagtca ggcaactatg    9720
gatgaacgaa atagacagat cgctgagata ggtgcctcac tgattaagca ttggtaactg    9780
tcagaccaag tttactcata tatactttag attgatttaa aacttcattt ttaatttaaa    9840
aggatctagg tgaagatcct ttttgataat ctcatgacca aaatccctta acgtgagttt    9900
tcgttccact gagcgtcaga ccccgtagaa aagatcaaag gatcttcttg agatcctttt    9960
tttctgcgcg taatctgctg cttgcaaaca aaaaaaccac cgctaccagc ggtggtttgt    10020
ttgccggatc aagagctacc aactctttt ccgaaggtaa ctggcttcag cagagcgcag    10080
ataccaaata ctgtccttct agtgtagccg tagttaggcc accacttcaa gaactctgta    10140
gcaccgccta catacctcgc tctgctaatc ctgttaccag tggctgctgc cagtggcgat    10200
aagtcgtgtc ttaccgggtt ggactcaaga cgatagttac cggataaggc gcagcggtcg    10260
ggctgaacgg ggggttcgtg cacacagccc agcttggagc gaacgaccta caccgaactg    10320
agatacctac agcgtgagct atgagaaagc gccacgcttc ccgaagggag aaaggcggac    10380
```

| | |
|---|---:|
| aggtatccgg taagcggcag ggtcggaaca ggagagcgca cgagggagct tccaggggga | 10440 |
| aacgcctggt atctttatag tcctgtcggg tttcgccacc tctgacttga gcgtcgattt | 10500 |
| ttgtgatgct cgtcaggggg gcggagccta tggaaaaacg ccagcaacgc ggcctttta | 10560 |
| cggttcctgg ccttttgctg ccttttgct cacatgttct ttcctgcgtt atcccctgat | 10620 |
| tctgtggata accgtattac cgcctttgag tgagctgata ccgctcgccg cagccgaacg | 10680 |
| accgagcgca gcgagtcagt gagcgaggaa gcggaagagc gcccaatacg caaaccgcct | 10740 |
| ctccccgcgc gttggccgat tcattaatgc agctggcacg acaggtttcc cgactggaaa | 10800 |
| gcgggcagtg agcgcaacgc aattaatgtg agttagctca ctcattaggc accccaggct | 10860 |
| ttacactta tgcttccggc tcgtatgttg tgtggaattg tgagcggata acaatttcac | 10920 |
| acaggaaaca gctatgacca tgattacgcc aagcgcgcaa ttaaccctca ctaaagggaa | 10980 |
| caaaagctgg agctgca | 10997 |

<210> SEQ ID NO 8
<211> LENGTH: 11035
<212> TYPE: DNA
<213> ORGANISM: Artificial Sequence
<220> FEATURE:
<223> OTHER INFORMATION: lentiviral vector vivo-TIL 106 - TCP2

<400> SEQUENCE: 8

| | |
|---|---:|
| agcttaatgt agtcttatgc aatactcttg tagtcttgca acatggtaac gatgagttag | 60 |
| caacatgcct tacaaggaga gaaaaagcac cgtgcatgcc gattggtgga agtaaggtgg | 120 |
| tacgatcgtg ccttattagg aaggcaacag acgggtctga catggattgg acgaaccact | 180 |
| gaattgccgc attgcagaga tattgtattt aagtgcctag ctcgatacaa taaacgggtc | 240 |
| tctctggtta gaccagatct gagcctggga gctctctggc taactaggga acccactgct | 300 |
| taagcctcaa taaagcttgc cttgagtgct tcaagtagtg tgtgcccgtc tgttgtgtga | 360 |
| ctctggtaac tagagatccc tcagacccct ttagtcagtg tggaaaatct ctagcagtgg | 420 |
| cgcccgaaca gggacttgaa agcgaaaggg aaaccagagg agctctctcg acgcaggact | 480 |
| cggcttgctg aagcgcgcac ggcaagaggc gaggggcggc gactggtgag tacgccaaaa | 540 |
| attttgacta gcggaggcta agaggagaga gatgggtgcg agagcgtcag tattaagcgg | 600 |
| gggagaatta gatcgcgatg ggaaaaaatt cggttaaggc cagggggaaa gaaaaaatat | 660 |
| aaattaaaac atatagtatg ggcaagcagg gagctagaac gattcgcagt taatcctggc | 720 |
| ctgttagaaa catcagaagg ctgtagacaa atactgggac agctacaacc atcccttcag | 780 |
| acaggatcag aagaacttag atcattatat aatacagtag caaccctcta ttgtgtgcat | 840 |
| caaaggatag agataaaaga caccaaggaa gctttagaca agatagagga agagcaaaac | 900 |
| aaaagtaaga ccaccgcaca gcaagcggcc gctgatcttc agacctggag gaggagatat | 960 |
| gagggacaat tggagaagtg aattatataa atataaagta gtaaaattg aaccattagg | 1020 |
| agtagcaccc accaaggcaa agagaagagt ggtgcagaga gaaaaaagag cagtgggaat | 1080 |
| aggagctttg ttccttgggt tcttgggagc agcaggaagc actatgggcg cagcctcaat | 1140 |
| gacgctgacg gtacaggcca gacaattatt gtctggtata gtgcagcagc agaacaattt | 1200 |
| gctgagggct attgaggcgc aacagcatct gttgcaactc acagtctggg gcatcaagca | 1260 |
| gctccaggca agaatcctgg ctgtggaaag ataccttaaag gatcaacagc tcctggggat | 1320 |
| ttggggttgc tctggaaaac tcatttgcac cactgctgtg ccttggaatg ctagttggag | 1380 |
| taataaatct ctggaacaga tttggaatca cacgacctgg atggagtggg acagagaaat | 1440 |

```
taacaattac acaagcttaa tacactcctt aattgaagaa tcgcaaaacc agcaagaaaa    1500
gaatgaacaa gaattattgg aattagataa atgggcaagt ttgtggaatt ggtttaacat    1560
aacaaattgg ctgtggtata taaaattatt cataatgata gtaggaggct tggtaggttt    1620
aagaatagtt tttgctgtac tttctatagt gaatagagtt aggcagggat attcaccatt    1680
atcgtttcag acccacctcc caaccccgag gggacccgac aggcccgaag gaatagaaga    1740
agaaggtgga gagagagaca gagacagatc cattcgatta gtgaacggat ctcgacggta    1800
tcggttaact tttaaaagaa aagggggggat tgggggggtac agtgcagggg aaagaatagt    1860
agacataata gcaacagaca tacaaactaa agaattacaa aaacaaatta caaaaattca    1920
aaattttatc gatcacgaga ctagcctcga gaagcttgat atcgaattcc cacggggttg    1980
gacgcgtaga caatactttg gtataaattt gggattaatt cgaaagttct tgattgtaaa    2040
taataaactt tccccaagaa aaggagtacg atgaactttc tttaagaaaa aaaaaaaaaa    2100
tccaatgcat ttcacatgac caaggattgc acagatgcat ttctggacca aggaggagaa    2160
gattgaacgt tggagggggg ctgcccgtct gacttcctca cctgttcgag ggggtcggga    2220 agggggggtta ccgctaagtc atcactttttt tatgtgtgtc ggttaaaact acaaaggcaa    2280
ccaaaaggag gtcttatccg ttttttgtga gcttcagttg ggagcagcag gtagaagaag    2340
ctgcactctg gttttacttt ttcaccaccg ggacctataa atagatgagg ctgtgtggct    2400
ttctcgctga gttacctcca ccttcttgcc tgggacctca cgatccaggc ggctctaact    2460
cccacatgaa cattcgcagc tcactgcccc cgcagtcatt ttccacaaca tgtgtgtgac    2520
atgaagaagt gcgtctcagc atggtgtgtt tgtgtgtgtt gttgttatttt ttgttttagc    2580 gttgagttct agatgtcttc cgcccacact gccaactctg gaagcaaggc tttctaaatg    2640
tctcgaagag gtcctcgata tttgttgaag gaagaaaaca ttgctcttgg ttattttttgc    2700 tccccatgta tccaaaaata cactaacttt tatgtttcat aactattcaa tactagtccc    2760
tcggccgctc ttacatgatg atgtacagtg tttatctgcc aggccgcgtt ttgtacaaac    2820
tgcctttact ctccccaact atttggtaaa gaaaattatt ttcacttttt ttgttgttgt    2880
tgtttgtttt tgtttgtttt gagagggaat attgctctgt tgccaggctg gagtgcagtg    2940
gagtgatctc ggcttactgc aacctccacc tcccgggttc aagcgattct cctgcctcag    3000
cctcctgagt cactgggatt acaggcgtgc gccaacacac acagctaatt tttgtatttt    3060
tagtagagct ggggtttcac catgttggcc aggatgatct caatctcctg acctcgtgat    3120
ctgcccgctt cagcctccca aagtgctggg attacaggcg tgagccaccg cgcccggcct    3180
attttcactt ttagtaaatg gaaatctggg tatcaagaga agtcagtttc tattttttct    3240
tggccctacc tccaaaatat ttccagatct ccctagcctg cacacccttg ccacctgtca    3300
ttcccacttg gaccaggcca gcagcctccc tggtctctct gaccctcccc ctgagttcgt    3360
tcaccaaagg cagtaacgga gacacccccct caacacacac aggaagcaga tggccttgac    3420
accagcaggg tgacatccgc tattgctact tctctgctcc cccacagttc ctctggactt    3480
ctctggacca cagtcctctg ccagacccct gccagacccc agtccaccgc tagcaccggt    3540
gccgccacca tgcctctggg cctgctgtgg ctgggcctgg cctgctgggc gccctgcac    3600 gcccaggccg gcgtgcaggt ggagacaatc tccccaggcg acggacgcac attccctaag    3660
cggggccaga cctgcgttgt gcactataca ggcatgctgg aggatggcaa gaagtttgac    3720
agctcccggg atagaaacaa gccattcaag tttatgctgg gcaagcagga agtgatcaga    3780
```

```
ggctgggagg agggcgtggc ccagatgtct gtgggccaga gggccaagct gaccatcagc    3840
ccagactacg cctatggagc aacaggccac ccaggaatca tcccacctca cgccaccctg    3900
gtgttcgatg tggagctgct gaagctgggc gagggatcca acacatcaaa agagaacccc    3960
tttctgttcg cattggaggc cgtagtcata tctgttggat ccatgggact tattatctcc    4020
ctgttgtgtg tgtacttctg gctggaacgg actatgccca ggatcccccac gctcaagaat    4080 ctggaagatc tcgtcacaga ataccatggt aatttcagcg cctggagcgg agtctctaag    4140
ggtctggccg aatccctcca acccgattat tctgaacggt tgtgcctcgt atccgaaata    4200
ccaccaaaag gcggggctct gggtgagggc caggggcga gtccgtgcaa tcaacacagc    4260
ccgtattggg cccctccttg ttatacgttg aagcccgaaa ctggaagcgg agctactaac    4320
ttcagcctgc tgaagcaggc tggagacgtg aggagaacc ctggacctat ggcactgccc    4380
gtgaccgccc tgctgctgcc tctggccctg ctgctgcacg cagcccggcc tatcctgtgg    4440
cacgagatgt ggcacgaggg cctggaggag ccagcaggc tgtattttgg cgagcgcaac    4500
gtgaagggca tgttcgaggt gctggagcct ctgcacgcca tgatggagag aggcccacag    4560
accctgaagg agacatcctt taaccaggcc tatgacgggg acctgatgga ggcacaggag    4620
tggtgcagaa agtacatgaa gtctggcaat gtgaaggacc tgctgcaggc tgggatctg    4680 tactatcacg tgtttcggag aatctccaag ggcaaagaca cgattccgtg gcttgggcat    4740
ctgctcgttg ggctgagtgg tgcgtttggt ttcatcatct tggtctatct cttgatcaat    4800
tgcagaaata caggcccttg gctgaaaaaa gtgctcaagt gtaataccccc cgacccaagc    4860 aagttcttct cccagctttc ttcagagcat ggaggcgatg tgcagaaatg gctctcttca    4920
ccttttccct cctcaagctt ctccccggga gggctggcgc ccgagatttc acctcttgag    4980
gtacttgaac gagacaaggt tacccaactt ctccttcaac aggataaggt acccgaacct    5040
gcgagcctta gctccaacca ctctcttacg agctgcttca ccaatcaggg atacttcttt    5100
ttccaccttc ccgatgcgct ggaaatcgaa gcttgtcaag tttactttac ctatgatcca    5160
tatagcgagg aagatcccga cgaaggagtc gccggtgcgc ccacgggttc ctcaccccaa    5220
cctctccagc ctctctcagg agaagatgat gcttattgca cttttcccag tagagacgat    5280
ctcctcctct tttctccatc tcttttgggg gaccttccc ccccttctac ggcacctggc    5340
gggtctggtg ctggcgagga gcggatgccg ccgtccctcc aggagcgagt accacgagat    5400
tgggatcccc agccacttgg acccccccacc cccggcgtac ctgaccttgt cgattttcaa    5460 cctcccctg aattggtgct gcgagaggct ggggaggaag ttccggacgc tgggccgagg    5520
gagggcgtgt ccttttccatg gagtaggcct ccaggtcaag gcgagtttag ggctctcaac    5580
gcgcggctgc cgttgaatac agacgcttat ctctcactgc aggaactgca aggtcaggac    5640
ccaacacatc ttgtaggatc tggtgctact aattttttctc ttttgaagca agctggagat    5700
gttgaagaga accccggtcc ggagatgtgg catgagggtc tggaagaagc gtctcgactg    5760
tactttggtg agcgcaatgt gaagggcatg tttgaagtcc tcgaacccct tcatgccatg    5820
atggaacgcg accccagac cttgaaggag acaagtttta accaagctta cggaagagac    5880
ctgatgaaag cccaggaatg tgtgcaggaaa tacatgaaaa gcgggaatgt gaaggacttg    5940
ctccaagcgt gggacctgta ctatcatgtc tttaggcgca ttagtaaggg cagcggcgcc    6000
accaacttca gcctgctgaa gcaggccggc gacgtggagg agaaccccgg ccccggtgct    6060
ggcgcaactg gacgcgctat ggatggacct cgcttgctgc ttcttctgct tctcggggtc    6120 tcttttgggtg gtgctaagga agcatgccca acgggacttt atacgcatag cggagagtgt    6180
```

```
tgcaaagctt gtaacctggg cgaaggcgtc gcgcaacctt gtggtgcaaa tcaaaccgtc   6240
tgcgagccat gtttggactc tgttacgttt agtgacgtag tatctgcgac agagccatgc   6300
aagccttgta cggaatgtgt aggattgcag agcatgtctg ccccttgtgt agaagccgac   6360
gatgcagttt gcaggtgcgc gtatggctat taccaagacg aaacaaccgg acgatgtgaa   6420
gcttgccgag tttgtgaagc gggttccggg cttgtattct cctgtcagga taagcagaac   6480
accgtctgcg aagagtgccc cgatggtacc tacagcgatg aagcgaacca tgtagaccca   6540
tgcctgcctt gcaccgtttg tgaagacacg aacgacagt tgcgggaatg tacccggtgg   6600
gcagacgccg agtgcgaaga gattccaggc cgctggatca cgcgaagtac cccgccagaa   6660
ggttccgaca gtactgcacc aagcacccaa gaaccagagg cgcccccga gcaggacctg   6720 attgcctcca ccgtggcggg tgttgttact acggttatgg gctcatccca gcccgttgtt   6780
acccgaggaa ctacagacaa cctgattccg gtatattgtt ctatcttggc ggctgtagta   6840
gttggcttgg tcgcgtacat cgcttttcaaa agatgaacta gtgtcgacaa tcaacctctg   6900
gattacaaaa tttgtgaaag attgactggt attcttaact atgttgctcc ttttacgcta   6960
tgtggatacg ctgctttaat gccttttgtat catgctattg cttcccgtat ggctttcatt   7020
ttctcctcct tgtataaatc ctggttgctg tctctttatg aggagttgtg gcccgttgtc   7080
aggcaacgtg gcgtggtgtg cactgtgttt gctgacgcaa ccccccactgg ttggggcatt   7140 gccaccacct gtcagctcct ttccgggact ttcgctttcc ccctccctat gccacggcg    7200 gaactcatcg ccgcctgcct tgcccgctgc tggacagggg ctcggctgtt gggcactgac   7260
aattccgtgg tgttgtcggg gaagctgacg tcctttccat ggctgctcgc ctgtgttgcc   7320
acctggattc tgcgcgggac gtccttctgc tacgtccctt cggccctcaa tccagcggac   7380
cttccttccc gcggcctgct gccggctctg cggcctcttc cgcgtcttcg ccttcgccct   7440
cagacgagtc ggatctccct ttgggccgcc tccccgcctg gaattcgagc tcggtacctt   7500
taagaccaat gacttacaag gcagctgtag atcttagcca cttttaaaa gaaaaggggg   7560 gactggaagg gctaattcac tcccaacgaa gacaagatct gcttttttgct tgtactgggt   7620 ctctctggtt agaccagatc tgagcctggg agctctctgg ctaactaggg aacccactgc   7680
ttaagcctca ataaagcttg ccttgagtgc ttcaagtagt gtgtgcccgt ctgttgtgtg   7740
actctggtaa ctagagatcc ctcagaccct tttagtcagt gtggaaaatc tctagcagta   7800
gtagttcatg tcatcttatt attcagtatt tataacttgc aaagaaatga atatcagaga   7860
gtgagaggaa cttgttttatt gcagcttata atggttacaa ataaagcaat agcatcacaa   7920
atttcacaaa taaagcattt ttttcactgc attctagttg tggtttgtcc aaactcatca   7980
atgtatctta tcatgtctgg ctctagctat cccgcccta actccgccca gttccgccca   8040
ttctccgccc catggctgac taattttttt tatttatgca gaggccgagg ccgcctcggc   8100
ctctgagcta ttccagaagt agtgaggagg ctttttgga ggcctaggct tttgcgtcga   8160
gacgtaccca attcgcccta tagtgagtcg tattacgcgc gctcactggc cgtcgtttta   8220
caacgtcgtg actgggaaaa ccctggcgtt acccaactta atcgccttgc agcacatccc   8280
cctttcgcca gctggcgtaa tagcgaagag gcccgcaccg atcgcccttc ccaacagttg   8340
cgcagcctga atggcgaatg gcgcgacgcg ccctgtagcg gcgcattaag cgcggcgggt   8400
gtggtggtta cgcgcagcgt gaccgctaca cttgccagcg ccctagcgcc cgctcctttc   8460
gctttcttcc cttcctttct cgccacgttc gccggctttc cccgtcaagc tctaaatcgg   8520
```

```
gggctcccctt tagggttccg atttagtgct ttacggcacc tcgaccccaa aaaacttgat    8580
tagggtgatg gttcacgtag tgggccatcg ccctgataga cggttttcg ccctttgacg     8640 ttggagtcca cgttctttaa tagtggactc ttgttccaaa ctggaacaac actcaaccct    8700
atctcggtct attcttttga tttataaggg attttgccga tttcggccta ttggttaaaa    8760
aatgagctga tttaacaaaa atttaacgcg aattttaaca aaatattaac gtttacaatt    8820
tcccaggtgg cacttttcgg ggaaatgtgc gcggaacccc tatttgttta ttttctaaa    8880 tacattcaaa tatgtatccg ctcatgagac aataaccctg ataaatgctt caataatatt    8940 gaaaaggaa gagtatgagt attcaacatt tccgtgtcgc ccttattccc ttttttgcgg     9000
cattttgcct tcctgttttt gctcacccag aaacgctggt gaaagtaaaa gatgctgaag    9060
atcagttggg tgcacgagtg ggttacatcg aactggatct caacagcggt aagatccttg    9120
agagttttcg ccccgaagaa cgttttccaa tgatgagcac ttttaaagtt ctgctatgtg    9180
gcgcggtatt atcccgtatt gacgccgggc aagagcaact cggtcgccgc atacactatt    9240
ctcagaatga cttggttgag tactcaccag tcacagaaaa gcatcttacg gatggcatga    9300
cagtaagaga attatgcagt gctgccataa ccatgagtga taacactgcg gccaacttac    9360
ttctgacaac gatcggagga ccgaaggagc taaccgcttt tttgcacaac atggggggatc   9420 atgtaactcg ccttgatcgt tgggaaccgg agctgaatga agccatacca aacgacgagc    9480
gtgacaccac gatgcctgta gcaatggcaa caacgttgcg caaactatta actggcgaac    9540
tacttactct agcttcccgg caacaattaa tagactggat ggaggcggat aaagttgcag    9600
gaccacttct gcgctcggcc cttccggctg gctggtttat tgctgataaa tctggagccg    9660
gtgagcgtgg gtctcgcggt atcattgcag cactggggcc agatggtaag ccctcccgta    9720
tcgtagttat ctacacgacg gggagtcagg caactatgga tgaacgaaat agacagatcg    9780
ctgagatagg tgcctcactg attaagcatt ggtaactgtc agaccaagtt tactcatata    9840
tactttagat tgatttaaaa cttcattttt aatttaaaag gatctaggtg aagatccttt    9900
ttgataatct catgaccaaa atcccttaac gtgagttttc gttccactga gcgtcagacc    9960
ccgtagaaaa gatcaaagga tcttcttgag atcctttttt tctgcgcgta atctgctgct   10020
tgcaaacaaa aaaaccaccg ctaccagcgg tggtttgttt gccggatcaa gagctaccaa   10080
ctctttttcc gaaggtaact ggcttcagca gagcgcagat accaaatact gtccttctag   10140
tgtagccgta gttaggccac cacttcaaga actctgtagc accgcctaca tacctcgctc   10200
tgctaatcct gttaccagtg gctgctgcca gtggcgataa gtcgtgtctt accgggttgg   10260
actcaagacg atagttaccg gataaggcgc agcggtcggg ctgaacgggg ggttcgtgca   10320
cacagcccag cttggagcga acgacctaca ccgaactgag atacctacag cgtgagctat   10380
gagaaagcgc cacgcttccc gaagggagaa aggcggacag gtatccggta agcggcaggg   10440
tcggaacagg agagcgcacg agggagcttc caggggaaa cgcctggtat ctttatagtc    10500
ctgtcgggtt tcgccacctc tgacttgagc gtcgattttt gtgatgctcg tcaggggggc    10560
ggagcctatg gaaaaacgcc agcaacgcgg ccttttacg gttcctggcc ttttgctggc     10620
cttttgctca catgttcttt cctgcgttat cccctgattc tgtggataac cgtattaccg    10680
cctttgagtg agctgatacc gctcgccgca gccgaacgac cgagcgcagc gagtcagtga   10740
gcgaggaagc ggaagagcgc ccaatacgca aaccgcctct ccccgcgcgt tggccgattc   10800
attaatgcag ctggcacgac aggtttcccg actggaaagc gggcagtgag cgcaacgcaa   10860
ttaatgtgag ttagctcact cattaggcac cccaggcttt acactttatg cttccggctc   10920
```

```
gtatgttgtg tggaattgtg agcggataac aatttcacac aggaaacagc tatgaccatg    10980
attacgccaa gcgcgcaatt aaccctcact aaagggaaca aaagctggag ctgca         11035
```

<210> SEQ ID NO 9
<211> LENGTH: 11912
<212> TYPE: DNA
<213> ORGANISM: Artificial Sequence
<220> FEATURE:
<223> OTHER INFORMATION: lentiviral vector vivo-TIL 107 - TCP3

<400> SEQUENCE: 9

```
agcttaatgt agtcttatgc aatactcttg tagtcttgca acatggtaac gatgagttag      60
caacatgcct tacaaggaga gaaaaagcac cgtgcatgcc gattggtgga gtaaggtgg     120 tacgatcgtg ccttattagg aaggcaacag acgggtctga catggattgg acgaaccact     180
gaattgccgc attgcagaga tattgtattt aagtgcctag ctcgatacaa taaacgggtc     240
tctctggtta gaccagatct gagcctggga gctctctggc taactaggga acccactgct     300
taagcctcaa taaagcttgc cttgagtgct tcaagtagtg tgtgcccgtc tgttgtgtga     360
ctctggtaac tagagatccc tcagaccctt ttagtcagtg tggaaaatct ctagcagtgg     420
cgcccgaaca gggacttgaa agcgaaaggg aaaccagagg agctctctcg acgcaggact     480
cggcttgctg aagcgcgcac ggcaagaggc gaggggcggc gactggtgag tacgccaaaa     540
attttgacta gcggaggcta aaggagaga gatgggtgcg agagcgtcag tattaagcgg     600
gggagaatta gatcgcgatg ggaaaaaatt cggttaaggc caggggggaaa gaaaaaatat     660 aaattaaaac atatagtatg ggcaagcagg gagctagaac gattcgcagt taatcctggc     720
ctgttagaaa catcagaagg ctgtagacaa atactgggac agctacaacc atcccttcag     780
acaggatcag aagaacttag atcattatat aatacagtag caaccctcta ttgtgtgcat     840
caaaggatag agataaaaga caccaaggaa gctttagaca agatagagga gagcaaaac     900 aaaagtaaga ccaccgcaca gcaagcggcc gctgatcttc agacctggag gaggagatat     960
gagggacaat tggagaagtg aattatataa atataaagta gtaaaaattg aaccattagg    1020
agtagcaccc accaaggcaa agagaagagt ggtgcagaga gaaaaaagag cagtgggaat    1080
aggagctttg ttccttgggt tcttgggagc agcaggaagc actatgggcg cagcctcaat    1140
gacgctgacg gtacaggcca gacaattatt gtctggtata gtgcagcagc agaacaattt    1200
gctgagggct attgaggcgc aacagcatct gttgcaactc acagtctggg gcatcaagca    1260
gctccaggca agaatcctgg ctgtggaaag atacctaaag gatcaacagc tcctggggat    1320
ttggggttgc tctggaaaac tcatttgcac cactgctgtg ccttggaatg ctagttggag    1380
taataaatct ctggaacaga tttggaatca cacgacctgg atggagtggg acagagaaat    1440
taacaattac acaagcttaa tacactcctt aattgaagaa tcgcaaaacc agcaagaaaa    1500
gaatgaacaa gaattattgg aattagataa atggcaagt ttgtggaatt ggtttaacat    1560
aacaaattgg ctgtggtata taaaattatt cataatgata gtaggaggct tggtaggttt    1620
aagaatagtt tttgctgtac tttctatagt gaatagagtt aggcagggat attcaccatt    1680
atcgtttcag acccacctcc caaccccgag gggacccgac aggcccgaag gaatagaaga    1740
agaaggtgga gagagagaca gagacagatc cattcgatta gtgaacggat ctcgacggta    1800
tcggttaact tttaaagaa aaggggggat tggggggtac agtgcagggg aaagaatagt    1860
agacataata gcaacagaca tacaaactaa agaattacaa aaacaaatta caaaaattca    1920
```

```
aaatttatc gatcacgaga ctagcctcga gaagcttgat atcgaattcc cacggggttg      1980
gacgcgtaga gctttgacta gacccgtgtc tgctcattgt gtgaaggatc ccagtgtcga      2040
ggagaggaag ctgccgaata agaaagagcc tcgctggtgt gacagcagga tcaaattcag      2100
tcaactcaat ccggctgaga cctccttagt cctcaccaga atgacccgaa catgctcccc      2160
aggtctcagc tgcaaagctg ggtccaacaa cctatttgta gatttccata atgaattaaa      2220
gcctccatgc acaaacgtta acaggagtca ccagaaaact taacatttta ggtcttactt      2280
tcttgactgt tcagacacgg tcataatgac ctgtactgtc atccttcaaa acaagggaat      2340
ctatggatac tggaggtgtc atgaactcat cagatgacat acaaaaagat aggctaagag      2400
acaactcagt tgaatcaaat cttaagtgtc ttaaatgact atgattaaaa ggtcagaccc      2460
catccccagc tagcagtcat gcagctgtac tttgagggaa gtggggagaa aaaaatagtt      2520
ttcagttaga gttctaaaac aataggtggt gagaaggcac ctgctttgaa atgctggtgc      2580
cttgtctgtg gtcctgtctg cccgccttct ccttggcttc ttagacttgc taaaccttgt      2640
tacactctgg caggaagctc tgagggctaa accacaaaaa ctaagtacat tcaggacttc      2700
ctgtgacagc tcactgagga ttgaactact ttttcctctg aatctgagag tctatttttc      2760
cagcaaccag agttaattac taagggcaat gatgaatgaa acctcatcgc ctcccaaaat      2820
tcaaacacaa aatccagcta ggtaacaatt gccacaggat ctacccagta gagagatgag      2880
ggctctggcc gggcatggtg gctcgtgcca gtaatcctaa cactttggga ggccaaagca      2940
ggtagatcac ctgaggtcag gagtttgaga ccagcctggc caacatggtg aaaccccttc      3000
tctacttaaa aaaaaaaaaa aaaaaattag ccgggcatcg tggcacgcac ctataacccc      3060
agctactcgg gaggttgagg cagaataatt gcttgaaccc tggggtgtgg aggttgcagt      3120
gaggtgagat cgtgtcactt cgctctagcc tgggcaaaag agcaaaactc cgtctaaaaa      3180
aaaaaaggag agagagagag agagagagag agagatgagg gtcctagctc tgcccctttc      3240
tcattcttca tgatacccat gagtgatttc attggctatc tcaccagaac agctcatacg      3300
ccattccctt aagaaaatct tccctggtct attcagccct gggctctgcc tttcttctga      3360
actcctgtgg cattacatat ggtacaaaac acatacaccc tattcaatcc ttcatcgttc      3420
attcattcaa cgaacattta ttgaacttct actatgtgtc aggctctgtg ctaggcacta      3480
ggaaaacaga ggtgtacaat tgcatctctg ctttcaagga gctcaccacc tggtaggcaa      3540
gaaacggacc aaccatggga caaatgcaat gcagtatgat aaatataggt cagaggcaag      3600
tgcatgaacc cagaggaagg actttgaacc cagactgagt ggtaagactg gggtgacaaa      3660
gagggcttcc tagaggaggg acgtttgggt tgcgttgtaa tagattaatt gaactggtga      3720
agcagaggta cagaattacc catgtagagg caacagcatg agcaaggctc atttggcttt      3780
ctgtttacac aaacatgtag tttctttttc aactactgta tttaactgat ttgaagatgt      3840
cattgatttt tcaactactg ttttcaactt tttgtatttc ttttctttt ttaacaacta      3900 tatttaacta atttgaagat ggcattgatt ttaagtggca tcattctttt acatgccact      3960
aagaaagaga agaacacttc tcagttgcat tgtaacaaat actaagatac agtcaacttt      4020
cagtcacaat cccattcctg agatattaaa atgtgaaaaa atgttatttt atgttagtgc      4080 atttttagaat tgatgaaatg catagtaaag atttttcttgg ccctacctcc aaaatatttc      4140
cagatctccc tagcctgcac acccttgcca cctgtcattc ccacttggac caggccagca      4200
gcctccctgg tctctctgac cctcccctg agttcgttca ccaaaggcag taacggagac      4260
accccctcaa cacacacagg aagcagatgg ccttgacacc agcagggtga catccgctat      4320
```

```
tgctacttct ctgctccccc acagttcctc tggacttctc tggaccacag tcctctgcca    4380 gaccccctgcc agaccccagt ccaccgctag caccggtgcc gccaccatgc ctctgggcct    4440
gctgtggctg ggcctggccc tgctgggcgc cctgcacgcc caggccggcg tgcaggtgga    4500
gacaatctcc ccaggcgacg gacgcacatt ccctaagcgg ggccagacct gcgttgtgca    4560
ctatacaggc atgctggagg atggcaagaa gtttgacagc tcccgggata gaaacaagcc    4620
attcaagttt atgctgggca agcaggaagt gatcagaggc tgggaggagg cgtggcccca    4680
gatgtctgtg ggccagaggg ccaagctgac catcagccca gactacgcct atggagcaac    4740
aggccaccca ggaatcatcc cacctcacgc caccctggtg ttcgatgtgg agctgctgaa    4800
gctgggcgag ggatccaaca catcaaaaga gaaccccttt ctgttcgcat ggaggccgt    4860 agtcatatct gttggatcca tgggacttat tatctccctg ttgtgtgtgt acttctggct    4920
ggaacggact atgcccagga tccccacgct caagaatctg aagatctcg tcacagaata    4980 ccatggtaat ttcagcgcct ggagcggagt ctctaagggt ctggccgaat ccctccaacc    5040
cgattattct gaacggttgt gcctcgtatc cgaaatacca ccaaaaggcg gggctctggg    5100
tgagggccca ggggcgagtc cgtgcaatca acacagcccg tattgggccc ctccttgtta    5160
tacgttgaag cccgaaactg gaagcggagc tactaacttc agcctgctga agcaggctgg    5220
agacgtggag gagaaccctg gacctatggc actgccccgtg accgccctgc tgctgcctct    5280
ggccctgctg ctgcacgcag cccggcctat cctgtggcac gagatgtggc acgagggcct    5340
ggaggaggcc agcaggctgt attttggcga gcgcaacgtg aagggcatgt tcgaggtgct    5400
ggagcctctg cacgccatga tggagagagg cccacagacc ctgaaggaga catcctttaa    5460
ccaggcctat ggacgggacc tgatggaggc acaggagtgg tgcagaaagt acatgaagtc    5520
tggcaatgtg aaggacctgc tgcaggcctg ggatctgtac tatcacgtgt tcggagaat    5580 ctccaagggc aaagacacga ttccgtggct tgggcatctg ctcgttgggc tgagtggtgc    5640
gtttggtttc atcatcttgg tctatctctt gatcaattgc agaaatacag gcccttggct    5700
gaaaaaagtg ctcaagtgta taccccccga cccaagcaag ttcttctccc agctttcttc    5760
agagcatgga ggcgatgtgc agaaatggct ctcttcacct ttccctcct caagcttctc    5820 cccgggaggg ctggcgcccg agatttcacc tcttgaggta cttgaacgag acaaggttac    5880
ccaacttctc cttcaacagg ataaggtacc cgaacctgcg agcctagct ccaaccactc    5940 tcttacgagc tgcttcacca atcagggata cttcttttt caccttcccg atgcgctgga    6000
aatcgaagct tgtcaagttt actttaccta tgatccatat agcgaggaag atcccgacga    6060
aggagtcgcc ggtgcgccca cgggttcctc accccaacct ctccagcctc tctcaggaga    6120
agatgatgct tattgcactt ttcccagtag agacgatctc ctcctctttt ctccatctct    6180
tttgggggga ccttccccc cttctacggc acctggcggg tctggtgctg gcgaggagcg    6240
gatgccgccg tccctccagg agcgagtacc acgagattgg atcccccagc acttggacc    6300 ccccaccccc ggcgtacctg accttgtcga ttttcaacct cccctgaat tggtgctgcg    6360 agaggctggg gaggaagttc cggacgctgg gccgagggag ggcgtgtcct ttccatggag    6420
taggcctcca ggtcaaggcg agtttaggc tctcaacgcg cggctgccgt tgaatacaga    6480
cgcttatctc tcactgcagg aactgcaagg tcaggaccca acacatcttg taggatctgg    6540
tgctactaat ttttctcttt tgaagcaagc tggagatgtt gaagagaacc ccggtccgga    6600
gatgtggcat gagggtctgg aagaagcgtc tcgactgtac tttggtgagc gcaatgtgaa    6660
```

-continued

```
gggcatgttt gaagtcctcg aaccccttca tgccatgatg aacgcggac cccagacctt    6720 gaaggagaca agttttaacc aagcttacgg aagagacctg atggaagccc aggaatggtg    6780
caggaaatac atgaaaagcg ggaatgtgaa ggacttgctc caagcgtggg acctgtacta    6840
tcatgtcttt aggcgcatta gtaagggcag cggcgccacc aacttcagcc tgctgaagca    6900
ggccggcgac gtggaggaga accccggccc cggtgctggc gcaactggac gcgctatgga    6960
tggacctcgc ttgctgcttc ttctgcttct cggggtctct ttgggtggtg ctaaggaagc    7020
atgcccaacg ggactttata cgcatagcgg agagtgttgc aaagcttgta acctgggcga    7080
aggcgtcgcg caaccttgtg gtgcaaatca aaccgtctgc gagccatgtt tggactctgt    7140
tacgtttagt gacgtagtat ctgcgacaga gccatgcaag ccttgtacgg aatgtgtagg    7200
attgcagagc atgtctgccc cttgtgtaga agccgacgat gcagtttgca ggtgcgcgta    7260
tggctattac caagacgaaa caaccggacg atgtgaagct tgccgagttt gtgaagcggg    7320
ttccgggctt gtattctcct gtcaggataa gcagaacacc gtctgcgaag agtgccccga    7380
tggtacctac agcgatgaag cgaaccatgt agacccatgc ctgccttgca ccgtttgtga    7440
agacacggaa cgacagttgc gggaatgtac ccggtgggca gacgccgagt gcgaagagat    7500
tccaggccgc tggatcacgc gaagtacccc gccagaaggt tccgacagta ctgcaccaag    7560
cacccaagaa ccagaggcgc cccccgagca ggacctgatt gcctccaccg tggcgggtgt    7620
tgttactacg gttatgggct catcccagcc cgttgttacc cgaggaacta cagacaacct    7680
gattccggta tattgttcta tcttggcggc tgtagtagtt ggcttggtcg cgtacatcgc    7740
tttcaaaaga tgaactagtg tcgacaatca acctctggat tacaaaattt gtgaaagatt    7800
gactggtatt cttaactatg ttgctccttt tacgctatgt ggatacgctg ctttaatgcc    7860
tttgtatcat gctattgctt cccgtatggc tttcatttc tcctccttgt ataaatcctg    7920
gttgctgtct ctttatgagg agttgtggcc cgttgtcagg caacgtggcg tggtgtgcac    7980
tgtgtttgct gacgcaaccc ccactggttg gggcattgcc accacctgtc agctcctttc    8040
cgggactttc gctttccccc tccctattgc cacggcggaa ctcatcgccg cctgccttgc    8100
ccgctgctgg acaggggctc ggctgttggg cactgacaat tccgtggtgt tgtcggggaa    8160
gctgacgtcc tttccatggc tgctcgcctg tgttgccacc tggattctgc gcgggacgtc    8220
cttctgctac gtcccttcgg ccctcaatcc agcggacctt ccttcccgcg gcctgctgcc    8280
ggctctgcgg cctcttccgc gtcttcgcct tcgccctcag acgagtcgga tctccctttg    8340
ggccgcctcc ccgcctggaa ttcgagctcg gtacctttaa gaccaatgac ttacaaggca    8400
gctgtagatc ttagccactt tttaaaagaa aagggggac tggaagggct aattcactcc    8460
caacgaagac aagatctgct ttttgcttgt actgggtctc tctggttaga ccagatctga    8520
gcctgggagc tctctggcta actagggaac ccactgctta agcctcaata agcttgcct    8580 tgagtgcttc aagtagtgtg tgcccgtctg ttgtgtgact ctggtaacta gagatccctc    8640 agacccttt agtcagtgtg gaaaatctct agcagtagta gttcatgtca tcttattatt    8700
cagtatttat aacttgcaaa gaaatgaata tcagagagtg agaggaactt gtttattgca    8760
gcttataatg gttacaaata aagcaatagc atcacaaatt tcacaaataa gcatttttt    8820 tcactgcatt ctagttgtgg tttgtccaaa ctcatcaatg tatcttatca tgtctggctc    8880
tagctatccc gcccctaact ccgcccagtt ccgcccattc tccgcccat ggctgactaa    8940 tttttttat ttatgcagag gccgaggccg cctcggcctc tgagctattc cagaagtagt    9000
gaggaggctt ttttggaggc ctaggctttt gcgtcgagac gtacccaatt cgccctatag    9060
```

```
tgagtcgtat tacgcgcgct cactggccgt cgttttacaa cgtcgtgact gggaaaaccc    9120
tggcgttacc caacttaatc gccttgcagc acatccccct ttcgccagct ggcgtaatag    9180
cgaagaggcc cgcaccgatc gcccttccca acagttgcgc agcctgaatg gcgaatggcg    9240
cgacgcgccc tgtagcggcg cattaagcgc ggcgggtgtg gtggttacgc gcagcgtgac    9300
cgctacactt gccagcgccc tagcgcccgc tcctttcgct ttcttccctt cctttctcgc    9360
cacgttcgcc ggctttcccc gtcaagctct aaatcggggg ctcccttag ggttccgatt    9420 tagtgcttta cggcacctcg accccaaaaa acttgattag ggtgatggtt cacgtagtgg    9480
gccatcgccc tgatagacgg ttttcgccc tttgacgttg gagtccacgt tctttaatag    9540
tggactcttg ttccaaactg gaacaacact caaccctatc tcggtctatt cttttgattt    9600
ataagggatt ttgccgattt cggcctattg gttaaaaat gagctgattt aacaaaaatt    9660
taacgcgaat tttaacaaaa tattaacgtt tacaatttcc caggtggcac ttttcgggga    9720
aatgtgcgcg gaaccctat ttgtttattt ttctaaatac attcaaatat gtatccgctc    9780
atgagacaat aaccctgata aatgcttcaa taatattgaa aaaggaagag tatgagtatt    9840
caacatttcc gtgtcgccct tattcccttt tttgcggcat tttgccttcc tgttttgct    9900 cacccagaaa cgctggtgaa agtaaaagat gctgaagatc agttgggtgc acgagtgggt    9960
tacatcgaac tggatctcaa cagcggtaag atccttgaga gttttcgccc cgaagaacgt   10020
tttccaatga tgagcacttt taaagttctg ctatgtggcg cggtattatc ccgtattgac   10080
gccgggcaag agcaactcgg tcgccgcata cactattctc agaatgactt ggttgagtac   10140
tcaccagtca cagaaaagca tcttacggat ggcatgacag taagagaatt atgcagtgct   10200
gccataacca tgagtgataa cactgcggcc aacttacttc tgacaacgat cggaggaccg   10260
aaggagctaa ccgcttttt gcacaacatg ggggatcatg taactcgcct tgatcgttgg   10320
gaaccggagc tgaatgaagc cataccaaac gacgagcgtg acaccacgat gcctgtagca   10380
atggcaacaa cgttgcgcaa actattaact ggcgaactac ttactctagc ttcccggcaa   10440
caattaatag actggatgga ggcggataaa gttgcaggac cacttctgcg ctcggccctt   10500
ccggctggct ggtttattgc tgataaatct ggagccggtg agcgtgggtc tcgcggtatc   10560
attgcagcac tggggccaga tggtaagccc tcccgtatcg tagttatcta cacgacgggg   10620
agtcaggcaa ctatggatga acgaaataga cagatcgctg agataggtgc ctcactgatt   10680
aagcattggt aactgtcaga ccaagtttac tcatatatac tttagattga tttaaaactt   10740
catttttaat ttaaaaggat ctaggtgaag atcctttttg ataatctcat gaccaaaatc   10800
ccttaacgtg agttttcgtt ccactgagcg tcagaccccg tagaaaagat caaaggatct   10860
tcttgagatc cttttttct gcgcgtaatc tgctgcttgc aaacaaaaaa accaccgcta   10920
ccagcggtgg tttgtttgcc ggatcaagag ctaccaactc tttttccgaa ggtaactggc   10980
ttcagcagag cgcagatacc aaatactgtc cttctagtgt agccgtagtt aggccaccac   11040
ttcaagaact ctgtagcacc gcctacatac ctcgctctgc taatcctgtt accagtggct   11100
gctgccagtg gcgataagtc gtgtcttacc gggttggact caagacgata gttaccggat   11160
aaggcgcagc ggtcgggctg aacggggggt tcgtgcacac agcccagctt ggagcgaacg   11220
acctacaccg aactgagata cctacagcgt gagctatgag aaagcgccac gcttcccgaa   11280
gggagaaagg cggacaggta tccggtaagc ggcagggtcg gaacaggaga gcgcacgagg   11340
gagcttccag ggggaaacgc ctggtatctt tatagtcctg tcgggtttcg ccacctctga   11400
```

| | |
|---|---|
| cttgagcgtc gattttttgtg atgctcgtca gggggggcgga gcctatggaa aaacgccagc | 11460 |
| aacgcggcct ttttacggtt cctggccttt tgctggcctt ttgctcacat gttctttcct | 11520 |
| gcgttatccc ctgattctgt ggataaccgt attaccgcct ttgagtgagc tgataccgct | 11580 |
| cgccgcagcc gaacgaccga gcgcagcgag tcagtgagcg aggaagcgga agagcgccca | 11640 |
| atacgcaaac cgcctctccc cgcgcgttgg ccgattcatt aatgcagctg gcacgacagg | 11700 |
| tttcccgact ggaaagcggg cagtgagcgc aacgcaatta atgtgagtta gctcactcat | 11760 |
| taggcacccc aggctttaca ctttatgctt ccggctcgta tgttgtgtgg aattgtgagc | 11820 |
| ggataacaat ttcacacagg aaacagctat gaccatgatt acgccaagcg cgcaattaac | 11880 |
| cctcactaaa gggaacaaaa gctggagctg ca | 11912 |

<210> SEQ ID NO 10
<211> LENGTH: 10320
<212> TYPE: DNA
<213> ORGANISM: Artificial Sequence
<220> FEATURE:
<223> OTHER INFORMATION: lentiviral vector vivo-TIL 108 - TCP4

<400> SEQUENCE: 10

| | |
|---|---|
| agcttaatgt agtcttatgc aatactcttg tagtcttgca acatggtaac gatgagttag | 60 |
| caacatgcct tacaaggaga gaaaaagcac cgtgcatgcc gattggtgga agtaaggtgg | 120 |
| tacgatcgtg ccttattagg aaggcaacag acgggtctga catggattgg acgaaccact | 180 |
| gaattgccgc attgcagaga tattgtattt aagtgcctag ctcgatacaa taaacgggtc | 240 |
| tctctggtta gaccagatct gagcctggga gctctctggc taactaggga acccactgct | 300 |
| taagcctcaa taaagcttgc cttgagtgct tcaagtagtg tgtgcccgtc tgttgtgtga | 360 |
| ctctggtaac tagagatccc tcagaccctt ttagtcagtg tggaaaatct ctagcagtgg | 420 |
| cgcccgaaca gggacttgaa agcgaaaggg aaaccagagg agctctctcg acgcaggact | 480 |
| cggcttgctg aagcgcgcac ggcaagaggc gaggggcggc gactggtgag tacgccaaaa | 540 |
| attttgacta gcggaggcta agaggagaga gatgggtgcg agagcgtcag tattaagcgg | 600 |
| gggagaatta gatcgcgatg ggaaaaaatt cggttaaggc caggggggaa gaaaaaatat | 660 |
| aaattaaaac atatagtatg ggcaagcagg gagctagaac gattcgcagt taatcctggc | 720 |
| ctgttagaaa catcagaagg ctgtagacaa atactgggac agctacaacc atcccttcag | 780 |
| acaggatcag aagaacttag atcattatat aatacagtag caaccctcta ttgtgtgcat | 840 |
| caaaggatag agataaaaga caccaaggaa gctttagaca gatagagga agagcaaaac | 900 |
| aaaagtaaga ccaccgcaca gcaagcggcc gctgatcttc agacctggag gaggagatat | 960 |
| gagggacaat tggagaagtg aattatataa atataaagta gtaaaaattg aaccattagg | 1020 |
| agtagcaccc accaaggcaa agagaagagt ggtgcagaga gaaaaaagag cagtgggaat | 1080 |
| aggagctttg ttccttgggt tcttgggagc agcaggaagc actatgggcg cagcctcaat | 1140 |
| gacgctgacg gtacaggcca gacaattatt gtctggtata gtgcagcagc agaacaattt | 1200 |
| gctgagggct attgaggcgc aacagcatct gttgcaactc acagtctggg gcatcaagca | 1260 |
| gctccaggca agaatcctgg ctgtggaaag atacctaaag gatcaacagc tcctggggat | 1320 |
| ttggggttgc tctggaaaac tcatttgcac cactgctgtg ccttggaatg ctagttggag | 1380 |
| taataaatct ctggaacaga tttggaatca cacgacctgg atggagtggg acagagaaat | 1440 |
| taacaattac acaagcttaa tacactcctt aattgaagaa tcgcaaaacc agcaagaaaa | 1500 |
| gaatgaacaa gaattattgg aattagataa atgggcaagt ttgtggaatt ggtttaacat | 1560 |

```
aacaaattgg ctgtggtata taaaattatt cataatgata gtaggaggct tggtaggttt    1620
aagaatagtt tttgctgtac tttctatagt gaatagagtt aggcagggat attcaccatt    1680
atcgtttcag acccacctcc caaccccgag gggacccgac aggcccgaag aatagaaga     1740 agaaggtgga gagagagaca gagacagatc cattcgatta gtgaacggat ctcgacggta    1800
tcggttaact tttaaaagaa aaggggggat tgggggtac agtgcagggg aaagaatagt     1860
agacataata gcaacagaca tacaaactaa agaattacaa aaacaaatta caaaaattca    1920 aaatttatc gatcacgaga ctagcctcga gaagcttgat atcgaattcc cacggggttg     1980
gacgcgtagt taagtgtctt aaatgactat gattaaaagg tcagacccca tccccagcta    2040
gcagtcatgc agctgtactt tgagggaagt ggggagaaaa aaatagtttt cagttagagt    2100
tctaaaacaa taggtggtga aaggcacct gctttgaaat gctggtgcct tgtctgtggt     2160
cctgtctgcc cgccttctcc ttggcttctt agacttgcta aaccttgtta cactctggca    2220
ggaagctctg agggctaaac cacaaaaact aagtacattc aggacttcct gtgacagctc    2280
actgaggatt gaactacttt ttcctctgaa tctgagagtc tattttttcca gcaaccagag   2340 ttaattacta agggcaatga tgaatgaaac ctcatcgcct cccaaaattc aaacacaaaa    2400
tccagctagg taacaattgc cacaggatct acccagtaga gagatgaggg ctctggccgg    2460
gcatggtggc tcgtgccagt aatcctaaca ctttgggagg ccaaagcagg tagatcacct    2520
tttcttggcc ctacctccaa aatatttcca gatctcccta gcctgcacac ccttgccacc    2580
tgtcattccc acttggacca ggccagcagc ctccctggtc tctctgaccc tcccctgag    2640 ttcgttcacc aaaggcagta acggagacac ccctcaaca cacacaggaa gcagatggcc     2700
ttgacaccag cagggtgaca tccgctattg ctacttctct gctcccccac agttcctctg    2760
gacttctctg gaccacagtc ctctgccaga cccctgccag accccagtcc accgctagca    2820
ccggtgccgc caccatgcct ctgggcctgc tgtggctggg cctggccctg ctgggcgccc    2880
tgcacgccca ggccggcgtg caggtggaga caatctcccc aggcgacgga cgcacattcc    2940
ctaagcgggg ccagacctgc gttgtgcact atacaggcat gctggaggat ggcaagaagt    3000
ttgacagctc ccgggataga aacaagccat tcaagtttat gctgggcaag caggaagtga    3060
tcagaggctg ggaggagggc gtggcccaga tgtctgtggg ccagagggcc aagctgacca    3120
tcagcccaga ctacgcctat ggagcaacag gccacccagg aatcatccca cctcacgcca    3180
ccctggtgtt cgatgtggag ctgctgaagc tgggcgaggg atccaacaca tcaaaagaga    3240
accccttcct gttcgcattg gaggccgtag tcatatctgt tggatccatg ggacttatta    3300
tctccctgtt gtgtgtgtac ttctggctgg aacggactat gcccaggatc cccacgctca    3360
agaatctgga agatctcgtc acagaatacc atggtaattt cagcgcctgg agcggagtct    3420
ctaagggtct ggccgaatcc ctccaacccg attattctga acggttgtgc ctcgtatccg    3480
aaataccacc aaaaggcggg gctctgggtg agggcccagg ggcgagtccg tgcaatcaac    3540
acagcccgta ttgggcccct ccttgttata cgttgaagcc cgaaactgga agcggagcta    3600
ctaacttcag cctgctgaag caggctggag acgtggagga gaaccctgga cctatggcac    3660
tgcccgtgac cgccctgctg ctgcctctgg ccctgctgct gcacgcagcc cggcctatcc    3720
tgtggcacga gatgtggcac gagggcctgg aggaggccag caggctgtat tttggcgagc    3780
gcaacgtgaa gggcatgttc gaggtgctgg agcctctgca cgccatgatg gagagaggcc    3840
cacagaccct gaaggagaca tcctttaacc aggcctatgg acgggacctg atggaggcac    3900
```

```
aggagtggtg cagaaagtac atgaagtctg gcaatgtgaa ggacctgctg caggcctggg    3960
atctgtacta tcacgtgttt cggagaatct ccaagggcaa agacacgatt ccgtggcttg    4020
ggcatctgct cgttgggctg agtggtgcgt ttggtttcat catcttggtc tatctcttga    4080
tcaattgcag aaatacaggc ccttggctga aaaaagtgct caagtgtaat accccccgacc   4140
caagcaagtt cttctcccag cttttcttcag agcatggagg cgatgtgcag aaatggctct   4200
cttcaccttt tccctcctca agcttctccc cgggagggct ggcgcccgag atttcacctc    4260
ttgaggtact tgaacgagac aaggttaccc aacttctcct tcaacaggat aaggtacccg    4320
aacctgcgag ccttagctcc aaccactctc ttacgagctg cttcaccaat cagggatact    4380
tcttttttcca ccttcccgat gcgctggaaa tcgaagcttg tcaagtttac tttacctatg   4440
atccatatag cgaggaagat cccgacgaag gagtcgccgg tgcgcccacg ggttcctcac    4500
cccaacctct ccagcctctc tcaggagaag atgatgctta ttgcactttt cccagtagag    4560
acgatctcct cctcttttct ccatctcttt tggggggacc ttcccccccct tctacggcac   4620
ctggcgggtc tggtgctggc gaggagcgga tgccgccgtc cctccaggag cgagtaccac    4680
gagattggga tccccagcca cttggacccc caccccccgg cgtacctgac cttgtcgatt    4740
ttcaacctcc ccctgaattg gtgctgcgag aggctgggga ggaagttccg gacgctgggc    4800
cgagggaggg cgtgtccttt ccatggagta ggcctccagg tcaaggcgag tttagggctc    4860
tcaacgcgcg gctgccgttg aatacagacg cttatctctc actgcaggaa ctgcaaggtc    4920
aggacccaac acatcttgta ggatctggtg ctactaattt ttctcttttg aagcaagctg    4980
gagatgttga agagaacccc ggtccggaga tgtggcatga gggtctggaa gaagcgtctc    5040
gactgtactt tggtgagcgc aatgtgaagg gcatgtttga agtcctcgaa ccccttcatg    5100
ccatgatgga acgcggaccc cagaccttga aggagacaag ttttaaccaa gcttacggaa    5160
gagacctgat ggaagcccag gaatggtgca ggaaatacat gaaaagcggg aatgtgaagg    5220
acttgctcca agcgtgggac ctgtactatc atgtctttag gcgcattagt aagggcagcg    5280
gcgccaccaa cttcagcctg ctgaagcagg ccggcgacgt ggaggagaac cccggccccg    5340
gtgctggcgc aactgacgc gctatggatg gacctcgctt gctgcttctt ctgcttctcg     5400
gggtctcttt gggtggtgct aaggaagcat gcccaacggg actttatacg catagcggag    5460
agtgttgcaa agcttgtaac ctgggcgaag gcgtcgcgca accttgtggt gcaaatcaaa    5520
ccgtctgcga gccatgtttg gactctgtta cgtttagtga cgtagtatct gcgacagagc    5580
catgcaagcc ttgtacggaa tgtgtaggat tgcagagcat gtctgcccct tgtgtagaag    5640
ccgacgatgc agtttgcagg tgcgcgtatg gctattacca agacgaaaca accggacgat    5700
gtgaagcttg ccgagtttgt gaagcgggtt ccgggcttgt attctcctgt caggataagc    5760
agaacaccgt ctgcgaagag tgccccgatg gtacctacag cgatgaagcg aaccatgtag    5820
acccatgcct gccttgcacc gtttgtgaag acacggaacg acagttgcgg gaatgtaccc    5880
ggtgggcaga cgccgagtgc gaagagattc caggccgctg gatcacgcga gtaccccgc     5940
cagaaggttc cgacagtact gcaccaagca cccaagaacc agaggcgccc ccgagcagg     6000
acctgattgc ctccaccgtg gcgggtgttg ttactacggt tatgggctca tcccagcccg    6060
ttgttacccg aggaactaca gacaacctga ttccggtata ttgttctatc ttggcggctg    6120
tagtagttgg cttggtcgcg tacatcgctt tcaaaagatg aactagtgtc gacaatcaac    6180
ctctggatta caaaatttgt gaaagattga ctggtattct taactatgtt gctccttta    6240
cgctatgtgg atacgctgct ttaatgcctt tgtatcatgc tattgcttcc cgtatggctt    6300
```

```
tcattttctc ctccttgtat aaatcctggt tgctgtctct ttatgaggag ttgtggcccg    6360
ttgtcaggca acgtggcgtg gtgtgcactg tgtttgctga cgcaaccccc actggttggg    6420
gcattgccac cacctgtcag ctcctttccg ggactttcgc tttccccctc cctattgcca    6480
cggcggaact catcgccgcc tgccttgccc gctgctggac aggggctcgg ctgttgggca    6540
ctgacaattc cgtggtgttg tcggggaagc tgacgtcctt tccatggctg ctcgcctgtg    6600
ttgccacctg gattctgcgc gggacgtcct tctgctacgt cccttcggcc ctcaatccag    6660
cggaccttcc ttcccgcggc ctgctgccgg ctctgcggcc tcttccgcgt cttcgccttc    6720
gccctcagac gagtcggatc tccctttggg ccgcctcccc gcctggaatt cgagctcggt    6780
acctttaaga ccaatgactt acaaggcagc tgtagatctt agccactttt taaaagaaaa    6840 gggggggactg gaagggctaa ttcactccca acgaagacaa gatctgcttt ttgcttgtac    6900
tgggtctctc tggttagacc agatctgagc ctgggagctc tctggctaac tagggaaccc    6960
actgcttaag cctcaataaa gcttgccttg agtgcttcaa gtagtgtgtg cccgtctgtt    7020
gtgtgactct ggtaactaga gatccctcag acccttttag tcagtgtgga aaatctctag    7080
cagtagtagt tcatgtcatc ttattattca gtatttataa cttgcaaaga atgaatatc    7140 agagagtgag aggaacttgt ttattgcagc ttataatggt tacaaataaa gcaatagcat    7200
cacaaatttc acaaataaag cattttttc actgcattct agttgtggtt tgtccaaact    7260
catcaatgta tcttatcatg tctggctcta gctatcccgc ccctaactcc gcccagttcc    7320
gcccattctc cgccccatgg ctgactaatt ttttttattt atgcagaggc cgaggccgcc    7380
tcggcctctg agctattcca gaagtagtga ggaggctttt ttggaggcct aggcttttgc    7440
gtcgagacgt acccaattcg ccctatagtg agtcgtatta cgcgcgctca ctggccgtcg    7500
ttttacaacg tcgtgactgg gaaaaccctg gcgttaccca acttaatcgc cttgcagcac    7560 atccccctt cgccagctgg cgtaatagcg aagaggcccg caccgatcgc ccttcccaac    7620
agttgcgcag cctgaatggc gaatggcgcg acgcgccctg tagcggcgca ttaagcgcgg    7680
cgggtgtggt ggttacgcgc agcgtgaccg ctacacttgc cagcgcccta gcgcccgctc    7740
cttttcgctt cttcccttcc tttctcgcca cgttcgccgg cttccccgt caagctctaa    7800 atcgggggct ccctttaggg ttccgattta gtgctttacg gcacctcgac cccaaaaaac    7860
ttgattaggg tgatggttca cgtagtgggc catcgccctg atagacggt tttcgccctt    7920 tgacgttgga gtccacgttc tttaatagtg gactcttgtt ccaaactgga acaacactca    7980
accctatctc ggtctattct tttgatttat aagggatttt gccgatttcg gcctattggt    8040
taaaaaatga gctgatttaa caaaaattta acgcgaattt taacaaaata ttaacgttta    8100
caatttccca ggtggcactt ttcggggaaa tgtgcgcgga acccctattt gtttatttt    8160 ctaaatacat tcaaatatgt atccgctcat gagacaataa ccctgataaa tgcttcaata    8220
atattgaaaa aggaagagta tgagtattca acatttccgt gtcgccctta ttcccttttt    8280
tgcggcattt tgccttcctg tttttgctca cccagaaacg ctggtgaaag taaaagatgc    8340
tgaagatcag ttgggtgcac gagtgggtta catcgaactg gatctcaaca gcggtaagat    8400
ccttgagagt tttcgccccg aagaacgttt tccaatgatg agcactttta aagttctgct    8460
atgtggcgcg gtattatccc gtattgacgc cgggcaagag caactcggtc gccgcataca    8520
ctattctcag aatgacttgg ttgagtactc accagtcaca gaaaagcatc ttacggatgg    8580
catgacagta agagaattat gcagtgctgc cataaccatg agtgataaca ctgcggccaa    8640
```

| | |
|---|---|
| cttacttctg acaacgatcg gaggaccgaa ggagctaacc gctttttgc acaacatggg | 8700 |
| ggatcatgta actcgccttg atcgttggga accggagctg aatgaagcca taccaaacga | 8760 |
| cgagcgtgac accacgatgc ctgtagcaat ggcaacaacg ttgcgcaaac tattaactgg | 8820 |
| cgaactactt actctagctt cccggcaaca attaatagac tggatggagg cggataaagt | 8880 |
| tgcaggacca cttctgcgct cggcccttcc ggctggctgg tttattgctg ataaatctgg | 8940 |
| agccggtgag cgtgggtctc gcggtatcat tgcagcactg gggccagatg gtaagccctc | 9000 |
| ccgtatcgta gttatctaca cgacggggag tcaggcaact atggatgaac gaaatagaca | 9060 |
| gatcgctgag ataggtgcct cactgattaa gcattggtaa ctgtcagacc aagtttactc | 9120 |
| atatatactt tagattgatt taaaacttca ttttttaattt aaaaggatct aggtgaagat | 9180 |
| ccttttttgat aatctcatga ccaaaatccc ttaacgtgag ttttcgttcc actgagcgtc | 9240 |
| agaccccgta gaaaagatca aggatcttc ttgagatcct ttttttctgc gcgtaatctg | 9300 |
| ctgcttgcaa acaaaaaaac caccgctacc agcggtggtt tgtttgccgg atcaagagct | 9360 |
| accaactctt tttccgaagg taactggctt cagcagagcg cagataccaa atactgtcct | 9420 |
| tctagtgtag ccgtagttag gccaccactt caagaactct gtagcaccgc ctacatacct | 9480 |
| cgctctgcta atcctgttac cagtggctgc tgccagtggc gataagtcgt gtcttaccgg | 9540 |
| gttggactca agacgatagt taccggataa ggcgcagcgg tcgggctgaa cggggggttc | 9600 |
| gtgcacacag cccagcttgg agcgaacgac ctacaccgaa ctgagatacc tacagcgtga | 9660 |
| gctatgagaa agcgccacgc ttcccgaagg gagaaaggcg gacaggtatc cggtaagcgg | 9720 |
| cagggtcgga acaggagagc gcacgaggga gcttccaggg ggaaacgcct ggtatcttta | 9780 |
| tagtcctgtc gggtttcgcc acctctgact tgagcgtcga ttttttgtgat gctcgtcagg | 9840 |
| ggggcggagc ctatggaaaa acgccagcaa cgcggccttt ttacggttcc tggccttttg | 9900 |
| ctggcctttt gctcacatgt tctttcctgc gttatcccct gattctgtgg ataaccgtat | 9960 |
| taccgccttt gagtgagctg ataccgctcg ccgcagccga acgaccgagc gcagcgagtc | 10020 |
| agtgagcgag gaagcggaag agcgcccaat acgcaaaccg cctctccccg cgcgttggcc | 10080 |
| gattcattaa tgcagctggc acgacaggtt tcccgactgg aaagcgggca gtgagcgcaa | 10140 |
| cgcaattaat gtgagttagc tcactcatta ggcaccccag gctttacact ttatgcttcc | 10200 |
| ggctcgtatg ttgtgtggaa ttgtgagcgg ataacaattt cacacaggaa acagctatga | 10260 |
| ccatgattac gccaagcgcg caattaaccc tcactaaagg gaacaaaagc tggagctgca | 10320 |

<210> SEQ ID NO 11
<211> LENGTH: 10949
<212> TYPE: DNA
<213> ORGANISM: Artificial Sequence
<220> FEATURE:
<223> OTHER INFORMATION: lentiviral vector vivo-TIL 109 - hPerfP

<400> SEQUENCE: 11

| | |
|---|---|
| agcttaatgt agtcttatgc aatactcttg tagtcttgca acatggtaac gatgagttag | 60 |
| caacatgcct tacaaggaga gaaaaagcac cgtgcatgcc gattggtgga agtaaggtgg | 120 |
| tacgatcgtg ccttattagg aaggcaacag acgggtctga catggattgg acgaaccact | 180 |
| gaattgccgc attgcagaga tattgtattt aagtgcctag ctcgatacaa taaacgggtc | 240 |
| tctctggtta gaccagatct gagcctggga gctctctggc taactaggga acccactgct | 300 |
| taagcctcaa taaagcttgc cttgagtgct tcaagtagtg tgtgcccgtc tgttgtgtga | 360 |
| ctctggtaac tagagatccc tcagaccctt ttagtcagtg tggaaaatct ctagcagtgg | 420 |

```
cgcccgaaca gggacttgaa agcgaaaggg aaaccagagg agctctctcg acgcaggact    480
cggcttgctg aagcgcgcac ggcaagaggc gaggggcggc gactggtgag tacgccaaaa    540
attttgacta gcggaggcta gaaggagaga gatgggtgcg agagcgtcag tattaagcgg    600
gggagaatta gatcgcgatg ggaaaaaatt cggttaaggc cagggggaaa gaaaaaatat    660
aaattaaaac atatagtatg ggcaagcagg gagctagaac gattcgcagt taatcctggc    720
ctgttagaaa catcagaagg ctgtagacaa atactgggac agctacaacc atcccttcag    780
acaggatcag aagaacttag atcattatat aatacagtag caaccctcta ttgtgtgcat    840
caaaggatag agataaaaga caccaaggaa gctttagaca agatagagga agagcaaaac    900
aaaagtaaga ccaccgcaca gcaagcggcc gctgatcttc agacctggag gaggagatat    960
gagggacaat ggagaagtg aattatataa atataaagta gtaaaaattg aaccattagg   1020
agtagcaccc accaaggcaa agagaagagt ggtgcagaga gaaaaaagag cagtgggaat   1080
aggagctttg ttccttgggt tcttgggagc agcaggaagc actatgggcg cagcctcaat   1140
gacgctgacg gtacaggcca gacaattatt gtctggtata gtgcagcagc agaacaattt   1200
gctgagggct attgaggcgc aacagcatct gttgcaactc acagtctggg gcatcaagca   1260
gctccaggca agaatcctgg ctgtggaaag atacctaaag gatcaacagc tcctggggat   1320
ttggggttgc tctggaaaac tcatttgcac cactgctgtg ccttgaatg ctagttggag   1380 taataaatct ctggaacaga tttggaatca cacgacctgg atggagtggg acagagaaat   1440
taacaattac acaagcttaa tacactcctt aattgaagaa tcgcaaaacc agcaagaaaa   1500
gaatgaacaa gaattattgg aattagataa atgggcaagt ttgtggaatt ggtttaacat   1560
aacaaattgg ctgtggtata taaaattatt cataatgata gtaggaggct tggtaggttt   1620
aagaatagtt tttgctgtac tttctatagt gaatagagtt aggcagggat attcaccatt   1680
atcgtttcag acccacctcc caaccccgag gggacccgac aggcccgaag gaatagaaga   1740
agaaggtgga gagagagaca gagacagatc cattcgatta gtgaacggat ctcgacggta   1800
tcggttaact tttaaaagaa aagggggat tggggggtac agtgcagggg aaagaatagt   1860
agacataata gcaacagaca tacaaactaa agaattacaa aaacaaatta caaaaattca   1920
aaattttatc gatcacgaga ctagcctcga gaagcttgat atcgaattcc cacggggttg   1980
gacgcgtagt tccaaagtcc tctctttgat tttataggtg aggaaactaa cgctcagaaa   2040
gggggttgat atctatcgcc gtgaggcata cggtaagttt ctggtgaagc tgggatcaga   2100
acctgtttag acttttgcctc tcttttcccg cagatacttt gcaggacttc tatgtccctc   2160
aaaccggcct tcctgtcatg gtcaggaaag aaactcctca cagcctcagc atccaagtca   2220
ggccatgggt gacagctgga aagtgatcag gaggctgcag tttctagaag agggtgggga   2280
cactgcggag agaagatggg gccagattcc gagaagacag cataagcccc tgttcctgta   2340
agagcaggga cggaagcagg gacataaacg caagggatga gccccaaagt gtgacccatg   2400
agacatgatg tcacatgtgg tctggagcct gcggccactt cttcccatca tatacacagt   2460
tatgagaaca agttgtgaga accacctcct cccttaccca gctgccccca cccagaagc    2520 cgtgtgattt tgcccccag tgccctgtga gtcactccac ccatggaaac ctcacccac    2580 cctgacctca agcaaggcag agtgcagaag acatgtcctc cggtgctacc agaccactct   2640
caccagcacc cacgacctca gcagggctgg agccagcgtg gaggccactg gctgtcctca   2700
caaagcgagg agcaggagcc cctgttcgag gaacatgctt ggagttcgga gcctgggcta   2760
```

```
gggtgggatg taggttgagc aggaagtgga tggcaagatt agagcaacat ctctcttctc    2820
ccactcaggg aggagggaat ggccacaggc tctgacactc aagaagggcc aggcacagtt    2880
ccaagcactt cacaacaacc cctagggtct acatgaccta caatcccaat tgttcagtga    2940
agaaactgag gcacagtgag gctgaagaac cctaccagtc cacactgctg gtgcataacc    3000
gagctgccca agccccggcg gtctggcgtg taggcccatg ctctgagccg ccgcctctgc    3060
ttgcctctta catcccacac atgcgatgct gtgcatcaga agcaaggaga tggccctgct    3120
ggcctgttca tcaacaccag ggccgagtct caaagtcctc agcgccccgc cctcctccgc    3180
ctgtgtgccc tgagtccccg agccccagca gctctactcg gcagatgagc ctctggccct    3240
gctgctcgct tcctgagggc tgtcagtggg gagccggatg agggctgagg acagggtggg    3300
tgcttgtggg aggggagagc acaaaggacc tgtgaccaca gctgggggcg gggcaggaag    3360
tagaagtgat gtgagtggtg gctggtgcaa ggagccacag tgggctgcct gggggggctga   3420
tgccacgcta gcaccggtcc tgcagggccg ccaccatgcc tctgggcctg ctgtggctgg    3480
gcctggccct gctgggcgcc ctgcacgccc aggccggcgt gcaggtggag acaatctccc    3540
caggcgacgg acgcacattc cctaagcggg gccagacctg cgttgtgcac tatacaggca    3600
tgctggagga tggcaagaag tttgacagct cccgggatag aaacaagcca ttcaagttta    3660
tgctgggcaa gcaggaagtg atcagaggct gggaggaggg cgtggcccag atgtctgtgg    3720
gccagagggc caagctgacc atcagcccag actacgccta tggagcaaca ggccacccag    3780
gaatcatccc acctcacgcc accctggtgt cgatgtggga gctgctgaag ctgggcgagg    3840
gatccaacac atcaaaagag aaccccttc tgttcgcatt ggaggccgta gtcatatctg    3900
ttggatccat gggacttatt atctccctgt tgtgtgtgta cttctggctg aacggacta    3960
tgcccaggat ccccacgctc aagaatctgg aagatctcgt cacagaatac catggtaatt    4020
tcagcgcctg gagcggagtc tctaagggtc tggccgaatc cctccaaccc gattattctg    4080
aacggttgtg cctcgtatcc gaaataccac caaaaggcgg ggctctgggt gagggcccag    4140
gggcgagtcc gtgcaatcaa cacagcccgt attgggcccc tccttgttat acgttgaagc    4200
ccgaaactgg aagcggagct actaacttca gcctgctgaa gcaggctgga gacgtggagg    4260
agaaccctgg acctatggca ctgcccgtga ccgccctgct gctgcctctg gccctgctgc    4320
tgcacgcagc ccgcctatc ctgtggcacg agatgtggca cgagggcctg gaggaggcca    4380
gcaggctgta ttttggcgag cgcaacgtga agggcatgtt cgaggtgctg gagcctctgc    4440
acgccatgat ggagagaggc ccacagaccc tgaaggagac atcctttaac caggcctatg    4500
gacgggacct gatggaggca caggagtggt gcagaaagta catgaagtct ggcaatgtga    4560
aggacctgct gcaggcctgg gatctgtact atcacgtgtt tcggagaatc tccaagggca    4620
aagacacgat tccgtggctt gggcatctgc tcgttgggct gagtggtgcg tttggtttca    4680
tcatcttggt ctatctcttg atcaattgca gaaatacagg ccttggctga aaaaagtgc    4740
tcaagtgtaa taccccgac ccaagcaagt tcttctccca gctttcttca gagcatggag    4800
gcgatgtgca gaaatggctc tcttcacctt ttccctcctc aagcttctcc ccgggagggc    4860
tggcgcccga gatttcacct cttgaggtac ttgaacgaga caaggttacc caacttctcc    4920
ttcaacagga taaggtaccc gaacctgcga gccttagctc caaccactct cttacgagct    4980
gcttcaccaa tcaggatac ttcttttcc accttcccga tgcgctggaa atcgaagctt    5040
gtcaagttta ctttacctat gatccatata gcgaggaaga tccgacgaa ggagtcgccg    5100
gtgcgcccac gggttcctca ccccaacctc tccagcctct ctcaggagaa gatgatgctt    5160
```

```
attgcacttt tcccagtaga gacgatctcc tcctcttttc tccatctctt ttgggggac   5220 cttcccccc ttctacggca cctggcgggt ctggtgctgg cgaggagcgg atgccgccgt    5280
ccctccagga gcgagtacca cgagattggg atccccagcc acttggaccc cccaccccg    5340 gcgtacctga ccttgtcgat tttcaacctc ccctgaatt ggtgctgcga gaggctgggg    5400
aggaagttcc ggacgctggg ccgagggagg gcgtgtcctt tccatggagt aggcctccag   5460
gtcaaggcga gtttagggct ctcaacgcgc ggctgccgtt gaatacagac gcttatctct   5520
cactgcagga actgcaaggt caggacccaa cacatcttgt aggatctggt gctactaatt   5580
tttctctttt gaagcaagct ggagatgttg aagagaaccc cggtccggag atgtggcatg   5640
agggtctgga agaagcgtct cgactgtact ttggtgagcg caatgtgaag ggcatgtttg   5700
aagtcctcga accccttcat gccatgatgg aacgcggacc ccagaccttg aaggagacaa   5760
gttttaacca agcttacgga agagacctga tggaagccca ggaatggtgc aggaaataca   5820
tgaaaagcgg gaatgtgaag gacttgctcc aagcgtggga cctgtactat catgtcttta   5880
ggcgcattag taagggcagc ggcgccacca acttcagcct gctgaagcag gccggcgacg   5940
tggaggagaa ccccggcccc ggtgctggcg caactgacg cgctatggat ggacctcgct   6000
tgctgcttct tctgcttctc ggggtctctt tgggtggtgc taaggaagca tgcccaacgg   6060
gactttatac gcatagcgga gagtgttgca aagcttgtaa cctgggcgaa ggcgtcgcgc   6120
aaccttgtgg tgcaaatcaa accgtctgcg agccatgttt ggactctgtt acgtttagtg   6180
acgtagtatc tgcgacagag ccatgcaagc cttgtacgga atgtgtagga ttgcagagca   6240
tgtctgcccc ttgtgtagaa gccgacgatg cagtttgcag gtgcgcgtat ggctattacc   6300
aagacgaaac aaccggacga tgtgaagctt gccgagtttg tgaagcgggt tccgggcttg   6360
tattctcctg tcaggataag cagaacaccg tctgcgaaga gtgccccgat ggtacctaca   6420
gcgatgaagc gaaccatgta gacccatgcc tgccttgcac cgtttgtgaa gacacggaac   6480
gacagttgcg ggaatgtacc cggtgggcag acgccgagtg cgaagagatt ccaggccgct   6540
ggatcacgcg aagtacccg ccagaaggtt ccgacagtac tgcaccaagc acccaagaac   6600
cagaggcgcc ccccgagcag gacctgattg cctccaccgt ggcgggtgtt gttactacgg   6660
ttatgggctc atcccagccc gttgttaccc gaggaactac agacaacctg attccggtat   6720
attgttctat cttggcggct gtagtagttg gcttggtcgc gtacatcgct ttcaaaagat   6780
gaacgccggc gctagtgtcg acaatcaacc tctggattac aaaatttgtg aaagattgac   6840
tggtattctt aactatgttg ctccttttac gctatgtgga tacgctgctt taatgccttt   6900
gtatcatgct attgcttccc gtatggcttt cattttctcc tccttgtata aatcctggtt   6960
gctgtctctt tatgaggagt tgtggcccgt tgtcaggcaa cgtggcgtgg tgtgcactgt   7020
gtttgctgac gcaacccca ctggttgggg cattgccacc acctgtcagc tcctttccgg   7080
gactttcgct ttccccctcc ctattgccac ggcggaactc atcgccgcct gccttgcccg   7140
ctgctggaca ggggctcggc tgttgggcac tgacaattcc gtggtgttgt cggggaagct   7200
gacgtccttt ccatggctgc tcgcctgtgt tgccacctgg attctgcgcg gacgtccttt   7260
ctgctacgtc ccttcggccc tcaatccagc ggaccttcct tcccgcggcc tgctgccggc   7320
tctgcggcct cttccgcgtc ttcgccttcg ccctcagacg agtcggatct ccctttgggc   7380
cgcctccccg cctggaattc gagctcggta ccttttaagac caatgactta caaggcagct   7440
gtagatctta gccacttttt aaaagaaaag gggggactgg aagggctaat tcactcccaa   7500
```

```
cgaagacaag atctgctttt tgcttgtact gggtctctct ggttagacca gatctgagcc    7560
tgggagctct ctggctaact agggaaccca ctgcttaagc ctcaataaag cttgccttga    7620
gtgcttcaag tagtgtgtgc ccgtctgttg tgtgactctg gtaactagag atccctcaga    7680
ccctttagt cagtgtggaa aatctctagc agtagtagtt catgtcatct tattattcag     7740
tatttataac ttgcaaagaa atgaatatca gagagtgaga ggaacttgtt tattgcagct    7800
tataatggtt acaaataaag caatagcatc acaaatttca caaataaagc attttttca    7860
ctgcattcta gttgtggttt gtccaaactc atcaatgtat cttatcatgt ctggctctag    7920
ctatcccgcc cctaactccg cccagttccg cccattctcc gccccatggc tgactaattt    7980
tttttattta tgcagaggcc gaggccgcct cggcctctga gctattccag aagtagtgag    8040
gaggcttttt tggaggccta ggcttttgcg tcgagacgta cccaattcgc cctatagtga    8100
gtcgtattac gcgcgctcac tggccgtcgt tttacaacgt cgtgactggg aaaaccctgg    8160
cgttacccaa cttaatcgcc ttgcagcaca tccccctttc gccagctggc gtaatagcga    8220
agaggcccgc accgatcgcc cttcccaaca gttgcgcagc ctgaatggcg aatggcgcga    8280
cgcgccctgt agcggcgcat taagcgcggc gggtgtggtg gttacgcgca gcgtgaccgc    8340
tacacttgcc agcgccctag cgcccgctcc tttcgctttc ttcccttcct ttctcgccac    8400
gttcgccggc tttccccgtc aagctctaaa tcggggctc cctttagggt tccgatttag     8460
tgctttacgg cacctcgacc ccaaaaaact tgattaggt gatggttcac gtagtgggcc     8520
atcgccctga tagacggttt ttcgcccttt gacgttggag tccacgttct ttaatagtgg    8580
actcttgttc caaactggaa caacactcaa ccctatctcg gtctattctt ttgatttata    8640
agggattttg ccgatttcgg cctattggtt aaaaaatgag ctgatttaac aaaaatttaa    8700
cgcgaatttt aacaaaatat taacgtttac aatttcccag gtggcacttt tcggggaaat    8760
gtgcgcggaa cccctatttg tttatttttc taaatacatt caaatatgta tccgctcatg    8820
agacaataac cctgataaat gcttcaataa tattgaaaaa ggaagagtat gagtattcaa    8880
catttccgtg tcgcccttat tccctttttt gcggcatttt gccttcctgt ttttgctcac    8940
ccagaaacgc tggtgaaagt aaaagatgct gaagatcagt tgggtgcacg agtgggttac    9000
atcgaactgg atctcaacag cggtaagatc cttgagagtt ttcgccccga agaacgtttt    9060
ccaatgatga gcacttttaa agttctgcta tgtggcgcgg tattatcccg tattgacgcc    9120
gggcaagagc aactcggtcg ccgcatacac tattctcaga atgacttggt tgagtactca    9180
ccagtcacag aaaagcatct tacggatggc atgacagtaa gagaattatg cagtgctgcc    9240
ataaccatga gtgataacac tgcggccaac ttacttctga caacgatcgg aggaccgaag    9300
gagctaaccg cttttttgca caacatgggg gatcatgtaa ctcgccttga tcgttgggaa    9360
ccggagctga atgaagccat accaaacgac gagcgtgaca ccacgatgcc tgtagcaatg    9420
gcaacaacgt tgcgcaaact attaactggc gaactactta ctctagcttc ccggcaacaa    9480
ttaatagact ggatggaggc ggataaagtt gcaggaccac ttctgcgctc ggcccttccg    9540
gctggctggt ttattgctga taaatctgga gccggtgagc gtgggtctcg cggtatcatt    9600
gcagcactgg ggccagatgg taagccctcc cgtatcgtag ttatctacac gacggggagt    9660
caggcaacta tggatgaacg aaatagacag atcgctgaga taggtgcctc actgattaag    9720
cattggtaac tgtcagacca agtttactca tatatacttt agattgattt aaaacttcat    9780
ttttaattta aaaggatcta ggtgaagatc ctttttgata atctcatgac caaaatccct    9840
taacgtgagt tttcgttcca ctgagcgtca gaccccgtag aaaagatcaa aggatcttct    9900
```

```
tgagatcctt tttttctgcg cgtaatctgc tgcttgcaaa caaaaaaacc accgctacca   9960
gcggtggttt gtttgccgga tcaagagcta ccaactcttt ttccgaaggt aactggcttc  10020
agcagagcgc agataccaaa tactgtcctt ctagtgtagc cgtagttagg ccaccacttc  10080
aagaactctg tagcaccgcc tacatacctc gctctgctaa tcctgttacc agtggctgct  10140
gccagtggcg ataagtcgtg tcttaccggg ttggactcaa gacgatagtt accggataag  10200
gcgcagcggt cgggctgaac ggggggttcg tgcacacagc ccagcttgga gcgaacgacc  10260
tacaccgaac tgagatacct acagcgtgag ctatgagaaa gcgccacgct tcccgaaggg  10320
agaaaggcgg acaggtatcc ggtaagcggc agggtcggaa caggagagcg cacgagggag  10380
cttccagggg gaaacgcctg gtatctttat agtcctgtcg ggtttcgcca cctctgactt  10440
gagcgtcgat ttttgtgatg ctcgtcaggg gggcggagcc tatggaaaaa cgccagcaac  10500
gcggcctttt tacggttcct ggccttttgc tggccttttg ctcacatgtt ctttcctgcg  10560
ttatcccctg attctgtgga taaccgtatt accgcctttg agtgagctga taccgctcgc  10620
cgcagccgaa cgaccgagcg cagcgagtca gtgagcgagg aagcggaaga gcgcccaata  10680
cgcaaaccgc ctctccccgc gcgttggccg attcattaat gcagctggca cgacaggttt  10740
cccgactgga aagcgggcag tgagcgcaac gcaattaatg tgagttagct cactcattag  10800
gcacccagg  cttt acactt  tatgcttccg gctcgtatgt tgtgtggaat tgtgagcgga  10860
taacaatttc acacaggaaa cagctatgac catgattacg ccaagcgcgc aattaaccct  10920
cactaaaggg aacaaaagct ggagctgca                                    10949
```

<210> SEQ ID NO 12
<211> LENGTH: 450
<212> TYPE: PRT
<213> ORGANISM: Artificial Sequence
<220> FEATURE:
<223> OTHER INFORMATION: RACCR-beta - FKBP-IL2Rb fusion protein with
      signal peptide with 2A peptide

<400> SEQUENCE: 12

```
Met Ala Leu Pro Val Thr Ala Leu Leu Pro Leu Ala Leu Leu Leu
1               5                   10                  15

His Ala Ala Arg Pro Ile Leu Trp His Glu Met Trp His Glu Gly Leu
            20                  25                  30

Glu Glu Ala Ser Arg Leu Tyr Phe Gly Glu Arg Asn Val Lys Gly Met
        35                  40                  45

Phe Glu Val Leu Glu Pro Leu His Ala Met Met Glu Arg Gly Pro Gln
    50                  55                  60

Thr Leu Lys Glu Thr Ser Phe Asn Gln Ala Tyr Gly Arg Asp Leu Met
65                  70                  75                  80

Glu Ala Gln Glu Trp Cys Arg Lys Tyr Met Lys Ser Gly Asn Val Lys
                85                  90                  95

Asp Leu Leu Gln Ala Trp Asp Leu Tyr Tyr His Val Phe Arg Arg Ile
            100                 105                 110

Ser Lys Gly Lys Asp Thr Ile Pro Trp Leu Gly His Leu Leu Val Gly
        115                 120                 125

Leu Ser Gly Ala Phe Gly Phe Ile Ile Leu Val Tyr Leu Leu Ile Asn
    130                 135                 140

Cys Arg Asn Thr Gly Pro Trp Leu Lys Lys Val Leu Lys Cys Asn Thr
145                 150                 155                 160
```

```
Pro Asp Pro Ser Lys Phe Phe Ser Gln Leu Ser Ser Glu His Gly Gly
            165                 170                 175

Asp Val Gln Lys Trp Leu Ser Ser Pro Phe Pro Ser Ser Ser Phe Ser
            180                 185                 190

Pro Gly Gly Leu Ala Pro Glu Ile Ser Pro Leu Glu Val Leu Glu Arg
            195                 200                 205

Asp Lys Val Thr Gln Leu Leu Leu Gln Asp Lys Val Pro Glu Pro
            210                 215                 220

Ala Ser Leu Ser Ser Asn His Ser Leu Thr Ser Cys Phe Thr Asn Gln
225                 230                 235                 240

Gly Tyr Phe Phe Phe His Leu Pro Asp Ala Leu Glu Ile Glu Ala Cys
                245                 250                 255

Gln Val Tyr Phe Thr Tyr Asp Pro Tyr Ser Glu Glu Asp Pro Asp Glu
            260                 265                 270

Gly Val Ala Gly Ala Pro Thr Gly Ser Ser Pro Gln Pro Leu Gln Pro
            275                 280                 285

Leu Ser Gly Glu Asp Asp Ala Tyr Cys Thr Phe Pro Ser Arg Asp Asp
    290                 295                 300

Leu Leu Leu Phe Ser Pro Ser Leu Leu Gly Gly Pro Ser Pro Pro Ser
305                 310                 315                 320

Thr Ala Pro Gly Gly Ser Gly Ala Gly Glu Glu Arg Met Pro Pro Ser
                325                 330                 335

Leu Gln Glu Arg Val Pro Arg Asp Trp Asp Pro Gln Pro Leu Gly Pro
            340                 345                 350

Pro Thr Pro Gly Val Pro Asp Leu Val Asp Phe Gln Pro Pro Pro Glu
            355                 360                 365

Leu Val Leu Arg Glu Ala Gly Glu Val Pro Asp Ala Gly Pro Arg
370                 375                 380

Glu Gly Val Ser Phe Pro Trp Ser Arg Pro Pro Gly Gln Gly Glu Phe
385                 390                 395                 400

Arg Ala Leu Asn Ala Arg Leu Pro Leu Asn Thr Asp Ala Tyr Leu Ser
                405                 410                 415

Leu Gln Glu Leu Gln Gly Gln Asp Pro Thr His Leu Val Gly Ser Gly
            420                 425                 430

Ala Thr Asn Phe Ser Leu Leu Lys Gln Ala Gly Asp Val Glu Glu Asn
            435                 440                 445

Pro Gly
450

<210> SEQ ID NO 13
<211> LENGTH: 89
<212> TYPE: PRT
<213> ORGANISM: Artificial Sequence
<220> FEATURE:
<223> OTHER INFORMATION: FKBP domain

<400> SEQUENCE: 13

Glu Met Trp His Glu Gly Leu Glu Glu Ala Ser Arg Leu Tyr Phe Gly
1               5                   10                  15

Glu Arg Asn Val Lys Gly Met Phe Glu Val Leu Glu Pro Leu His Ala
            20                  25                  30

Met Met Glu Arg Gly Pro Gln Thr Leu Lys Glu Thr Ser Phe Asn Gln
        35                  40                  45

Ala Tyr Gly Arg Asp Leu Met Glu Ala Gln Glu Trp Cys Arg Lys Tyr
    50                  55                  60
```

```
Met Lys Ser Gly Asn Val Lys Asp Leu Leu Gln Ala Trp Asp Leu Tyr
 65                  70                  75                  80

Tyr His Val Phe Arg Arg Ile Ser Lys
                 85
```

<210> SEQ ID NO 14
<211> LENGTH: 315
<212> TYPE: PRT
<213> ORGANISM: Artificial Sequence
<220> FEATURE:
<223> OTHER INFORMATION: IL2Rb domain

<400> SEQUENCE: 14

```
Gly Lys Asp Thr Ile Pro Trp Leu Gly His Leu Leu Val Gly Leu Ser
  1               5                  10                  15

Gly Ala Phe Gly Phe Ile Ile Leu Val Tyr Leu Leu Ile Asn Cys Arg
             20                  25                  30

Asn Thr Gly Pro Trp Leu Lys Lys Val Leu Lys Cys Asn Thr Pro Asp
         35                  40                  45

Pro Ser Lys Phe Phe Ser Gln Leu Ser Ser Glu His Gly Gly Asp Val
     50                  55                  60

Gln Lys Trp Leu Ser Ser Pro Phe Pro Ser Ser Ser Phe Ser Pro Gly
 65                  70                  75                  80

Gly Leu Ala Pro Glu Ile Ser Pro Leu Glu Val Leu Glu Arg Asp Lys
                 85                  90                  95

Val Thr Gln Leu Leu Leu Gln Gln Asp Lys Val Pro Glu Pro Ala Ser
            100                 105                 110

Leu Ser Ser Asn His Ser Leu Thr Ser Cys Phe Thr Asn Gln Gly Tyr
        115                 120                 125

Phe Phe Phe His Leu Pro Asp Ala Leu Glu Ile Glu Ala Cys Gln Val
    130                 135                 140

Tyr Phe Thr Tyr Asp Pro Tyr Ser Glu Glu Asp Pro Asp Glu Gly Val
145                 150                 155                 160

Ala Gly Ala Pro Thr Gly Ser Ser Pro Gln Pro Leu Gln Pro Leu Ser
                165                 170                 175

Gly Glu Asp Asp Ala Tyr Cys Thr Phe Pro Ser Arg Asp Asp Leu Leu
            180                 185                 190

Leu Phe Ser Pro Ser Leu Leu Gly Gly Pro Ser Pro Ser Thr Ala
        195                 200                 205

Pro Gly Gly Ser Gly Ala Gly Glu Glu Arg Met Pro Pro Ser Leu Gln
    210                 215                 220

Glu Arg Val Pro Arg Asp Trp Asp Pro Gln Pro Leu Gly Pro Pro Thr
225                 230                 235                 240

Pro Gly Val Pro Asp Leu Val Asp Phe Gln Pro Pro Pro Glu Leu Val
                245                 250                 255

Leu Arg Glu Ala Gly Glu Glu Val Pro Asp Ala Gly Pro Arg Glu Gly
            260                 265                 270

Val Ser Phe Pro Trp Ser Arg Pro Pro Gly Gln Gly Glu Phe Arg Ala
        275                 280                 285

Leu Asn Ala Arg Leu Pro Leu Asn Thr Asp Ala Tyr Leu Ser Leu Gln
    290                 295                 300

Glu Leu Gln Gly Gln Asp Pro Thr His Leu Val
305                 310                 315
```

<210> SEQ ID NO 15

<211> LENGTH: 272
<212> TYPE: PRT
<213> ORGANISM: Artificial Sequence
<220> FEATURE:
<223> OTHER INFORMATION: RACCR-gamma - FRB-IL2Rg fusion protein with
      signal peptide with 2A peptide

<400> SEQUENCE: 15

Met Pro Leu Gly Leu Leu Trp Leu Gly Leu Ala Leu Leu Gly Ala Leu
1               5                   10                  15

His Ala Gln Ala Gly Val Gln Val Glu Thr Ile Ser Pro Gly Asp Gly
            20                  25                  30

Arg Thr Phe Pro Lys Arg Gly Gln Thr Cys Val Val His Tyr Thr Gly
        35                  40                  45

Met Leu Glu Asp Gly Lys Lys Phe Asp Ser Ser Arg Asp Arg Asn Lys
50                  55                  60

Pro Phe Lys Phe Met Leu Gly Lys Gln Glu Val Ile Arg Gly Trp Glu
65                  70                  75                  80

Glu Gly Val Ala Gln Met Ser Val Gly Gln Arg Ala Lys Leu Thr Ile
                85                  90                  95

Ser Pro Asp Tyr Ala Tyr Gly Ala Thr Gly His Pro Gly Ile Ile Pro
            100                 105                 110

Pro His Ala Thr Leu Val Phe Asp Val Glu Leu Leu Lys Leu Gly Glu
        115                 120                 125

Gly Ser Asn Thr Ser Lys Glu Asn Pro Phe Leu Phe Ala Leu Glu Ala
130                 135                 140

Val Val Ile Ser Val Gly Ser Met Gly Leu Ile Ile Ser Leu Leu Cys
145                 150                 155                 160

Val Tyr Phe Trp Leu Glu Arg Thr Met Pro Arg Ile Pro Thr Leu Lys
                165                 170                 175

Asn Leu Glu Asp Leu Val Thr Glu Tyr His Gly Asn Phe Ser Ala Trp
            180                 185                 190

Ser Gly Val Ser Lys Gly Leu Ala Glu Ser Leu Gln Pro Asp Tyr Ser
        195                 200                 205

Glu Arg Leu Cys Leu Val Ser Glu Ile Pro Pro Lys Gly Gly Ala Leu
210                 215                 220

Gly Glu Gly Pro Gly Ala Ser Pro Cys Asn Gln His Ser Pro Tyr Trp
225                 230                 235                 240

Ala Pro Pro Cys Tyr Thr Leu Lys Pro Glu Thr Gly Ser Gly Ala Thr
                245                 250                 255

Asn Phe Ser Leu Leu Lys Gln Ala Gly Asp Val Glu Glu Asn Pro Gly
            260                 265                 270

<210> SEQ ID NO 16
<211> LENGTH: 108
<212> TYPE: PRT
<213> ORGANISM: Artificial Sequence
<220> FEATURE:
<223> OTHER INFORMATION: FRB domain

<400> SEQUENCE: 16

Gly Val Gln Val Glu Thr Ile Ser Pro Gly Asp Gly Arg Thr Phe Pro
1               5                   10                  15

Lys Arg Gly Gln Thr Cys Val Val His Tyr Thr Gly Met Leu Glu Asp
            20                  25                  30

Gly Lys Lys Phe Asp Ser Ser Arg Asp Arg Asn Lys Pro Phe Lys Phe
        35                  40                  45

-continued

```
Met Leu Gly Lys Gln Glu Val Ile Arg Gly Trp Glu Glu Gly Val Ala
    50                  55                  60

Gln Met Ser Val Gly Gln Arg Ala Lys Leu Thr Ile Ser Pro Asp Tyr
65                  70                  75                  80

Ala Tyr Gly Ala Thr Gly His Pro Gly Ile Ile Pro Pro His Ala Thr
                85                  90                  95

Leu Val Phe Asp Val Glu Leu Leu Lys Leu Gly Glu
                100                 105

<210> SEQ ID NO 17
<211> LENGTH: 123
<212> TYPE: PRT
<213> ORGANISM: Artificial Sequence
<220> FEATURE:
<223> OTHER INFORMATION: IL2Rg domain

<400> SEQUENCE: 17

Gly Ser Asn Thr Ser Lys Glu Asn Pro Phe Leu Phe Ala Leu Glu Ala
1               5                   10                  15

Val Val Ile Ser Val Gly Ser Met Gly Leu Ile Ile Ser Leu Leu Cys
                20                  25                  30

Val Tyr Phe Trp Leu Glu Arg Thr Met Pro Arg Ile Pro Thr Leu Lys
            35                  40                  45

Asn Leu Glu Asp Leu Val Thr Glu Tyr His Gly Asn Phe Ser Ala Trp
        50                  55                  60

Ser Gly Val Ser Lys Gly Leu Ala Glu Ser Leu Gln Pro Asp Tyr Ser
65                  70                  75                  80

Glu Arg Leu Cys Leu Val Ser Glu Ile Pro Pro Lys Gly Gly Ala Leu
                85                  90                  95

Gly Glu Gly Pro Gly Ala Ser Pro Cys Asn Gln His Ser Pro Tyr Trp
                100                 105                 110

Ala Pro Pro Cys Tyr Thr Leu Lys Pro Glu Thr
                115                 120
```

VIRAL VECTORS AND PACKAGING CELL LINES

CROSS-REFERENCE TO RELATED APPLICATIONS

This application claims priority to U.S. Provisional Patent Application No. 62/656,823, filed Apr. 12, 2018, the disclosure of which is incorporated by reference herein in its entirety for all purposes.

DESCRIPTION OF THE TEXT FILE SUBMITTED ELECTRONICALLY

The Sequence Listing associated with this application is provided in text format in lieu of a paper copy, and is hereby incorporated by reference into the specification. The name of the text file containing the Sequence Listing is VITI_001_01WO_SeqList_ST25.txt. The text file is 94 KB, was created on Apr. 11, 2019, and is being submitted electronically via EFS-Web.

FIELD OF THE INVENTION

The disclosure relates generally to viral vectors, packaging cell lines, and related methods of use and in particular for expansion of immune cell populations in vivo for treatment of a disease condition.

BACKGROUND OF THE INVENTION

Cancer immunotherapy is a treatment modality based on therapeutic induction of immune responses to tumors. Adoptive T cell therapy (ACT) is one form of cancer immunotherapy. Lymphocytes, particularly tumor-infiltrating lymphocytes (TILs), are isolated from the body, cultured ex vivo, expanded, and then re-infused. The expansion step may include antigen-specific expansion or genetic engineering of the TILs. ACT is reviewed in Rosenberg et al. Adoptive cell transfer as personalized immunotherapy for human cancer. *Science*. 348:62-8 (2015).

The present inventors have realized that, as an alternative to ACT, in vivo transduction of TILs, or other immune cells, could potentiate expansion of cells in vivo rather than ex vivo. Furthermore, the present inventors have realized in vivo transduction of TILs, or other immune cells, would allow for treatment of cancer or other disease conditions without the costly, time-consuming, and risky procedures required by ACT.

Accordingly, there is a need for means of expanding populations of TILs or other immune cells in vivo. In particular, there is a need for therapeutic agents capable of selectively expanding desirable populations of TILs or other immune cells in vivo. The present disclosure provides viral vectors, packaging cell lines, and related methods of use for expansion of TILs or other immune cells in vivo for treatment of a disease condition.

SUMMARY OF THE INVENTION

The present disclosure is based, in part, on the discovery that lentiviral vectors and packaging cell lines designed to express T-cell/NK-cell activation receptors (as well as optionally other effector proteins) are useful for in vivo expansion of T-cells. Lentiviral vectors and packaging cell lines of the present disclosure may be adapted for transduction and drug-mediated expansion of tumor-infiltrating lymphocytes in vivo, such as when the lentiviral vector is packaged into a lentiviral particle using a packaging cell line and the resulting lentiviral particles are delivered into the body of a subject. Intratumoral injection of lentiviral particles according to the present disclosure results in in vivo expansion of tumor-infiltrating lymphocytes. Expansion of tumor-infiltrating lymphocytes is controllable by use of a small molecule, when the T-cell/NK-cell activation receptor is capable of being activated (or inactivated) by such a small molecule. Optionally, the packaging cell line expresses a T-cell activation or co-stimulation molecule, facilitating T-cell transduction by lentiviral particles derived from the packaging cell line in the absence of exogenous activating agents. Optionally, the lentiviral vector confers resistance to immunosuppressive drug(s), facilitating selective expansion of target cells.

In one aspect, the disclosure provides a nucleic acid vector comprising a T-cell and/or NK-cell specific promoter operatively linked to a nucleic acid sequence encoding T-cell/NK-cell activation receptor, wherein the T-cell/NK-cell activation receptor is capable of being activated by a small molecule. In an embodiment, the nucleic acid vector is a lentiviral vector. In an embodiment, the nucleic acid vector comprises a sequence at least partially identical to SEQ ID NOs: 6-11 or fragments thereof.

In another aspect, the disclosure provides a nucleic acid vector comprising a strong promoter operatively linked to a nucleic acid sequence encoding a T-cell/NK-cell activation receptor, wherein the T-cell/NK-cell activation receptor is capable of being activated by a small molecule. In an embodiment, the strong promoter is selected from SEQ ID NOs: 1-5.

In another aspect, the disclosure provides a packaging cell line for generating lentiviral particles capable of activating and efficiently transducing T cells, comprising cultured cells capable of packaging a lentivirus vector, wherein the cultured cells are genetically engineered to express a T-cell activation or co-stimulation molecule.

In another aspect, the disclosure provides a lentiviral particle comprising a nucleic acid vector, such as any of the nucleic acid vectors of the present disclosure. In an embodiment, the lentiviral particle comprises a T-cell activation or co-stimulation molecule, e.g., an anti-CD3 antibody, CD28 ligand, or 41bb ligand.

In another aspect, the disclosure provides a lentiviral particle for activating and efficiently transducing T cells, prepared by transducing the nucleic acid vector of claim 19 into cultured cells genetically engineered to express a T-cell activation or co-stimulation molecule.

In another aspect, the disclosure provides a method for treating a subject suffering from cancer, comprising administering any of the lentiviral particles of the present disclosure to the subject, and administering a small molecule (the T-cell/NK-cell activation receptor of the lentiviral particle being capable of being activated by the small molecule) to the subject, wherein the cancer is treated in the subject. In In another aspect, the disclosure provides a method for expanding T-cells capable of recognizing and killing tumor cells in a subject in need thereof, comprising administering any of the lentiviral particles of the present disclosure to the subject, and administering a small molecule (the T-cell/NK-cell activation receptor of the lentiviral particle being capable of being activated by a small molecule) to the subject, wherein T-cells capable of recognizing and killing tumor cells in the subject are expanded.

In another aspect, the disclosure provides a nucleic acid comprising a promoter specific to T-cells, NK cells, or T-cells and NK cells, wherein the sequence of the nucleic acid is at least 90% identical to a sequence selected from the group consisting of SEQ ID NOs: 1-4.

Additional aspects and embodiments of the disclosure will be apparent from the detailed description that follows.

BRIEF DESCRIPTION OF THE DRAWINGS

FIG. 1A is a diagram of an embodiment of the surface-engineered lentiviral particle, which comprises surface-expressed anti-CD3 and T-cell co-stimulatory molecules not present in the lentiviral particle depicted in FIG. 1B.

FIGS. 3A-3E depict analysis of the parental HEK-293 cell line for CD46 (expected constitutive expression), and CD86/CD137L expression (no expression expected). No detectable fluorescence labeling was observed in the unstained (mock) samples (FIG. 3A). High expression of CD46 was detected by anti-CD46 antibody staining (FIG. 3A-B; PE anti-human CD46), and no expression of either CD86 (FIG. 3E; pacific blue anti-human CD86) or CD137L (FIG. 3D; PE anti-human 4-1BB ligand (CD137L)) detected by specific staining for CD86 and CD137L, respectively.

FIGS. 3F-3K depict analysis of the HATSE-293 cell line for for CD46 (expected constitutive expression on both cell lines), and CD86/CD137L expression ($CD86^{\pm}/CD137L^+$ expression expected). FIG. 3F and FIG. 3G demonstrate no detectable fluorescence labeling in the unstained (mock) samples. FIG. 3H and FIG. 3I demonstrate uniform high expression of CD46 detected by anti-CD46 antibody staining (PE anti-human CD46). FIG. 3J and FIG. 3K demonstrate two populations that express low and high amounts of either CD86 or CD137L are detected using anti-CD86 (FIG. 3J) and anti-CD137L (FIG. 3K) antibodies, respectively.

FIG. 12A illustrates the design the exemplified RACCR molecule. FIG. 12A shows cells transduced with a control lentiviral particle expressing GFP. FIG. 12B shows cells transduced with a surface-engineered particle expressing mCherry. FIG. 12C shows cells transduced with a surface-engineered particle expressing RACCR.

FIG. 12E shows a graph of T-cell expansion of T cells transduced with various surface engineered lentiviral particles (SE-LVP), including SE-LVPs expressing RACCR, in the presence of IL-2 or rapamycin. FIG. 12F shows data confirming T cell expansion driven by RACCR is controllable with rapamycin.

DETAILED DESCRIPTION

Figure 1A:
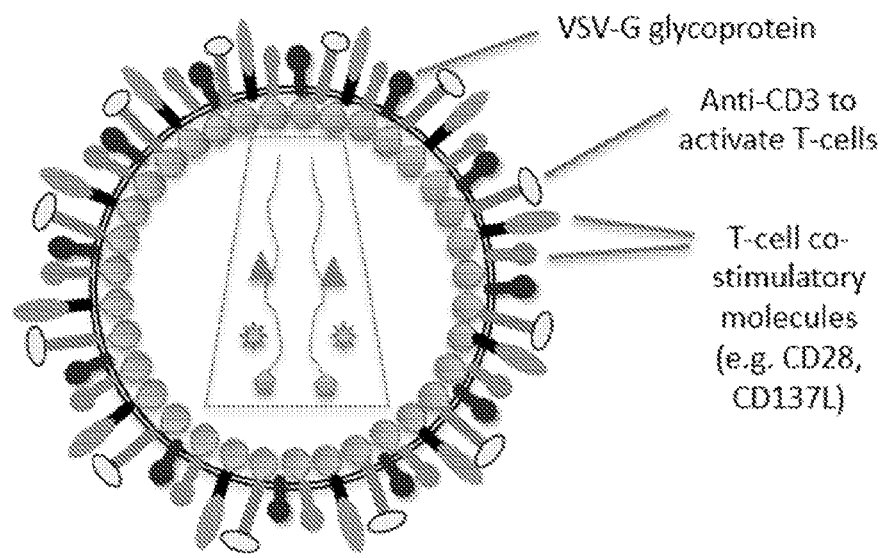
FIGS. 1A-1B depict lentiviral particles.

The present inventors have realized that, as an alternative to ACT, in vivo transduction of TILs, or other immune cells, could potentiate expansion of cells in vivo rather than ex vivo. Furthermore, the present inventors have realized in vivo transduction of TILs, or other immune cells, allows for treatment of cancer or other disease conditions without the drawbacks of ex vivo expansion of immune cells.

Thus, the present disclosure provides means of expanding populations of TILs or other immune cells in vivo. In particular, the present disclosure provides therapeutic agents capable of selectively expanding desirable populations of TILs or other immune cells in vivo. The present disclosure provides viral vectors and related methods of use for expansion of TILs or other immune cells in vivo for treatment of a disease condition.

The present disclosure is based, in part, on the discovery that lentiviral vectors and packaging cell lines designed to express T-cell/NK-cell activation receptors (as well as optionally other effector proteins) are useful for in vivo expansion of T-cells. Lentiviral vectors and packaging cell lines of the present disclosure may be adapted for transduction and drug-mediated expansion of tumor-infiltrating lymphocytes in vivo, such as when the lentiviral vector is packaged into a lentiviral particle using a packaging cell line and the resulting lentiviral particles are delivered into the body of a subject, such as to a patient suffering from a solid tumor. The lentiviral vectors and particles disclosed can be used for ACT by in vitro transduction of autologous or allogeneic T cells or other immune cells. In some cases, the lentiviral vectors and particles disclosure are configured for use in vivo. Intratumoral injection of lentiviral particles results in in vivo expansion of tumor-infiltrating lymphocytes because the lentiviral vectors are configured to provide expression of T-cell/NK-cell activation receptors capable of providing mitogenic signals to in vitro or in vivo transduced target cells.

1.1 Nucleic Acid Vectors

As used herein, the term "nucleic acid vector" is intended to mean any nucleic acid that functions to carry, harbor, or express a nucleic acid of interest. Nucleic acid vectors can have specialized functions such as expression, packaging, pseudotyping, or transduction. Nucleic acid vectors also can have manipulatory functions if adapted for use as a cloning or shuttle vector. The structure of the vector can include any desired form that is feasible to make and desirable for a particular use. Such forms include, for example, circular forms such as plasmids and phagemids, as well as linear or branched forms. A nucleic acid vector can be composed of, for example, DNA or RNA, as well as contain partially or fully, nucleotide derivatives, analogs and mimetics. Such nucleic acid vectors can be obtained from natural sources, produced recombinantly or chemically synthesized.

Non-limiting examples of vector systems of the present disclosure include a retrovirus, a lentivius, a foamy virus, and a Sleeping Beauty transposon.

1.1.1 Lentiviral Vectors

Lentiviruses are complex retroviruses, which, in addition to the common retroviral genes gag, pol, and env, contain other genes with regulatory or structural function. The higher complexity enables the virus to modulate its life cycle, as in the course of latent infection. Some examples of lentivirus include the Human Immunodeficiency Viruses (HIV-1 and HIV-2) and the Simian Immunodeficiency Virus (SIV). Lentiviral vectors have been generated by multiply attenuating the HIV virulence genes, for example, the genes env, vif, vpr, vpu and nef are deleted, making the vector biologically safe.

Lentiviral vectors offer great advantages for gene therapy. Unless engineered to be non-integrating, lentiviral vectors integrate stably into chromosomes of target cells, permitting long-term expression of delivered transgenes. Further, they do not transfer viral genes therefore avoiding the problem of generating transduced cells that can be destroyed by cytotoxic T-cells. Furthermore, they have a relatively large cloning capacity, sufficient for most envisioned clinical applications. In addition, lentiviruses, in contrast to other retroviruses, are capable of transducing non-dividing cells. This is very important in the context of gene-therapy for tissues such as the hematopoietic system, the brain, liver, lungs and muscle. For example, vectors derived from HIV-1 allow efficient in vivo and ex vivo delivery, integration and stable expression of transgenes into cells such a neurons, hepatocytes, and myocytes (Blomer et al., 1997; Kafri et al., 1997; Naldini et al., 1996; Naldini et al., 1998).

Lentiviral vectors are known in the art, see Naldini et al. (1996) *Science* 272:263-7; Zufferey et al. (1998) *J. Virol.* 72:9873-9880; Dull et al. (1998) *J. Virol.* 72:8463-8471; U.S. Pat. No. 6,013,516; and U.S. Pat. No.5,994,136, which are each incorporated herein by reference in its entirety. In general, these vectors are configured to carry the essential sequences for selection of cells containing the vector, for incorporating foreign nucleic acid into a lentiviral particle, and for transfer of the nucleic acid into a target cell.

A commonly used lentiviral vector system is the so-called third-generation system. Third-generation lenvrial vector systems include four plasmids. The "transfer plasmid" encodes the polynucleotide sequence that is delivered by the lentiviral vector system to the target cell. The transfer plasmid generally has one or more transgene sequences of interest flanked by long terminal repeat (LTR) sequences, which facilitate integration of the transfer plasmid sequences into the host genome. For safety reasons, transfer plasmids are generally designed to make the resulting vector replication incompetent. For example, the transfer plasmid lacks gene elements necessary for generation of infective particles in the host cell. In addition, the transfer plasmid may be designed with a deletion of the 3' LTR, rendering the virus "self-inactivating" (SIN). See Dull et al. (1998) *J. Virol.* 72:8463-71; Miyoshi et al. (1998) *J. Virol.* 72:8150-57.

Third-generation systems also generally include two "packaging plasmids" and an "envelope plasmid." The "envelope plasmid" generally encodes an Env gene operatively linked to a promoter. In an exemplary third-generation system, the Env gene is VSV-G and the promoter is the CMV promoter. The third-generation system uses two packaging plasmids, one encoding gag and pol and the other encoding rev as a further safety feature—an improvement over the single packaging plasmid of so-called second-generation systems. Although safer, the third-generation system can be more cumbersome to use and result in lower viral titers due to the addition of an additional plasmid. Exemplary packing plasmids include, without limitation, pMD2.G, pRSV-rev, pMDLG-pRRE, and pRRL-GOI.

Lentiviral vector systems rely on the use of a "packaging cell line." In general, the packaging cell line is a cell line whose cells are capable of producing infectious lentiviral particles when the transfer plasmid, packaging plasmid(s), and envelope plasmid are introduced into the cells. Various methods of introducing the plasmids into the cells may be used, including transfection or electroporation. In some cases, a packaging cell line is adapted for high-efficiency packaging of a lentiviral vector system into lentiviral particles.

As used herein, the term "lentiviral vector" is intended to mean a nucleic acid that encodes a lentiviral cis nucleic acid sequence required for genome packaging. A lentiviral vector also can encode other cis nucleic acid sequences beneficial for gene delivery, including for example, cis sequences required for reverse transcription, proviral integration or genome transcription. A lentiviral vector performs transduction functions of a lentiviral vector. As such, the exact makeup of a vector genome will depend on the genetic material desired to be introduced into a target cell. Therefore, a vector genome can encode, for example, additional polypeptides or functions other than that required for packaging, reverse transcription, integration, or transcription. Such functions generally include coding for cis elements required for expression of a nucleic acid of interest. The lentiviral cis sequences or elements can be derived from a lentivirus genome or other virus or vector genome so long as the lentiviral vector genome can be packaged by a packaging cell line into a lentiviral particle and introduced into a target cell.

Non-limiting examples of lentiviral vectors include SEQ ID NOs: 6-11, which are illustrated in FIGS. 6-11.

Figure 1B:
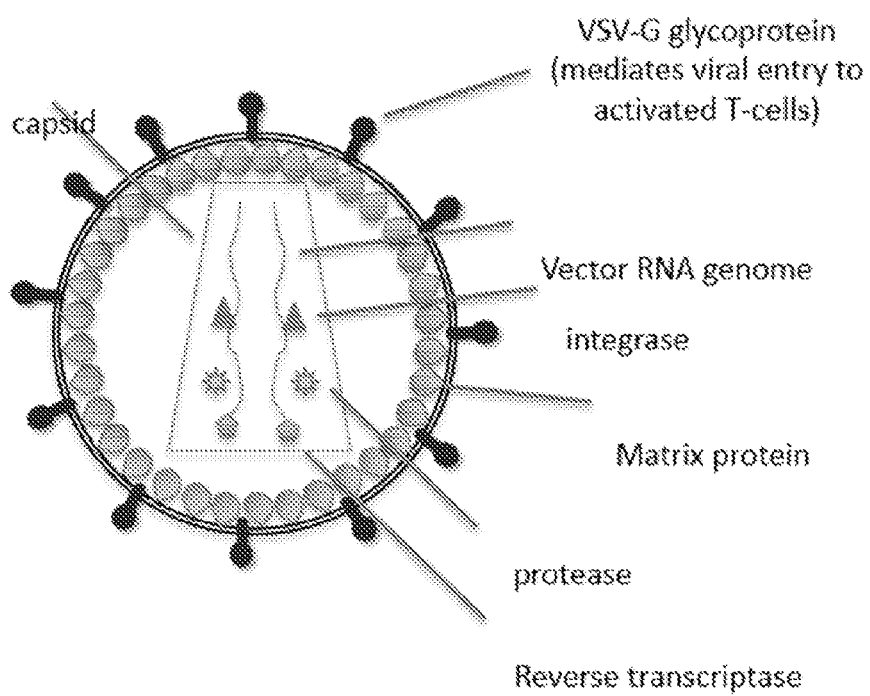

The lentiviral particles produced generally include an RNA genome (derived from the transfer plasmid), a lipid-bilayer envelope in which the Env protein is embedded, and other accessory proteins including integrase, protease, and matrix protein (see FIG. 1B). As used herein, the term "lentiviral particle" is intended to mean a viral particle that includes an envelope, has one or more characteristics of a lentivirus, and is capable of invading a target host cell. Such characteristics include, for example, infecting non-dividing host cells, transducing non-dividing host cells, infecting or transducing host immune cells, containing a lentiviral virion including one or more of the gag structural polypeptides p7, p24, and p17, containing a lentiviral envelope including one or more of the env encoded glycoproteins p41, p120, and p160, containing a genome including one or more lentivirus cis-acting sequences functioning in replication, proviral integration or transcription, containing a genome encoding a lentiviral protease, reverse transcriptase or integrase, or containing a genome encoding regulatory activities such as Tat or Rev. The transfer plasmids may comprise a cPPT sequence, as described in U.S. Pat. No. 8,093,042.

The efficiency of the system is an important concern in vector engineering. The efficiency of a lentiviral vector system may be assessed in various ways known in the art, including measurement of vector copy number (VCN) or vector genomes (vg) such as by quantitative polymerase chain reaction (qPCR), or titer of the virus in infectious units per milliliter (IU/mL). For example, the titer may be assessed using a functional assay performed on the cultured tumor cell line HT1080 as described in Humbert et al. Development of Third-generation Cocal Envelope Producer Cell Lines for Robust Lentiviral Gene Transfer into Hematopoietic Stem Cells and T-cells. *Molecular Therapy* 24:1237-1246 (2016). When titer is assessed on a cultured cell line that is continually dividing, no stimulation is required and hence the measured titer is not influenced by surface engineering of the lentiviral particle. Other methods for assessing the efficiency of lentiviral vector systems are provided in Gaererts et al. Comparison of lentiviral vector titration methods. *BMC Biotechnol.* 6:34 (2006).

It is widely known that lentiviral vector systems have limited efficiency and that attempts to alter the lentiviral vector system often result in decreased efficency. The present inventors have surprisingly discovered that the envelope plasmid of lentiviral vector systems (e.g. a third-generation system) can be modified to encode a plurality of polypeptides in addition to the fusion glycoprotein or functional variant thereof.

In some cases, the vectors and packaging cell lines of the disclosure are capable of generating surface-engineered lentiviral particles at titres of at least about $1\times10^6$ IU/mL, at least about $2\times10^6$ IU/mL, at least about $3\times10^6$ IU/mL, at least about $4\times10^6$ IU/mL, at least about $5\times10^6$ IU/mL, at least about $6\times10^6$ IU/mL, at least about $7\times10^6$ IU/mL, at least about $8\times10^6$ IU/mL, at least about $9\times10^6$ IU/mL, or at least about $1\times10^7$ IU/mL. In some cases, the multicistronic vectors of the disclosure are capable of generating surface-engineered lentiviral particles at titres of at least about $1\times10^7$ IU/mL, at least about $2\times10^7$ IU/mL, at least about $3\times10^7$ IU/mL, at least about $4\times10^7$ IU/mL, at least about $5\times10^7$ IU/mL, at least about $6\times10^7$ IU/mL, at least about $7\times10^7$ IU/mL, at least about $8\times10^7$ IU/mL, at least about $9\times10^7$ IU/mL, or at least about $1\times10^8$ IU/mL.

1.2 T-Cell/NK-Cell Activation Receptors

The disclosure contemplates nucleic acid vectors, lentiviral vectors, and AAV vectors that encode T-cell/NK-cell activation receptors. As used herein, the term "T-cell/NK-cell activation receptors" refers to one or more transmembrane proteins that are configured to be expressed on the cell surface of transduced cells such that the T-cell/NK-cell activation receptor provides a mitogenic signal to the transduced cell. A T-cell/NK-cell activation receptor is used because the target cells are, in most cases, T cells or NK cells. The present methods can be adapted for use with other cell types by use of an activation receptor that retains activity in another cell type. T-cell/NK-cell activation receptors useful here may include a signaling domain that is a cytokine receptor signaling domain, a co-stimulatory receptor signaling domain, a T-cell receptor subunit signaling domain, an NK-cell receptor subunit signaling domain, a growth factor receptor signaling domain, or the like.

1.2.1 Non-Limiting Examples of T-Cell/NK-Cell Activation Receptors

The signaling domain used may be that of a common cytokine receptor gamma chain or that of a common cytokine receptor beta chain. The signaling domain may include an ITAM or a tyrosine capable of binding an SH2-domain when the tyrosine is phosphorylated. In some cases, signaling may be triggered by homo- or heterodimerization of the activation receptor. Phosphorylation of one or more tyrosine residues on an intracellular domain of an activation receptor may, in some cases, lead to dimerization with an SH2 domain and thereby initiate a mitogenic signaling cascade. In some cases a signaling domain of the present disclosure may be capable of being phosphorylated on a tyrosine residue and thereafter binding to an SH2 domain on another molecule.

In some cases, the T-cell/NK-cell activation receptor is a naturally occurring activation receptor. Alternatively, a composite of one or more gene elements taken from different activation receptors known in the art. Examples of engineered T-cell/NK-cell activation receptors useful in the present invention include, without limitation, constitutively active IL2 receptors or IL7 receptors, as described in Hunter et al. Chimeric γc cytokine receptors confer cytokine independent engraftment of human T lymphocytes. Mol Immunol. 2013 November; 56(1-2):1-11.; Shum et al. Constitutive Signaling from an Engineered IL7 Receptor Promotes Durable Tumor Elimination by Tumor-Redirected T Cells. Cancer Discov. 2017 November; 7(11):1238-1247.

1.2.2 Small-Molecule Controllable T-Cell/NK-Cell Activation Receptors

It may, in some cases, be advantageous to provide a means to control expansion of transduced cells in the body. In some cases, this could serve as a failsafe to guard again excessive expansion of cells. In other cases, one could control expansion of transduced cells for therapeutic purposes. Thus, the present disclosure provides T-cell/NK-cell activation receptors that are controllable by use of a small molecule. When the lentiviral vector encodes such a controllable T-cell/NK-cell activation receptor, administering the small molecule permits activation of the activation receptor to provide a mitogenic signal to transduced cells, whereas ceasing administration of the small molecule prevents the activation receptor from providing a mitogenic signal to transduced cells. In this way, in vivo TILs generated by administering the lentiviral particles to a subject will expand only while the small molecule is present in the subject. The small molecule can be provided systemically or locally and concurrently with or during the period after administration of the lentiviral particle. Expansion of TILs can be monitored through blood samples, biopsy, or medical imaging, and the small molecule withdrawn if excessive expansion is observed. In some cases, pulsed or intermittent administration of the small molecule may used to optimize the treatment protocol. In some cases, the small molecule will be titrated to tune TIL expansion. In some cases, the small molecule may be withdrawn or administered in response to remission or relapse of the tumor or for other therapeutic reasons.

In some cases, T-cell/NK-cell activation receptors may be configured to be controllable by a small molecule by substitution of the extracellular domains of a dimeric T-cell/NK-cell activation receptor with protein subunits that inducibly dimerize in the presence of a small molecule, or that inducibly dimerize in the absence of a small molecule and return to monomeric state upon removal, degradation, or dilution of the small molecule. It is contemplated that in the case of a heterodimeric T-cell/NK-cell activation receptor, the T-cell/NK-cell activation receptor may be modified so that the extracellular domain of one unit of the T-cell/NK-cell activation receptor comprises one monomer of the protein subunits that inducibly dimerize, and the extracellular domain of the other unit of the T-cell/NK-cell activation receptor comprises the other monomer of the protein subunits that inducibly dimerize. A heterodimeric T-cell/

NK-cell activation receptor may be modified in this manner using either a homodimeric protein subunits that inducibly dimerize or heterodimeric protein subunits that inducibly dimerize. In other cases, a homodimeric T-cell/NK-cell activation receptor may be modified in this manner using either homodimeric protein subunits that inducibly dimerize or heterodimeric protein subunits that inducibly dimerize. The small-molecule controllable T-cell/NK-cell activation receptor may be encoded by a single transgene if it is homodimeric or by two transgenes when it is heterodimeric.

Examples of protein subunits that inducibly dimerize include, without limitation, FK506-binding protein (FKBP) and the FKBP12-rapamycin binding (FRB) domain. FK506-binding protein dimerizes in the presence tacrolimus (FK506). FKBP12-rapamycin binding (FRB) domain dimerizes in the presence of rapamycin. Thus, the small molecule according to the present disclosure may be either tacrolimus, rapamycin, or a rapalog (a rapamycin analog). Further examples of small molecules by which small-molecule controllable receptors can be controlled include, without limitation, rapamycin, a rapalog, coumermycin, gibberellin, abscisic acid (ABA), methotrexate, cyclosporin A, FKCsA, trimethoprim (Tmp)-synthetic ligand for FKBP (SLF), or any derivatives thereof. Exemplary pairs of domains that suitable as fusion proteins in the receptors of the present disclosure include, without limitation, a pair selected from FKBP and FRB, FKBP and calcineurin, FKBP and cyclophilin, FKBP and bacterial DHFR, calcineurin and cyclophilin, PYL1 and ABI1, or GIB1 and GAI, or variants thereof.

In some cases, the small-molecule controllable receptor comprises an extracellular domain comprises one or more small-molecule binding domains. Binding for the small-molecule to the extracellular domain(s) causes intramolecular interaction of receptor molecules (e.g. homodimerization or heterodimerization), thus activating a downstream signal from the intracellular domain(s). The intracellular domain(s) of small-molecule controllable receptor may comprise one or more domains selected from domains or fragments of CD28, OX-40, 4-1BB/CD137, CD2, CD7, CD27, CD30, CD40, Programmed Death-1 (PD-1), inducible T cell co-stimulator (ICOS), lymphocyte function-associated antigen-1 (LFA-1, CD1-1a/CD18), CD3 gamma, CD3 delta, CD3 epsilon, CD3 zeta, CD247, CD276 (B7-H3), LIGHT, (TNFSF14), NKG2C, Ig alpha (CD79a), DAP-10, Fc gamma receptor, MHC class 1 molecule, TNF receptor proteins, an Immunoglobulin protein, cytokine receptor, integrins, Signaling Lymphocytic Activation Molecules (SLAM proteins), activating NK cell receptors, BTLA, a Toll ligand receptor, ICAM-1, B7-H3, CDS, ICAM-1, GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL-2R beta, IL-2R gamma, IL-7R alpha, IL-21R alpha, ITGA4, VLA1, CD49a, ITGA4, IA4, CD49D, ITGA6, VLA-6, CD49f, ITGAD, CD1 ld, ITGAE, CD103, ITGAL, CD1 la, LFA-1, ITGAM, CD1 lb, ITGAX, CD1 lc, ITGB1, CD29, ITGB2, CD18, LFA-1, ITGB7, NKG2D, TNFR2, TRANCE/RANKL, DNAM1 (CD226), SLAMF4 (CD244, 2B4), CD84, CD96 (Tactile), CEACAM1, CRT AM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, a ligand that specifically binds with CD83, CD27, CD28, ICOS, 4-1BB, CD40, RANK/TRANCE-R, OX40, TGFbR1, TGFbRII, myd88, CD40 and any other TNF receptor superfamily members, and combinations thereof.

A "homolog" of a protein of interest, such as FKBP or FRB, includes proteins comprising or consisting of an amino acid sequence that has at least about 70%, 80%, 90%, 95%, 98% or 99% identity with the amino acid sequence of the protein. A homolog may also be a protein that is encoded by a nucleic acid that has at least about 70%, 80%, 90%, 95%, 98% or 99% identity with a nucleotide sequence.

A "functional homolog" of a protein of interest refers to a homolog of the protein having at least one biological activity of the protein. For example, a functional homolog of FKPB refers to a homolog of FKBP that heterodimerizes with FRB in the presence of rapamycin (or related rapalogs) or homodimerizes in the presence of molecules such as AP1903; a functional homolog of FRB refers to a homolog of FRB that heterodimerizes with FKBP in the presence of rapamycin (or related rapalogs).

In some embodiments, the T-cell/NK-cell activation receptor comprises (a) a first chain comprising either or both of: (i) a functional FKPB domain that shares at least 95%, 99%, or 100% sequence identity with SEQ ID NO: 13, and (ii) a functional IL2Rb domain that shares at least 95%, 99%, or 100% sequence identity with SEQ ID NO: 14; and/or (b) a second chain comprising either or both of: (i) a functional FRB domain that shares at least 95%, 99%, or 100% sequence identity with SEQ ID NO: 16, and (ii) a functional IL2Rg domain that shares at least 95%, 99%, or 100% sequence identity with SEQ ID NO: 17.

In some embodiments, the T-cell/NK-cell activation receptor comprises (a) a first chain comprising a functional FKPB domain and a functional IL2Rb domain, wherein the first chain shares at least 95%, 99%, or 100% sequence identity with SEQ ID NO: 12; and/or (b) a second chain comprising a functional FRB domain and a functional IL2Rg domain, wherein the second chain shares at least 95%, 99%, or 100% sequence identity with SEQ ID NO: 15.

1.2.3 Chimeric Antigen Receptors

It may, in some cases, be advantageous to provide a means to target transduced cells to particular cells or tissues. In some cases, the lentiviral vector comprises (instead of or in addition to other genes) a polynucleotide encoding a chimeric antigen receptor (CAR). Various CARs known in the art can be employed. Alternatively, T-cell receptor (TCR) fusions can be used. When the vector encodes a CAR, the CAR can comprise one or more domains selected from domain or fragments of CD28, OX-40, 4-1BB/CD137, CD2, CD7, CD27, CD30, CD40, Programmed Death-1 (PD-1), inducible T cell co-stimulator (ICOS), lymphocyte function-associated antigen-1 (LFA-1, CD1-1a/CD18), CD3 gamma, CD3 delta, CD3 epsilon, CD3 zeta, CD247, CD276 (B7-H3), LIGHT, (TNFSF14), NKG2C, Ig alpha (CD79a), DAP-10, Fc gamma receptor, MHC class 1 molecule, TNF receptor proteins, an Immunoglobulin protein, cytokine receptor, integrins, Signaling Lymphocytic Activation Molecules (SLAM proteins), activating NK cell receptors, BTLA, a Toll ligand receptor, ICAM-1, B7-H3, CDS, ICAM-1, GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL-2R beta, IL-2R gamma, IL-7R alpha, IL-21R alpha, ITGA4, VLA1, CD49a, ITGA4, IA4, CD49D, ITGA6, VLA-6, CD49f, ITGAD, CD1 ld, ITGAE, CD103, ITGAL, CD1 la, LFA-1, ITGAM, CD1 lb, ITGAX, CD1 lc, ITGB1, CD29, ITGB2, CD18, LFA-1, ITGB7, NKG2D, TNFR2, TRANCE/RANKL, DNAM1 (CD226), SLAMF4 (CD244, 2B4), CD84, CD96

(Tactile), CEACAM1, CRT AM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, a ligand that specifically binds with CD83, CD27, CD28, ICOS, 4-1BB, CD40, RANK/TRANCE-R, OX40, TGFbR1, TGFbRII, myd88, other TNF receptor superfamily members not already listed, and combinations thereof.

1.2.4 Small-Molecule Controllable Chimeric Antigen Receptors

It may, in some cases, be advantageous to provide a means to control targeted of transduced cells. In some cases, this could serve as a failsafe to guard again excessive activity of cells. In other cases, one could control activity of transduced cells for therapeutic purposes. Thus, the present disclosure provides CARS, or similar targeting receptors e.g. TCR fusions, that are controllable by use of a small molecule. When the lentiviral vector encodes such a controllable targeting receptor, administering the small molecule permits activation of the targeting receptor to target transduced cells to target cells, whereas ceasing administration of the small molecule prevents the receptor from targeting transduced cells to target cells. In this way, in vivo TILs generated by administering the lentiviral particles to a subject will activate only while the small molecule is present in the subject. The small molecule can be provided systemically or locally and concurrently with or during the period after administration of the lentiviral particle. Activity of TILs can be monitored through blood samples, biopsy, or medical imaging, and the small molecule withdrawn if excessive activity is observed. In some cases, pulsed or intermittent administration of the small molecule may used to optimize the treatment protocol. In some cases, the small molecule will be titrated to tune TIL activity. In some cases, the small molecule may be withdrawn or administered in response to remission or relapse of the tumor or for other therapeutic reasons.

In some cases, targetting receptors (e.g. CARs) may be configured to be controllable by a small molecule by fusion to protein subunits that inducibly dimerize in the presence of a small molecule, or that inducibly dimerize in the absence of a small molecule and return to monomeric state upon removal, degradation, or dilution of the small molecule. It is contemplated that in the case of a heterodimeric targeting receptors, the T-cell/NK-cell activation receptor may be modified so that the extracellular domain of one unit of the targeting receptor comprises one monomer of the protein subunits that inducibly dimerize, and the extracellular domain of the other unit of the targeting receptor comprises the other monomer of the protein subunits that inducibly dimerize. A heterodimeric targeting receptor may be modified in this manner using either a homodimeric protein subunits that inducibly dimerize or heterodimeric protein subunits that inducibly dimerize. In other cases, a homodimeric targeting receptor may be modified in this manner using either homodimeric protein subunits that inducibly dimerize or heterodimeric protein subunits that inducibly dimerize. The small-molecule controllable targeting receptor may be encoded by a single transgene if it is homodimeric or by two transgenes when it is heterodimeric.

Examples of protein subunits that inducibly dimerize include, without limitation, FK506-binding protein (FKBP) and the FKBP12-rapamycin binding (FRB) domain. FK506-binding protein dimerizes in the presence tacrolimus (FK506). FKBP12-rapamycin binding (FRB) domain dimerizes in the presence of rapamycin. Thus, the small molecule according to the present disclosure may be either tacrolimus, rapamycin, or a rapalog (a rapamycin analog). Further examples of small molecules by which small-molecule controllable receptors can be controlled include, without limitation, rapamycin, a rapalog, coumermycin, gibberellin, abscisic acid (ABA), methotrexate, cyclosporin A, FKCsA, trimethoprim (Tmp)-synthetic ligand for FKBP (SLF), or any derivatives thereof. Exemplary pairs of domains that suitable as fusion proteins in the receptors of the present disclosure include, without limitation, a pair selected from FKBP and FRB, FKBP and calcineurin, FKBP and cyclophilin, FKBP and bacterial DHFR, calcineurin and cyclophilin, PYL1 and ABI1, or GIB1 and GAI, or variants thereof.

In some cases, the small-molecule controllable targeting receptor comprises an extracellular domain comprising one or more small-molecule binding domains. Binding of the small-molecule to the extracellular domain(s) causes intramolecular interaction of receptor molecules (e.g. homodimerization or heterodimerization), thus activating binding to target cells and/or a downstream signal from the intracellular domain(s). The intracellular domain(s) of small-molecule controllable receptor may comprise one or more domains selected from domains or fragments of CD28, OX-40, 4-1BB/CD137, CD2, CD7, CD27, CD30, CD40, Programmed Death-1 (PD-1), inducible T cell co-stimulator (ICOS), lymphocyte function-associated antigen-1 (LFA-1, CD1-1a/CD18), CD3 gamma, CD3 delta, CD3 epsilon, CD3 zeta, CD247, CD276 (B7-H3), LIGHT, (TNFSF14), NKG2C, Ig alpha (CD79a), DAP-10, Fc gamma receptor, MHC class 1 molecule, TNF receptor proteins, an Immunoglobulin protein, cytokine receptor, integrins, Signaling Lymphocytic Activation Molecules (SLAM proteins), activating NK cell receptors, BTLA, a Toll ligand receptor, ICAM-1, B7-H3, CDS, ICAM-1, GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL-2R beta, IL-2R gamma, IL-7R alpha, IL-21R alpha, ITGA4, VLA1, CD49a, ITGA4, IA4, CD49D, ITGA6, VLA-6, CD49f, ITGAD, CD1 ld, ITGAE, CD103, ITGAL, CD1 la, LFA-1, ITGAM, CD1 lb, ITGAX, CD1 lc, ITGB1, CD29, ITGB2, CD18, LFA-1, ITGB7, NKG2D, TNFR2, TRANCE/RANKL, DNAM1 (CD226), SLAMF4 (CD244, 2B4), CD84, CD96 (Tactile), CEACAM1, CRT AM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, a ligand that specifically binds with CD83, CD27, CD28, ICOS, 4-1BB, CD40, RANK/TRANCE-R, OX40, TGFbR1, TGFbRII, myd88, CD40 and any other TNF receptor superfamily members, and combinations thereof. Further exemplary controllable CARs are provided by U.S. Pat. No. 10,196,444, incorporated herein by reference.

In some embodiments, the two protein subunits that inducibly dimerize are each fused to a transmembrane protein comprising signaling domain(s) and to a binding agent (e.g. single-chain variable fragment, scFv), respectively. The binding agent is capable of specifically binding to a target of interest. Small-molecule induced dimerization reconstitutes a dimeric unit spanning from the binding agent through the dimerized protein subunits to the intracellular signaling domain(s) via the transmembrane region of the transmembrane protein. In some embodiments, two transmembrane proteins are employed and inducible dimerize to one another and to the binding-agent fusion protein in response to one or two small molecules. In some embodiments, the small-molecule controllable CAR comprises two or more binding agent fusion proteins that each individually dimerize to the transmembrane protein comprising signaling domain(s).

1.4 Promoters and Gene Control Elements

The present disclosure further contemplates lentiviral vectors comprising promoters and/or enhancers specific to T-cells, NK cells, or T-cells and NK cells. The present disclosure provides nucleic acid sequences of T-cell and/or NK-cell specific promoters (SEQ ID NOs: 1-4). These can be operatively linked to the T-cell/NK-cell activation receptor generally by inserting the promoter sequence 5' to the gene encoded by the lentiviral vector. The promoter use can be identical to a sequence set forth in SEQ ID NOs: 1-4 or 80%, 85%, 90%, 95%, or 99% identical to a sequence set forth in SEQ ID NOs: 1-4, so long as the promoter retains promoter activity in T and/or NK cells.

In some cases, other promoters can used to control expression of the T-cell/NK-cell activation receptor. Examples of promoter useful in the present disclosure include, without limitation, an MND promoter, a T-cell specific promoter, a CD4 T-cell specific promoter, a CD8 T-cell specific promoter, an NK-cell specific promoter, a T-cell and NK-cell specific promoter, a CD4 T-cell and NK-cell specific promoter, and a CD8 T-cell and NK-cell specific promoter.

In some cases, a "strong" promoter is used. It will be understood that the strength of a promoter is determined in part by the attributes of the cell in which it operates. In some cases, the strong promoter of the present disclosure results in high-level expression of gene elements to which it is operatively linked in a target cell, such as a TIL. Strong promoters include, without limitation, cytomegalovirus (CMV) and murine stem cell virus (MSCV), phosphoglycerate kinase (PGK), a promoter sequence comprised of the CMV enhancer and portions of the chicken beta-actin promoter and the rabbit beta-globin gene (CAG), promoter sequence comprised of portions of the SV40 promoter and CD43 promoter (SV40/CD43), and a synthetic promoter that contains the U3 region of a modified MoMuLV LTR with myeloproliferative sarcoma virus enhancer (MND). Exemplary strong promoters useful in the compositions and method of the present disclosure are provided by Jones et al. Lentiviral vector design for optimal T cell receptor gene expression in the transduction of peripheral blood lymphocytes and tumor-infiltrating lymphocytes. Hum Gene Ther. 2009 June; 20(6): 630-40.

In some cases, the strong promoter may be a synthetic strong promoter. Exemplary synthetic strong promoters are provided by Schlabach et al. (2010) *Proc Natl Acad Sci USA*. 10:2538-2543. In some cases, other promoters are used. In some cases, any promoter active in the packaging cell line is used. In some cases, an inducible promoter is used, e.g. a drug-inducible promoter.

In some cases, vectors of the present disclosure may comprise the Woodchuck Hepatitis Virus Posttranscriptional Regulatory Element (wPRE) or a nucleic acid sequence substantially identical to wPRE. See U.S. Pat. No. 6,136, 597; Lee et al. (2005) *Exp Physiol.* 90:33-7. Variants of the wPRE element with reduced size are known in the art. wPRE-O refers to a variant of wPRE with the intermediate size In some cases, lentiviral vectors of the present disclosure may comprise a polynucleotide sequence encoding the 2A peptide. The term "2A peptide" refers to a self-cleaving peptide configured to generate two or more proteins from a single open reading frame. 2A peptides are 18-22 residue-long viral oligopeptides that mediate "cleavage" of polypeptides during translation in eukaryotic cells. "2A peptide" may refer to peptides with various amino acid sequences. In the present disclosure it will be understood that where a lentiviral vector comprises two or more 2A peptides, the 2A peptides may be identical to one another or different. Detailed methodology for design and use of 2A peptides is provided by Szymczak-Workman et al. (2012) *Cold Spring Harb. Protoc.* 2012:199-204. In the literature, 2A peptides are often refered to as self-cleaving peptides, but mechanistic studies have shown that the "self-cleavage" observed is actually a consequence of the ribosome's skipping the formation of the glycyl-prolyl peptide bond at the C terminus of the 2A peptide. Donnelly et al. (2001) *J Gen Virol.* 82:1027-41.

In some cases, lentiviral vectors of the present disclosure may comprise the Woodchuck Hepatitis Virus Posttranscriptional Regulatory Element (wPRE) or a nucleic acid sequence substantially identical to wPRE. See Lee et al. Optimizing regulatable gene expression using adenoviral vectors. Exp Physiol. 90 (1): 33-7 (2005). In the viral vectors of the present disclosure, the wPRE sequence increases expression of genes delivered by said viral vectors.

1.5 Fusion Glycoproteins

Various fusion glycoproteins can be used to pseudotype lentiviral vecotrs. While the most commonly used example is the envelope glycoprotein from vesicular stomatitis virus (VSVG), many other viral proteins have also been used for pseudotyping of lentiviral vectors. See Joglekar et al. (2017) *Human Gene Therapy Methods* 28:291-301. The present disclosure contemplates substitution of various fusion glycoproteins. Notably, some fusion glycoproteins result in higher vector efficiency.

In some embodiments, pseudotyping a fusion glycoprotein or functional variant thereof facilitates targeted transduction of specific cell types, including, but not limited to, T cells or NK-cells. In some embodiments, the fusion glycoprotein or functional variant thereof is/are full-length polypeptide(s), functional fragment(s), homolog(s), or functional variant(s) of Human immunodeficiency virus (HIV) gp160, Murine leukemia virus (MLV) gp70, Gibbon ape leukemia virus (GALV) gp70, Feline leukemia virus (RD114) gp70, Amphotropic retrovirus (Ampho) gp70, 10A1 MLV (10A1) gp70, Ecotropic retrovirus (Eco) gp70, Baboon ape leukemia virus (BaEV) gp70, Measles virus (MV) H and F, Nipah virus (NiV) H and F, Rabies virus (RabV) G, Mokola virus (MOKV) G, Ebola Zaire virus (EboZ) G, Lymphocytic choriomeningitis virus (LCMV) GP1 and GP2, Baculovirus GP64, Chikungunya virus (CHIKV) E1 and E2, Ross River virus (RRV) E1 and E2, Semliki Forest virus (SFV) E1 and E2, Sindbis virus (SV) E1 and E2, Venezualan equine encephalitis virus (VEEV) E1 and E2, Western equine encephalitis virus (WEEV) E1 and E2, Influenza A, B, C, or D HA, Fowl Plague Virus (FPV) HA, Vesicular stomatitis virus VSV-G, or Chandipura virus and Piry virus CNV-G and PRV-G. In some cases, the fusion glycoprotein or functional variant thereof is a full-length polypeptide, functional fragment, homolog, or functional variant of the G protein of Vesicular Stomatitis Alagoas Virus (VSAV), Carajas Vesiculovirus (CJSV), Chandipura Vesiculovirus (CHPV), Cocal Vesiculovirus (COCV), Vesicular Stomatitis Indiana Virus (VSIV), Isfahan Vesiculovirus (ISFV), Maraba Vesiculovirus (MARAV), Vesicular Stomatitis New Jersey virus (VSNJV), Bas-Congo Virus (BASV). In some embodiments, the fusion glycoprotein or functional variant thereof is the Cocal virus G protein.

1.6 Checkpoint-Inhibiting Ligands

In some cases, the lentiviral vectors of the present disclosure further comprise a nucleic acid sequence encoding a checkpoint-inhibiting ligand. Optionally, the checkpoint-inhibiting ligand is capable of blocking the PD-1/PD-L1 checkpoint. Optionally, the checkpoint-inhibiting ligand is capable of blocking the Tim-3 checkpoint.

Checkpoint inhibitor therapy is a form of cancer treatment that uses agents to stimulate or inhibit immune checkpoints and thereby modulate the immune response. Tumors may use checkpoints to protect themselves from the immune system of the subject or from therapeutic agents used in cancer immunotherapy. The present disclosure provides a lentiviral vector comprising a nucleic acid sequence encoding a checkpoint-inhibiting ligand, wherein lentiviral particles produced from the lentiviral vector display the checkpoint-inhibiting ligand on their surface, and therefore administration of the lentiviral particle results in delivery of the checkpoint-inhibiting ligand to the subject at the site of therapeutic use. The present disclosure further provides lentiviral vectors comprising a nucleic acid sequence encoding a checkpoint-inhibiting ligand, wherein administration of lentiviral particles produced from the lentiviral vector delivers the polynucleotide sequence to target cells, which then express the checkpoint-inhibiting ligand at the site of therapeutic use.

Examples of checkpoint-inhibitor ligands provided by the present disclosure include, without limitation, anti-CTLA-4 antibody, anti-PD-1 antibodies, and anti-PD-L1 antibodies or any non-antibody ligands (e.g. nanobodies, DARPins) that interact with CTLA4, PD-1, or PD-L1 respectively. In some cases, the checkpoint-inhibiting ligand is capable of blocking the PD-1/PD-L1 checkpoint and/or the Tim-3 checkpoint and/or the CTLA-4 checkpoint. Use of checkpoint inhibition is reviewed in, e.g., Anderson et al. Tim-3: an emerging target in the cancer immunotherapy landscape. Cancer Immunol Res. 2014 May; 2(5):393-8.

1.5 Resistance to Immunosuppressive Drugs

In some cases, the lentiviral vectors of the present disclosure further comprises a nucleic acid sequence (e.g., on the transfer plasmid) that provides resistance to a immunosuppressive drug. A nucleic acid sequence that provides resistance to a immunosuppressive drug will, in some cases, facilitate selective expansion of target cells when the immunosuppressive drug is administered to a patient during any of the methods for treating a subject or any of the methods for expanding T-cells capable of recognizing and killing tumor cells in a subject in need thereof provided by the present disclosure. In some cases, the immunosuppressive drug is methotrexate, rapamycin, a rapalog, tacrolimus, cyclosporine, or any combination thereof. The immunosuppressive drug may be the same as the small molecule or different, that is the lentiviral vector may be designed so that the small-molecule controllable T-cell/NK-cell activation receptors is induced by an immunosuppressive drug such that whenever the immunosuppressive drug is administered to the subject, expansion of transduced cells is triggered. Alternatively, it may be advantageous to design the lentiviral vector to permit control of transduced-cell expansion independent of immunosuppression.

In some cases, the lentiviral vector facilitates selective expansion of target cells by conferring resistance to an immunosuppressive drug to transduced cells, facilitates selective expansion of target cells. The present disclosure provides lentiviral vectors that comprise any of the nucleic sequences that confer resistance to an immunosuppressive drug known in the art. Examples of immunosuppressive drugs include, without limitation, rapamycin or a derivative thereof, a rapalog or a derivative thereof, tacrolimus or a derivative thereof, cyclosporine or a derivative thereof, methotrexate or derivatives thereof, and mycophenolate mofetil (MMF) or derivatives thereof. Various resistance genes are known in the art. Resistance to rapamycin may be conferred by a polynucleotide sequence encoding the protein domain FRb, found in the mTOR domain and known to be the target of the FKBP-rapamycin complex. Resistance to tacrolimus may be conferred by a polynucleotide sequence encoding the calcineurin mutant CNa22 or calcineurin mutant CNb30. Resistance to cyclosporine may be conferred by a polynucleotide sequence encoding the calcineurin mutant CNa12 or calcineurin mutant CNb30. These calcineurin mutants are described in Brewin et al. (2009) *Blood* 114:4792-803. Resistance to methotrexate can be provided by various mutant forms of di-hydrofolate reducatse (DHFR), see Volpato et al. (2011) *J Mol Recognition* 24:188-198, and reistance to MMF can be provided by various mutant forms of inosine monophosphate dehydrogenase (IMPDH), see Yam et al. (2006) *Mol Ther* 14:236-244.

Immunosuppressive drugs are commonly used prior to, during, and/or after ACT. In some cases, use of an immunosuppressive drug may improve treatment outcomes. In some cases, use of an immunosuppressive drug may diminish side effects of treatment, such as, without limitation, acute graft-versus-host disease, chronic graft-versus-host disease, and post-transplant lymphoproliferative disease. The present disclosure contemplates use of immunosuppressive drugs with any of the methods of treating or preventing a disease or condition of the present disclosure, including, without limitation, methods of the present disclosure in which the lentiviral vector confers resistance to an immunosuppressive drug to transduced cells.

2.1 Packaging Cell Lines

In another aspect, the present disclosure provides packaging cell lines for generating lentiviral particles capable of activating and efficiently transducing T cells, comprising cultured cells capable of packaging a lentivirus vector, wherein the cultured cells are genetically engineered to express a T-cell activation or co-stimulation molecule, or are induced to transiently express a T-cell activation or co-stimulation molecule via transient transfection. The packaging cell lines of the present disclosure may be used with any lentiviral vector including but not limited to those previously described. In some cases, it will be advantageous to use the packaging cell line with a lentiviral vector comprising a nucleic acid sequence encoding a T-cell/NK-cell activation receptor. In some cases, it will be advantageous for that T-cell/NK-cell activation receptor to be capable of being activated by a small molecule. But the packaging cell lines disclosed can be used with other lentiviral vectors as well.

In some cases, the packaging cell line is a HEK-293T cell line. Similar results can be achieved with other cell lines, including, without limitation, HEK-293T cell lines engineered to be deficient in B2M or other immunologically active surface proteins. Other cell lines that are transfectable in vitro and capable of high titer lentiviral vector production cand be used—e.g., cell lines that comprise the gene sequence for polyoma virus large T antigen operatively linked to a promoter.

The packaging cell line may be, in some cases, genetically modified to lack MHC class I expression, MHC class II expression, or expression of inhibitory checkpoint ligands, such as PD-L1 (a PD-1 ligand), or ligands for TIM3. As expression of inhibitory ligands by the packaging cell line could limit T-cell activation by the lentiviral particles, these genetic modification serve in some cases to eliminate such inhibitory signals, further promoting T-cell activation and transduction by the lentiviral particles.

In some cases, a packaging cell line is genetically engineered to comprise one or more genes useful in packing lentiviral vectors into lentiviral particles. In some cases, a packaging cell line may comprise polynucleotide sequences encoding the genes gag-pol, env, and rev. In a typical lentiviral vector of the present invention, at least part of one or more of the gag-pol and env protein coding regions may be removed from the lentiviral vector and provided by the packing cell line. Lentiviral vectors may be packaged according to the methods provided in Dull et al. (1998) *J Virol* 72:8463-71, which is incorporated herein in its entirety. Exemplary packaging cell lines are provide in *Retroviruses*. Cold Spring Harbour Laboratory (Coffin et al., eds) (1997).

The present disclosure further provides for genetically engineering the packaging cell line to improve immunological attributes of the lentiviral vectors and particles of the present disclosure in other ways, including, without limitation, adding genes, deleting genes, and introducing point mutations into genes.

2.2 T-Cell Activation or Co-Simulation Molecules

Conventionally, lentiviral transduction in vitro requires additional of an exogenous activating agent, such as a "stimbead," for example Dynabeads™ Human T-Activator CD3/CD28. Lentiviral particles made using the packaging cell lines of the present disclosure incorporate one or more copies of the T-cell activation or co-stimulation molecule that is expressed by the packaging cell line into the lentiviral particle; and the incorporation of T-cell activation or co-stimulation molecule(s) in the lentiviral particle renders the lentiviral particle capable of activating and efficiently transducing T cells in the absence of an exogenous activating agent, i.e. without a stimbead or equivalent agent. This permits the lentiviral particles made from these packaging cell lines to be used in vivo in cases in which exogenous delivery of an activating agent may be impractical.

In some cases, the T-cell activation or co-stimulation molecule may be selected from the group consisting of an anti-CD3 antibody, CD28 ligand (CD28L), and 41bb ligand (41BBL or CD137L). Various T-cell activation or co-stimulation molecules are known in the art and include, without limitation, agents that specifically bind any of the T-cell expressed proteins CD3, CD28, CD134 also known as OX40, or 41bb also known as 4-1BB or CD137 or TNFRSF9. For example, an agent that specifically binds CD3 may be an anti-CD3 antibody (e.g., OKT3, CRIS-7 or I2C) or an antigen-binding fragment of an anti-CD3 antibody. In some aspects, an agent that specifically binds CD3 is a single chain Fv fragment (scFv) of an anti-CD3 antibody. In some cases, the present disclosure contemplates that the T-cell activation or co-stimulation molecule is selected from the group consisting of an anti-CD3 antibody, CD28 ligand (CD28L), and 41bb ligand (41BBL or CD137L). CD86 also known as B7-2 is a ligand for both CD28 and CTLA-4. In case cases, a CD28L may be CD86. CD80 is an additional ligand for CD28. In some cases, the ligand for CD28 is CD80. In some cases, the ligand for CD28 is an anti-CD28 antibody or an anti-CD28 scFv fused to a transmembrane domain for display on the surface of the lentiviral particle. Lentiviral particles comprising one or more a T-cell activation or co-stimulation molecules may be made by methods provided by WO2016/139463.

3 Lentiviral Particles

In another aspect the present disclosure further provides lentiviral particles comprising any of the lentiviral vectors of the present disclosure. The lentiviral particles of the present disclosure can be made with the packaging cell lines of the present disclosure, or with another packaging cell line, or by co-transfection of cultured cells, e.g. HEK-293T cells, with the lentiviral vector and helper plasmids. The lentiviral particles of the present disclosure can be prepared by, for example, transducing any of the lentiviral vectors of the present disclosure into cultured cells genetically engineered to express a T-cell activation or co-stimulation molecule. In some cases, due to the lentiviral vector, to the packaging cell line chosen, or to co-transfected helper plasmids, the lentiviral particle will comprise a T-cell activation or co-stimulation molecule, which molecule could be, without limitation, an anti-CD3 antibody, an CD28 ligand, or 41bb ligand. The cultured cells genetically engineered to express a T-cell activation or co-stimulation molecule could be HEK-293T cells. In some cases, the cultured cells are genetically modified to lack MHC class I expression, MHC class II expression, or expression of inhibitory checkpoint ligands, such as PD-L1 (a PD-1 ligand), or ligands for TIM3.

4 Methods of Use

In another aspect, the disclosure provides methods for treating a subject suffering from cancer, comprising administering any lentiviral particle of the present disclosure to the subject, and administering the small molecule to the subject, wherein the cancer is treated in the subject.

In some embodiments, the disclosure provides a surface-engineered lentiviral particle for use in therapy. In other embodiments, the disclosure provides a surface-engineered lentiviral particle for use in a method of treating a cancer. In further embodiments, the disclosure provides a surface-engineered lentiviral particle for use in the manufacture of a medicament for treating cancer.

In some cases, the cancer is a solid tumor, such as a melanoma, non-small cell lung cancer, or breast cancer. The methods of the present disclosure may include treating any cancer, including, without limitation, acute granulocytic leukemia, acute lymphocytic leukemia, acute myelogenous leukemia, adenocarcinoma, adenosarcoma, adrenal cancer, adrenocortical carcinoma, anal cancer, anaplastic astrocytoma, angiosarcoma, appendix cancer, astrocytoma, basal cell carcinoma, B-cell lymphoma, bile duct cancer, bladder cancer, bone cancer, bone marrow cancer, bowel cancer, brain cancer, brain stem glioma, brain tumor, breast cancer, carcinoid tumors, cervical cancer, cholangiocarcinoma, chondrosarcoma, chronic lymphocytic leukemia, chronic myelogenous leukemia, colon cancer, colorectal cancer, craniopharyngioma, cutaneous lymphoma, cutaneous melanoma, diffuse astrocytoma, ductal carcinoma in situ, endometrial cancer, ependymoma, epithelioid sarcoma, esophageal cancer, Ewing sarcoma, extrahepatic bile duct cancer, eye cancer, fallopian tube cancer, fibrosarcoma, gallbladder cancer, gastric cancer, gastrointestinal cancer, gastrointestinal carcinoid cancer, gastrointestinal stromal tumors, general, germ cell tumor, gestational trophoblastic disease, glioblastoma multiforme, glioma, hairy cell leukemia, head and neck cancer, hemangioendothelioma, Hodgkin lymphoma, Hodgkin lymphoma, Hodgkin's disease, hypopharyngeal cancer, infiltrating ductal carcinoma, infiltrating lobular carcinoma, inflammatory breast cancer, intestinal cancer, intrahepatic bile duct cancer, invasive/infiltrating breast cancer, islet cell cancer, jaw cancer, kaposi sarcoma, kidney cancer, laryngeal cancer, leiomyosarcoma, leptomeningeal metastases, leukemia, lip cancer, liposarcoma, liver cancer, lobular carcinoma in situ, low-grade astrocytoma, lung cancer, lymph node cancer, lymphoma, male breast cancer, medullary carcinoma, medulloblastoma, melanoma, meningioma, Merkel cell carcinoma, mesenchymal chondrosarcoma, mesenchymous, mesothelioma, metastatic breast cancer, metastatic melanoma, metastatic squamous neck cancer, mixed gliomas, mouth cancer, mucinous carcinoma, mucosal melanoma, multiple myeloma, mycosis fungoides, myelodysplastic syndrome, nasal cavity cancer, nasopharyngeal cancer, neck cancer, neuroblastoma, neuroendocrine tumors, non-Hodgkin lymphoma, non-Hodgkin's lymphoma, non-small cell lung cancer, oat cell cancer, ocular cancer, ocular melanoma, oligodendroglioma, oral cancer, oral cavity cancer, oropharyngeal cancer, osteogenic sarcoma, osteosarcoma, ovarian cancer, ovarian epithelial cancer, ovarian germ cell tumor, ovarian primary peritoneal carcinoma, ovarian sex cord stromal tumor, paget's disease, pancreatic cancer, papillary carcinoma, paranasal sinus cancer, parathyroid cancer, pelvic cancer, penile cancer, peripheral nerve cancer, peritoneal cancer, pharyngeal cancer, pheochromocytoma, pilocytic astrocytoma, pineal region tumor, pineoblastoma, pituitary tumors, primary central nervous system, prostate cancer, rectal cancer, renal cell carcinoma, renal pelvis cancer, rhabdomyosarcoma, salivary gland cancer, sarcoma, sarcoma, bone, sarcoma, soft tissue, sarcoma, uterine, sinus cancer, skin cancer, small cell lung cancer, small intestine cancer, soft tissue sarcoma, spinal cancer, spinal column cancer, spinal cord cancer, spinal tumor, squamous cell carcinoma, stomach cancer, synovial sarcoma, t-cell lymphoma, testicular cancer, throat cancer, thymoma/thymic carcinoma, thyroid cancer, tongue cancer, tonsil cancer, transitional cell cancer, transitional cell cancer, transitional cell cancer, triple-negative breast cancer, tubal cancer, tubular carcinoma, undiagnosed cancer, ureteral cancer, ureteral cancer, urethral cancer, uterine adenocarcinoma, uterine cancer, uterine sarcoma, vaginal cancer, vulvar cancer.

In another aspect, the disclosure provides a method for expanding T-cells capable of recognizing and killing tumor cells in a subject in need thereof, including the steps of administering a lentiviral particle of the disclosure to the subject, such that T-cells capable of recognizing and killing tumor cells in the subject are transduced by the lentiviral particle and expanded. In some embodiments, the lentiviral particle is administered by intravenous injection or by intratumoral injection.

In some cases, the lentiviral particle comprises a targeting agent or the nucleic acid vector encodes a targeting agent. Exemplary targeting agents include antibodies and chimeric antigen receptors ("CAR"). The term "antibody" refers to an intact antigen-binding immunoglobulin of any kind, or a fragment thereof that itself specifically binds to the antibody's target antigen, and includes, for example, chimeric, humanized, fully human, and bispecific antibodies. The CAR used in the present disclosure in some cases comprises a binding domain which is specific for B-cells, e.g., specific for a CD-marker that can be found on B-cell lymphoma such as CD19, CD22, CD20 or CD79a, CD19 being preferred. T-cells that have been genetically engineered to express a CAR (e.g., a T-cell CAR) are exemplified in WO2007/131092. The targeting agent serves, in some cases, to direct cell-mediated immunity towards other particular cell types, such as tumor cells.

In another aspect, the disclosure provides methods for expanding T-cells capable of recognizing and killing tumor cells in a subject in need thereof, comprising administering any lentiviral particle of the present disclosure to the subject, and administering the small molecule to the subject, wherein T-cells capable of recognizing and killing tumor cells in the subject are expanded.

In certain embodiments, a subject treated by the methods described herein may be a mammal. In some cases, a subject is a human, a non-human primate, a pig, a horse, a cow, a dog, a cat, a rabbit, a mouse or a rat. A subject may be a human female or a human male.

Combination therapies are also contemplated by the invention. Combination as used herein includes simultaneous treatment or sequential treatment. Combinations of methods of the invention with standard medical treatments (e.g., corticosteroids) are specifically contemplated, as are combinations with novel therapies. In some cases, a subject may be treated with a steroid (e.g. prednisone, prednisolone, deflazacort) to prevent or to reduce an immune response to administration of a lentiviral particle described herein. In certain cases, a subject may receive apheresis or another immune modulator if the subject expresses antibodies to the lentiviral particle described herein. In some cases, such immune modulators may be unnecessary, particularly when an immunosuppressive agent (e.g. tacrolimus or sirolimus) is administered. In some cases, rituxan is administered simultaneous to or sequential with treatment with a lentiviral particles. Rituxan may in some cases serve to block immune responses against the lentiviral particles The lentiviral particles, small molecules, and immunosuppressive drugs of the present disclosure may be administered by any route, including oral, nasal, intravenous, intra-arterial, intramuscularly, or intraperitoneal routes. In some cases, the lentiviral particle is administered by intravenous injection or by intratumoral injection. In some cases, the small molecule is administered by intravenous injection or administered orally. In some cases, the small molecule is administered at concentrations sufficient to activate the T-cell/NK-cell activation receptor. In some cases, the small molecule is rapamycin, optionally administered at concentrations sufficient to maintain serum concentrations of rapamycin greater than 0.1 nM, 1 nM, or 10 nM. In some cases, the small molecule is a rapalog, optionally administered at concentrations sufficient to maintain serum concentrations of the rapalog greater than 0.1 nM, 1 nM, or 10 nM. In some cases, the small molecule is capable of causing dimerization of the T-cell/NK-cell activation receptor resulting in a cell activation signal.

In some cases, the small molecule is administered simultaneously with the lentiviral particle; or the small molecule is administered about 30 minutes, about 1 hour, about 2 hours, about 4 hours, about 5 hours or about 10 hours before or after the lentiviral particle is administered. In some cases, the method further comprises administering to the subject an immunosuppressive agent. In some cases, the immunosuppressive agent is tacrolimus, optionally administered at concentrations sufficient to maintain serum concentrations of tacrolimus greater than 0.1 nM, 1 nM, or 10 nM. In some cases, the immunosuppressive agent is cyclosporine, optionally administered at concentrations sufficient to maintain serum concentrations of cyclosporine greater than 0.1 nM, 1 nM, or 10 nM. In some cases, the immunosuppressive agent is an immunosuppressive drug. In some cases, the immunosuppressive agent is an immunosuppressive drug and the lentiviral vector comprises a nucleic acid sequence encoding a protein that provides resistance to said immunosuppressive drug The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating actions of microorganisms such as bacteria and fungi. The carrier can be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating such as lecithin, by the maintenance of the required particle size in the case of a dispersion and by the use of surfactants. The prevention of the action of microorganisms can be brought about by various antibacterial and antifungal agents, for example, parabens, chlorobutanol, phenol, sorbic acid, thimerosal and the like. In many cases it will be preferable to include isotonic agents, for example, sugars or sodium chloride. Prolonged absorption of the injectable compositions can be brought about by use of agents delaying absorption, for example, aluminum monostearate and gelatin.

Sterile injectable solutions are prepared by incorporating rAAV in the required amount in the appropriate solvent with various other ingredients enumerated above, as required. The injectable solutions may be prepared aseptically or filter-sterilized.

5 Definitions

Unless defined otherwise, all technical and scientific terms used herein have the same meaning as commonly understood by those of ordinary skill in the art to which the invention belongs. For the purposes of the present invention, the following terms are defined below.

As used herein, "293T control particles" or "Mock (293T vector)" refer to lentiviral particles generated by transduction of 293T cells with a lentiviral vector. As used herein, "stimbeads" refers to a bead-based reagent used to stimulate T-cells during transduction. The label "+Control (vector +stimbeads)" refers transduction with 293T control particles with stimbeads.

As used herein, the term "HATSE cells" or "HATSE cell line" or "HATSE-293" refers a packaging cell line created by transducing 293T cells with lentiviral vector(s) encoding CD86 and CD137L and subjected to fluorescence-activated cell sorting (FACS) for cells that highly expressed both CD86 and CD137L one or more times. The label "(1× sorted)HATSE cell vector" refers to lentiviral particles generated by transduction of HATSE cells with a lentiviral vector after the HATSE cells are FACS-sorted for CD86$^+$/CD173L$^+$ double-positive cells one time. The label "(2× sorted)HATSE cell vector refers to lentiviral particles generated by transduction of HATSE cells with a lentiviral vector after the HATSE cells are FACS-sorted for CD86$^+$/CD173L$^+$ double-positive cells one time.

The articles "a," "an," and "the" are used herein to refer to one or to more than one (i.e. to at least one) of the grammatical object of the article. By way of example, "an element" means one element or more than one element.

The use of the alternative (e.g., "or") should be understood to mean either one, both, or any combination thereof of the alternatives.

The term "and/or" should be understood to mean either one, or both of the alternatives.

As used herein, the term "about" or "approximately" refers to a quantity, level, value, number, frequency, percentage, dimension, size, amount, weight or length that varies by as much as 15%, 10%, 9%, 8%, 7%, 6%, 5%, 4%, 3%, 2% or 1% to a reference quantity, level, value, number, frequency, percentage, dimension, size, amount, weight or length. In one embodiment, the term "about" or "approximately" refers a range of quantity, level, value, number, frequency, percentage, dimension, size, amount, weight or length ±15%, ±10%, ±9%, ±8%, ±7%, ±6%, ±5%, ±4%, ±3%, ±2%, or ±1% about a reference quantity, level, value, number, frequency, percentage, dimension, size, amount, weight or length.

Any concentration range, percentage range, ratio range, or integer range is to be understood to include the value of any integer within the recited range and, when appropriate, fractions thereof (such as one tenth and one hundredth of an integer), unless otherwise indicated. The term "about", when immediately preceding a number or numeral, means that the number or numeral ranges plus or minus 10%.

Throughout this specification, unless the context requires otherwise, the words "comprise", "comprises" and "comprising" will be understood to imply the inclusion of a stated step or element or group of steps or elements but not the exclusion of any other step or element or group of steps or elements. In particular embodiments, the terms "include," "has," "contains," and "comprise" are used synonymously.

By "consisting of" is meant including, and limited to, whatever follows the phrase "consisting of." Thus, the phrase "consisting of" indicates that the listed elements are required or mandatory, and that no other elements may be present.

By "consisting essentially of" is meant including any elements listed after the phrase, and limited to other elements that do not interfere with or contribute to the activity or action specified in the disclosure for the listed elements.

Reference throughout this specification to "one embodiment," "an embodiment," "a particular embodiment," "a related embodiment," "a certain embodiment," "an additional embodiment," or "a further embodiment" or combinations thereof means that a particular feature, structure, or characteristic described in connection with the embodiment is included in at least one embodiment of the present invention. Thus, the appearances of the foregoing phrases in various places throughout this specification are not necessarily all referring to the same embodiment. Furthermore, the particular features, structures, or characteristics may be combined in any suitable manner in one or more embodiments.

As used herein, the term "isolated" means material that is substantially or essentially free from components that normally accompany it in its native state. In particular embodiments, the term "obtained" or "derived" is used synonymously with isolated.

A "subject," "patient" or "individual" as used herein, includes any animal that exhibits pain that can be treated with the vectors, compositions, and methods contemplated herein. Suitable subjects (e.g., patients) include laboratory animals (such as mouse, rat, rabbit, or guinea pig), farm animals, and domestic animals or pets (such as a cat or dog). Non-human primates and, preferably, human patients, are included.

As used herein "treatment" or "treating," includes any beneficial or desirable effect associated with treatment. "Treatment" does not necessarily indicate complete eradication or cure of the disease or condition, or associated symptoms thereof.

As used herein, "prevent," and similar words such as "prevented," "preventing" etc., indicate an approach for preventing, inhibiting, or reducing the likelihood of the occurrence or recurrence of the disorder. As used herein, "prevention" and similar words also includes reducing the intensity, effect, symptoms and/or burden of the disease or disorder prior to onset or recurrence.

As used herein, "therapeutically effective amount" or "amount effective" or "effective amount" of a virus or lentiviral particle refers to the amount of the virus or lentiviral particle required to achieve a beneficial or desired prophylactic or therapeutic result, including clinical results.

A "prophylactically effective amount" refers to an amount of a virus or lentiviral particle effective to achieve the desired prophylactic result. Typically but not necessarily, since a prophylactic dose is used in subjects prior to or at an earlier stage of disease, the prophylactically effective amount is less than the therapeutically effective amount.

A "therapeutically effective amount" of a virus or lentiviral particle may vary according to factors such as the disease state, age, sex, and weight of the individual, and the ability of the stem and progenitor cells to elicit a desired response in the individual. A therapeutically effective amount is also one in which any toxic or detrimental effects of the virus are outweighed by the therapeutically beneficial effects. The term "therapeutically effective amount" includes an amount that is effective to "treat" a subject (e.g., a patient).

An "increased" or "enhanced" amount of a physiological response, e.g., electrophysiological activity or cellular activity, is typically a "statistically significant" amount, and may include an increase that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) the level of activity in an untreated subject.

A "decrease" or "reduced" amount of a physiological response, e.g., electrophysiological activity or cellular activity, is typically a "statistically significant" amount, and may include an decrease that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) the level of activity in an untreated subject.

By "maintain," or "preserve," or "maintenance," or "no change," or "no substantial change," or "no substantial decrease" refers generally to a physiological response that is comparable to a response caused by either vehicle, or a control molecule/composition. A comparable response is one that is not significantly different or measurable different from the reference response.

"Receptor-ligand binding," "ligand binding," and "binding" are used interchangeably herein to mean physical interaction between a receptor and a ligand or a synthetic ligand. Ligand binding can be measured by a variety of methods known in the art (e.g., detection of association with a radioactively labeled ligand).

As used herein, the terms "specific binding affinity" or "specifically binds" or "specifically bound" or "specific binding" are used interchangeably throughout the specification and claims and refer to that binding which occurs between a paired species of molecules, e.g., receptor and ligand. When the interaction of the two species produces a non-covalently bound complex, the binding which occurs is typically electrostatic, hydrogen-bonding, or the result of lipophilic interactions. In various embodiments, the specific binding between one or more species is direct. In one embodiment, the affinity of specific binding is about 2 times greater than background binding (non-specific binding), about 5 times greater than background binding, about 10 times greater than background binding, about 20 times greater than background binding, about 50 times greater than background binding, about 100 times greater than background binding, or about 1000 times greater than background binding or more.

In general, "sequence identity" or "sequence homology" refers to an exact nucleotide-to-nucleotide or amino acid-to-amino acid correspondence of two polynucleotides or polypeptide sequences, respectively. Typically, techniques for determining sequence identity include determining the nucleotide sequence of a polynucleotide and/or determining the amino acid sequence encoded thereby, and comparing these sequences to a second nucleotide or amino acid sequence. Two or more sequences (polynucleotide or amino acid) can be compared by determining their "percent identity." The percent identity of two sequences, whether nucleic acid or amino acid sequences, is the number of exact matches between two aligned sequences divided by the length of the shorter sequences and multiplied by 100. Percent identity may also be determined, for example, by comparing sequence information using the advanced BLAST computer program, including version 2.2.9, available from the National Institutes of Health. The BLAST program is based on the alignment method of Karlin and Altschul, Proc. Natl. Acad. Sci. USA 87:2264-2268 (1990) and as discussed in Altschul, et al., J. Mol. Biol. 215:403-410 (1990); Karlin And Altschul, Proc. Natl. Acad. Sci. USA 90:5873-5877 (1993); and Altschul et al., Nucleic Acids Res. 25:3389-3402 (1997). Briefly, the BLAST program defines identity as the number of identical aligned symbols (generally nucleotides or amino acids), divided by the total number of symbols in the shorter of the two sequences. The program may be used to determine percent identity over the entire length of the proteins being compared. Default parameters are provided to optimize searches with short query sequences in, for example, with the blastp program. The program also allows use of an SEG filter to mask-off segments of the query sequences as determined by the SEG program of Wootton and Federhen, Computers and Chemistry 17:149-163 (1993). Ranges of desired degrees of sequence identity are approximately 80% to 100% and integer values therebetween. Typically, the percent identities between a disclosed sequence and a claimed sequence are at least 80%, at least 85%, at least 90%, at least 95%, or at least 98%.

The term "exogenous" is used herein to refer to any molecule, including nucleic acids, protein or peptides, small molecular compounds, and the like that originate from outside the organism. In contrast, the term "endogenous" refers to any molecule that originates from inside the organism (i.e., naturally produced by the organism).

The term "MOI" is used herein to refer to multiplicity of infection, which is the ratio of agents (e.g. viral particles) to infection targets (e.g. cells).

All publications and patents mentioned herein are hereby incorporated by reference in their entirety as if each individual publication or patent was specifically and individually indicated to be incorporated by reference. In case of conflict, the present application, including any definitions herein, will control. However, mention of any reference, article, publication, patent, patent publication, and patent application cited herein is not, and should not be taken as an acknowledgment, or any form of suggestion, that they constitute valid prior art or form part of the common general knowledge in any country in the world.

The section headings used herein are for organizational purposes only and are not to be construed as limiting the subject matter described.

The invention is further described in the following Examples, which do not limit the scope of the invention described in the claims.

EXAMPLES

Example 1

HATSE-293 Packaging Cell Line

Figure 2:
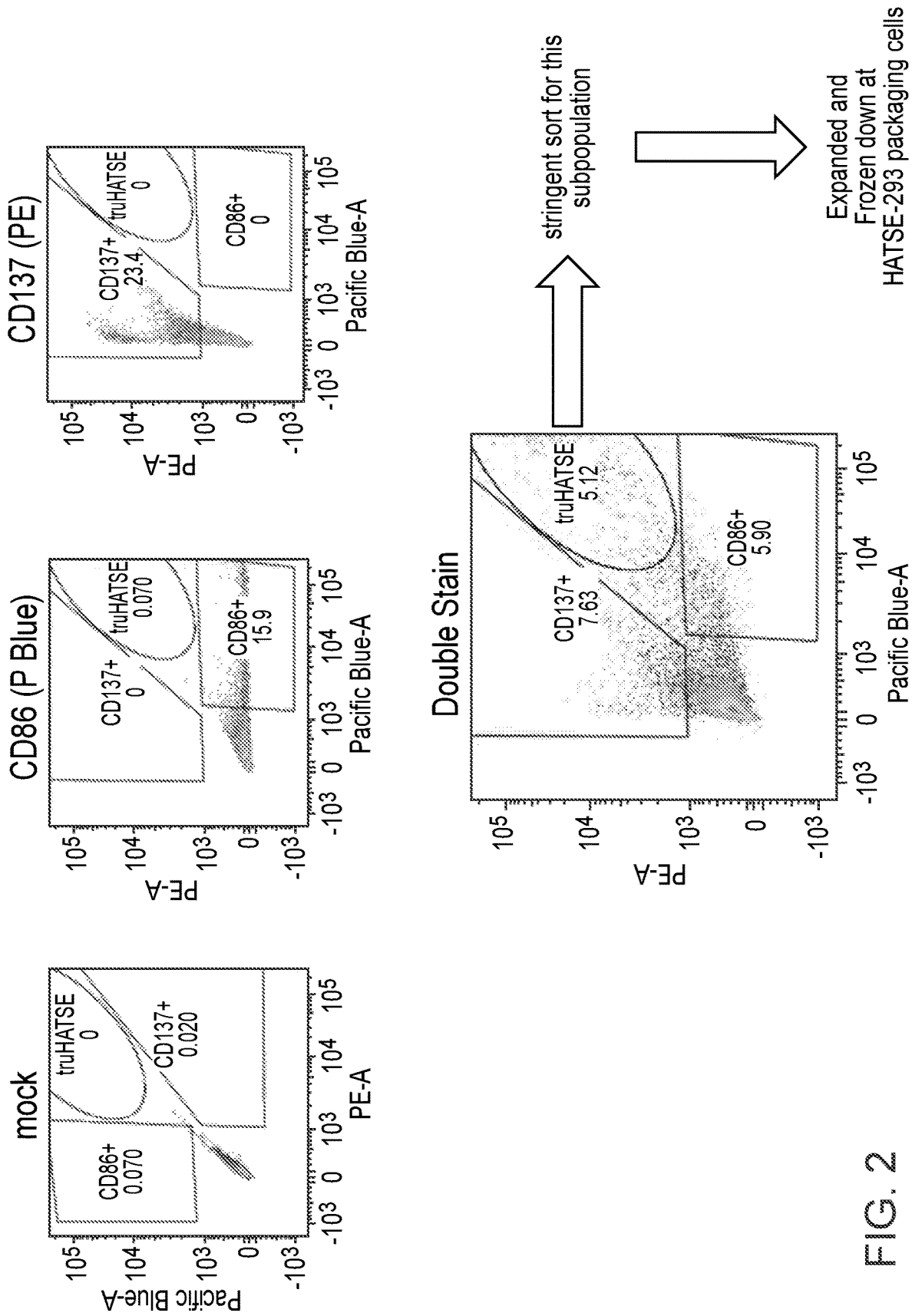
FIG. 2 depicts the experimental protocol used to generate HATSE-293 packaging cell line from HEK-293T cells transduced with a lentiviral vector encoding anti-CD3 scFV, CD86, and CD137L. $CD86^+CD137L^+$ were isolated by fluorescence-activated cell sorting, expanded, and frozen for long-term storage and use.
Figure 3A:
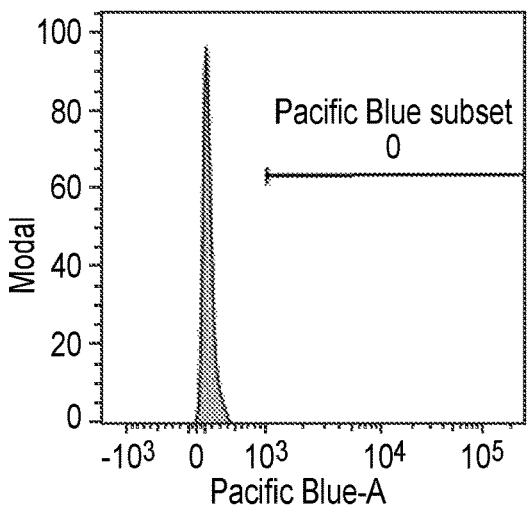
FIGS. 3A-3K depict FACS analysis of parental 293 cells and the HATSE-293 packaging cell line for CD46 (expected constitutive expression on both cell lines), and $CD86^{+/}CD137L^+$ expression (expression expected only in the HATSE-293 cell line).
Figure 3B:
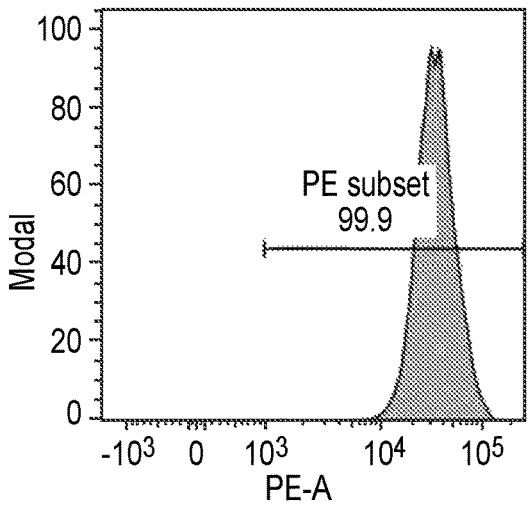
Figure 3C:
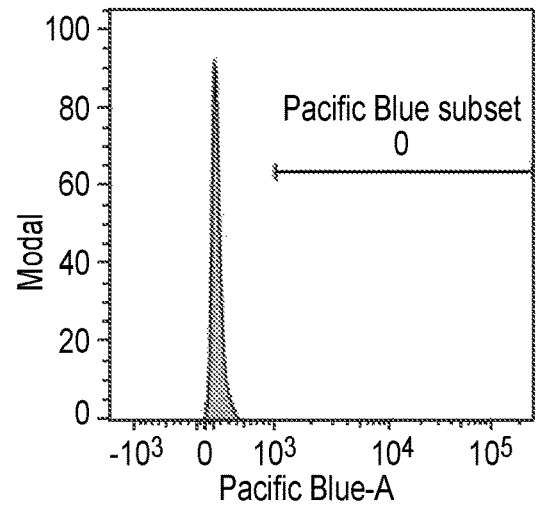
Figure 3D:
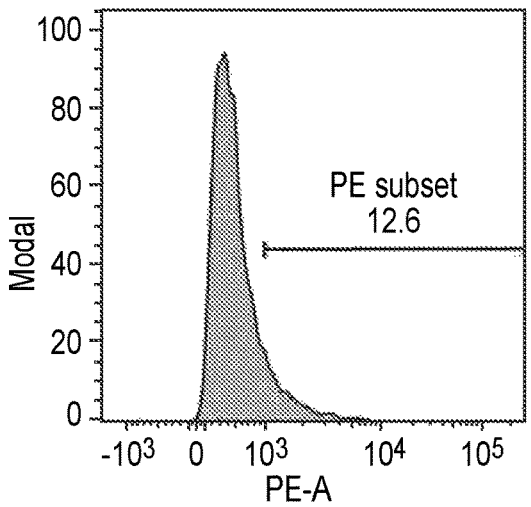
Figure 3E:
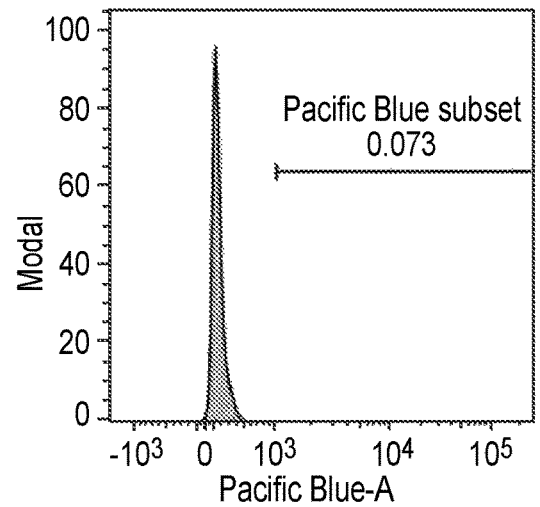
Figure 3F:
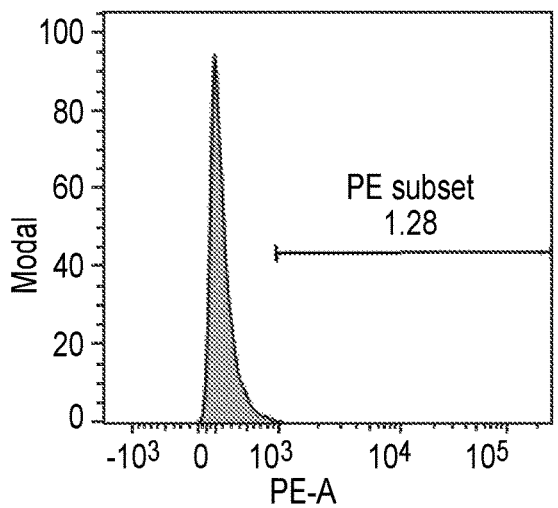
Figure 3G:
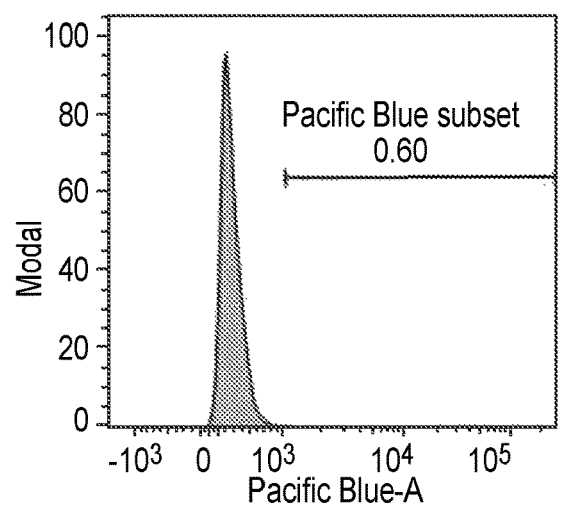
Figure 3H:
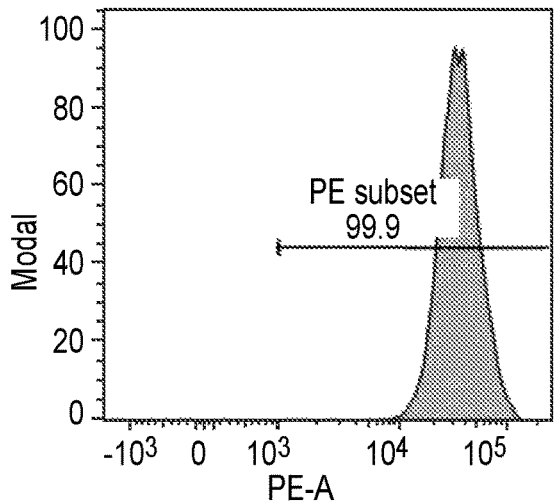
Figure 3I:
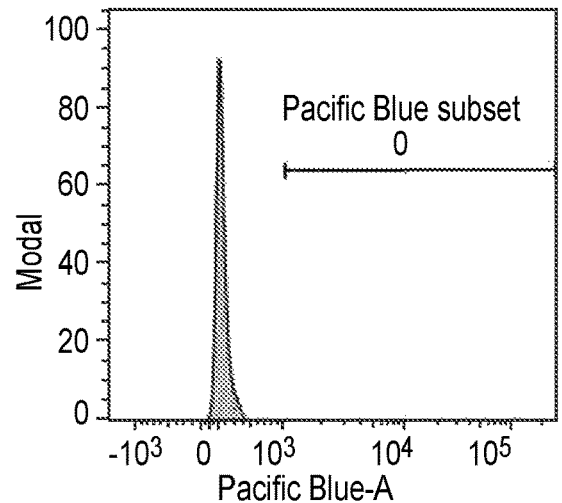
Figure 3J:
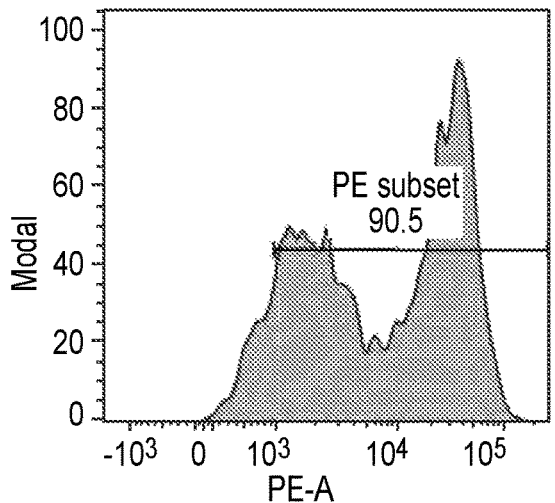
Figure 3K:
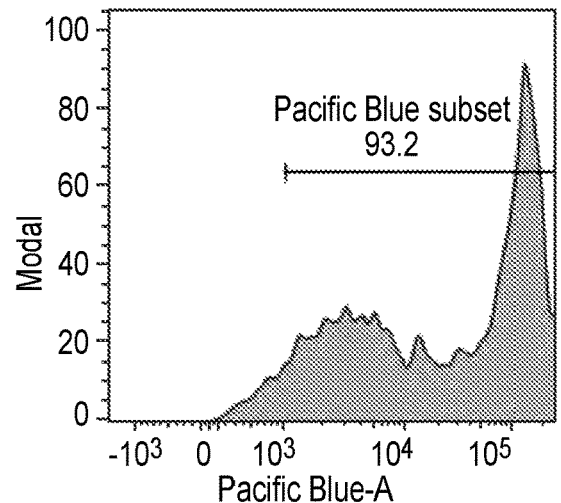

A packaging cell line for generating lentiviral particles capable of activating and efficiently transducing T cells, termed HATSE-293, was generated as follows. A lentiviral vector was constructed comprising the MND promoter and a 2A peptide-linked multicistronic open reading frame encoding an anti-CD3 single chain Fv fragment (scFv) of the monoclonal antibody OKT3; CD86; and CD137L (anti-CD3scFV-2A-CD86-2A-CD137L). The lentiviral vector was transduced into HEK-293T cells grown in cell culture, resulting in stable integration of the MND promoter and multicistronic open reading frame into the genome of host cells. The transduced HEK-293T cells were subjected to fluorescence-activated cell sorting (FACS) for cells that highly expressed both CD86 and CD137L (FIG. 2). Due to the structure of the multicistronic open reading frame, CD86$^+$/CD137L$^+$ cells also necessarily express the anti-CD3 scFv$^+$. The CD86$^+$/CD137L$^+$ cell population was expanded in culture to produce the HATSE-293 packing cell line and aliquots were frozen for long-term storage and use. The expression of CD86 and CD137 were confirmed by flow cytometry (FIG. 3).

HATSE-293 cells were co-transfected with the pMND-GFP lentiviral vector and four lentiviral packaging plasmids (pMD2.G, pRSV-rev, pMDLG-pRRE, and pRRL-GOI), and viral particles were harvested from the cell supernatant to produce lentiviral particles (termed HATSE particles). As a control, HEK-293T cells were co-transfected with the pMND-GFP lentiviral vector and four lentiviral packaging plasmids (pMD2.G, pRSV-rev, pMDLG-pRRE, and pRRL-GOI), and viral particles were harvested from the cell supernatant to produce lentiviral particles (293T control particles).

Figure 4:
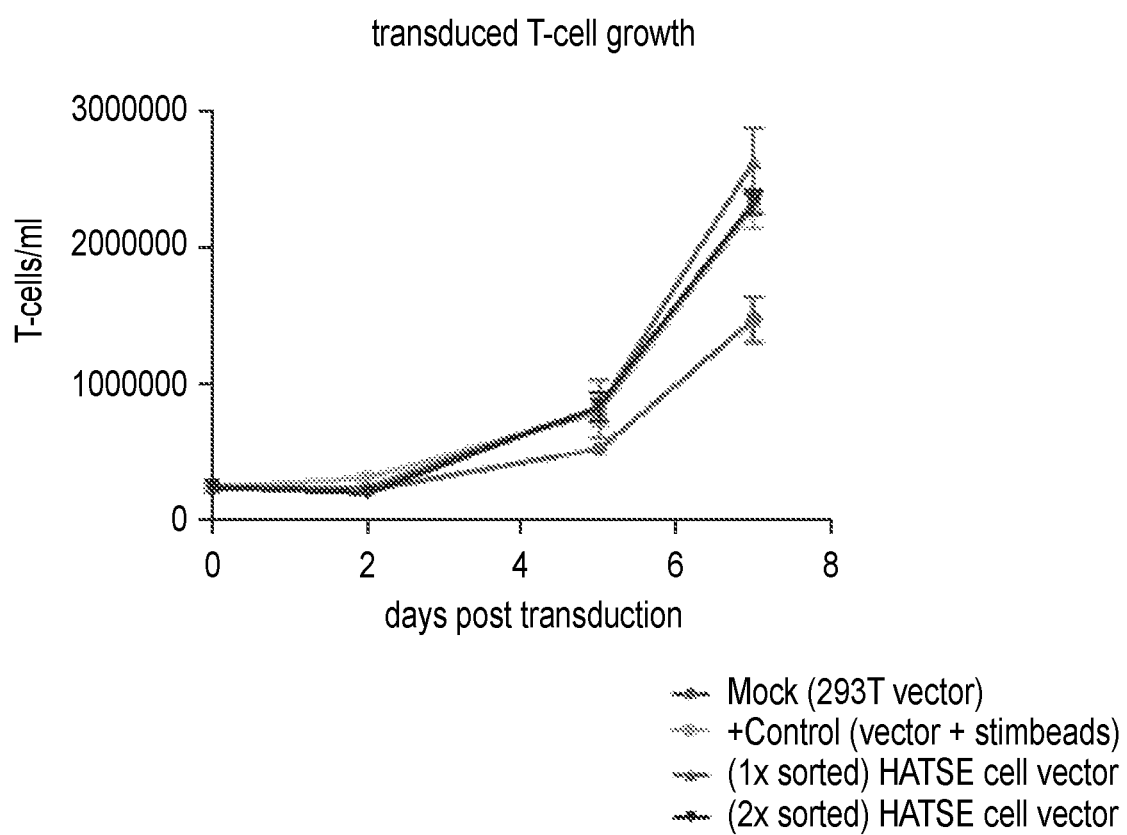
FIG. 4 depicts growth curves of T-cells transduced by control lentiviral particles or lentiviral particles generated from the HATSE cell lines described in the definitions and examples that follow. As a positive control, T-cells were transduced with control lentiviral particles in the presence of stimbeads. "Days post transduction" refers to the number of days elapsed after the day on which the cells were exposed to particles (day 0).
Figure 5:
FIG. 5 depicts fluorescence micrographs of cells exposed to 293T control particles [293T no stim]; 293T control particles and stimbeads [293T stim]; 1× sorted HATSE particles [1× sorted HATSE (no stim)]; or 2× sorted HATSE particles [2× sorted HATSE (no stim)].
Figure 5:
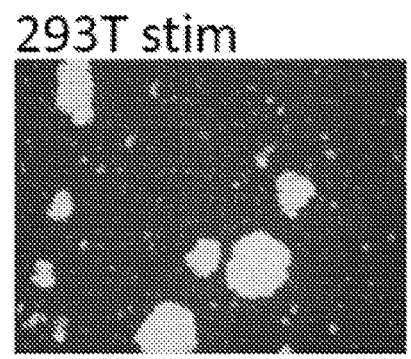
Figure 5:
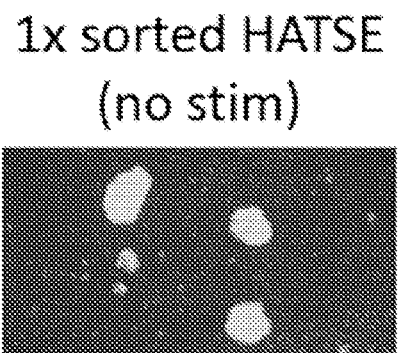
Figure 5:
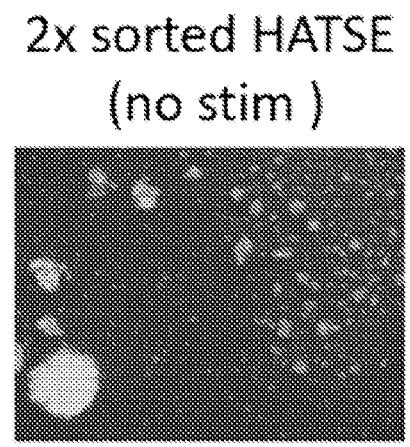
Figure 6:
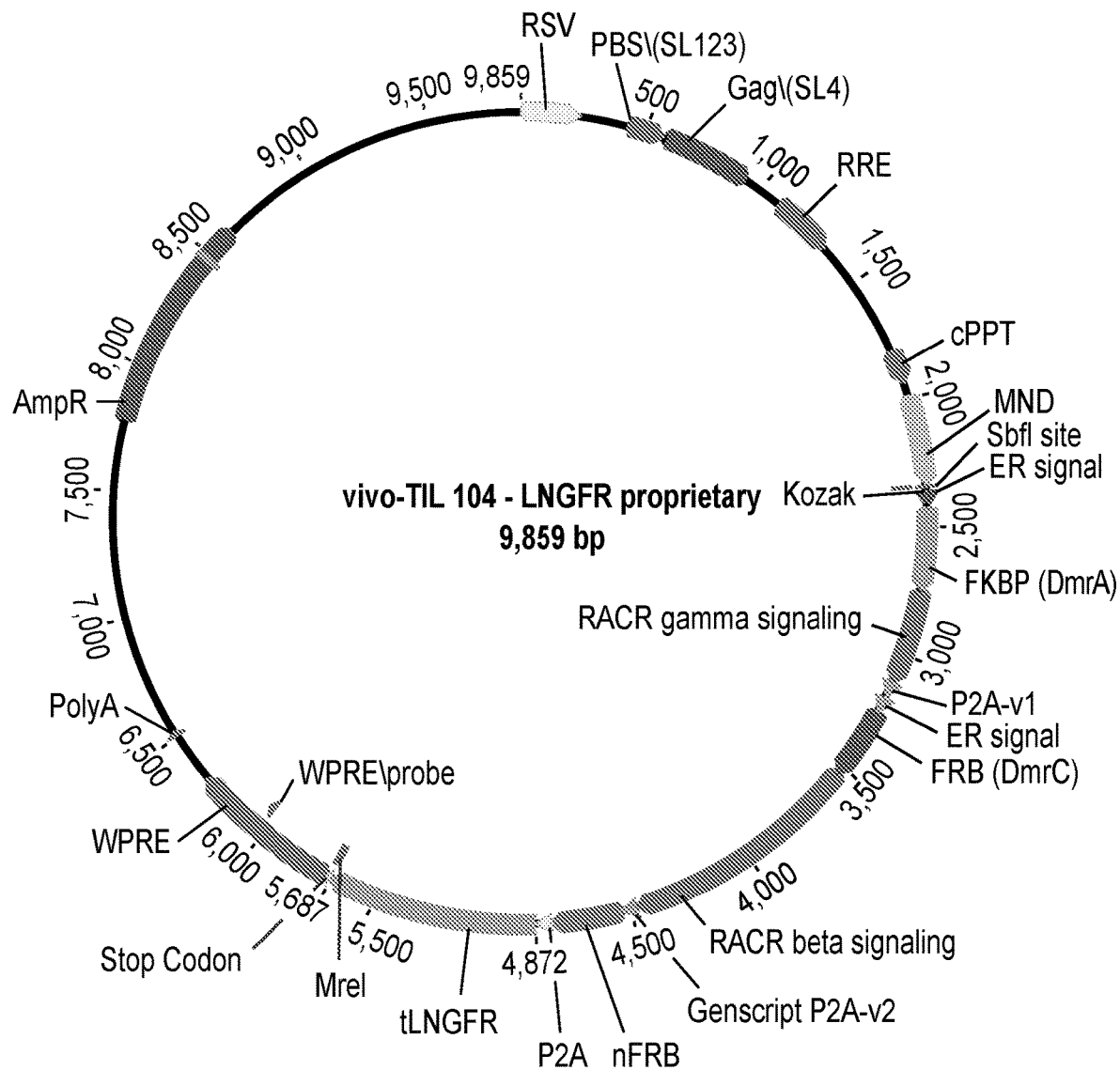
FIG. 6 depicts a vector map for vivo-TIL 104 LNGFR (SEQ ID NO: 6).
Figure 7:
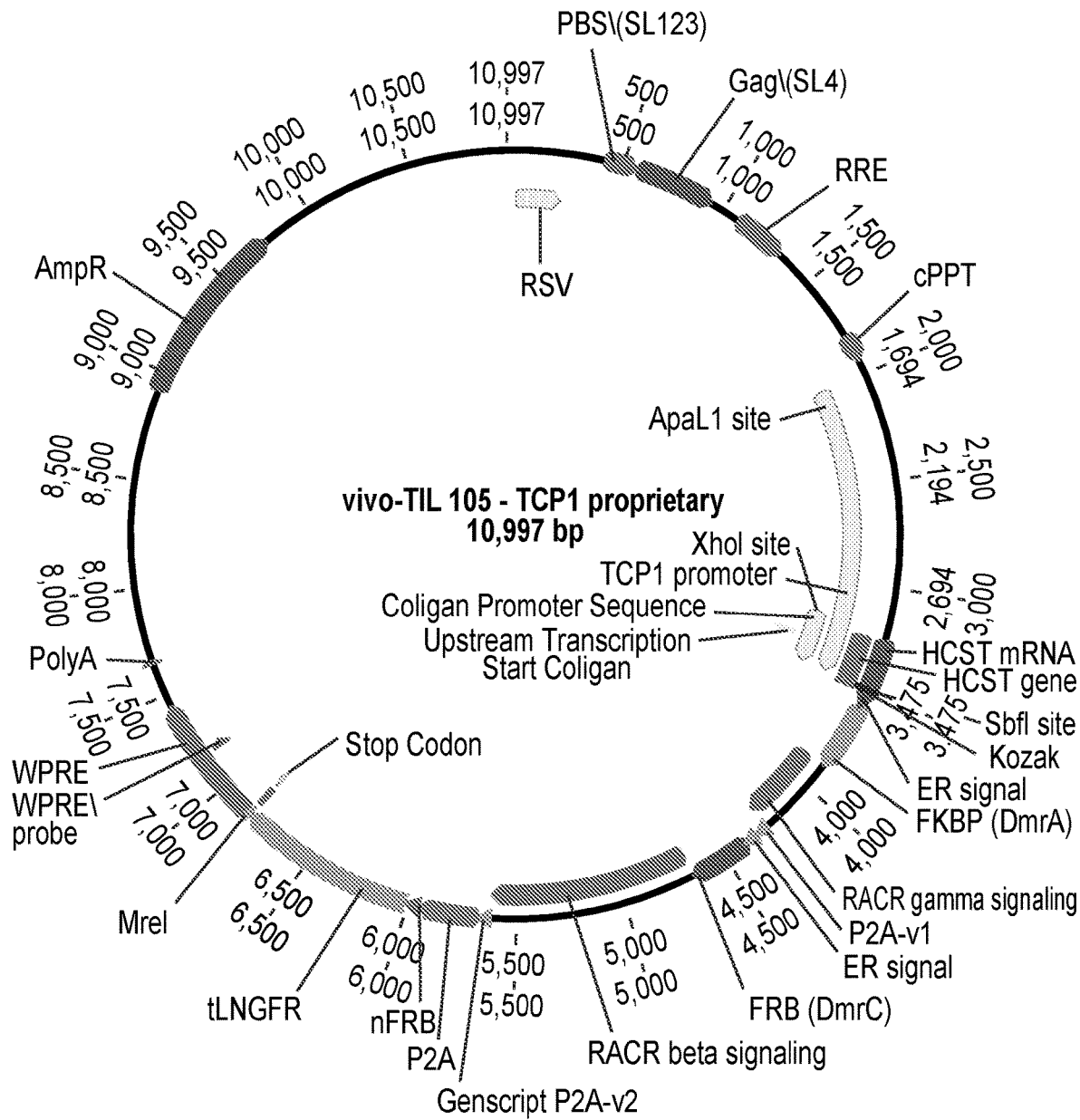
FIG. 7 depicts a vector map for vivo-TIL 105 TCP1 (SEQ ID NO: 7).
Figure 8:
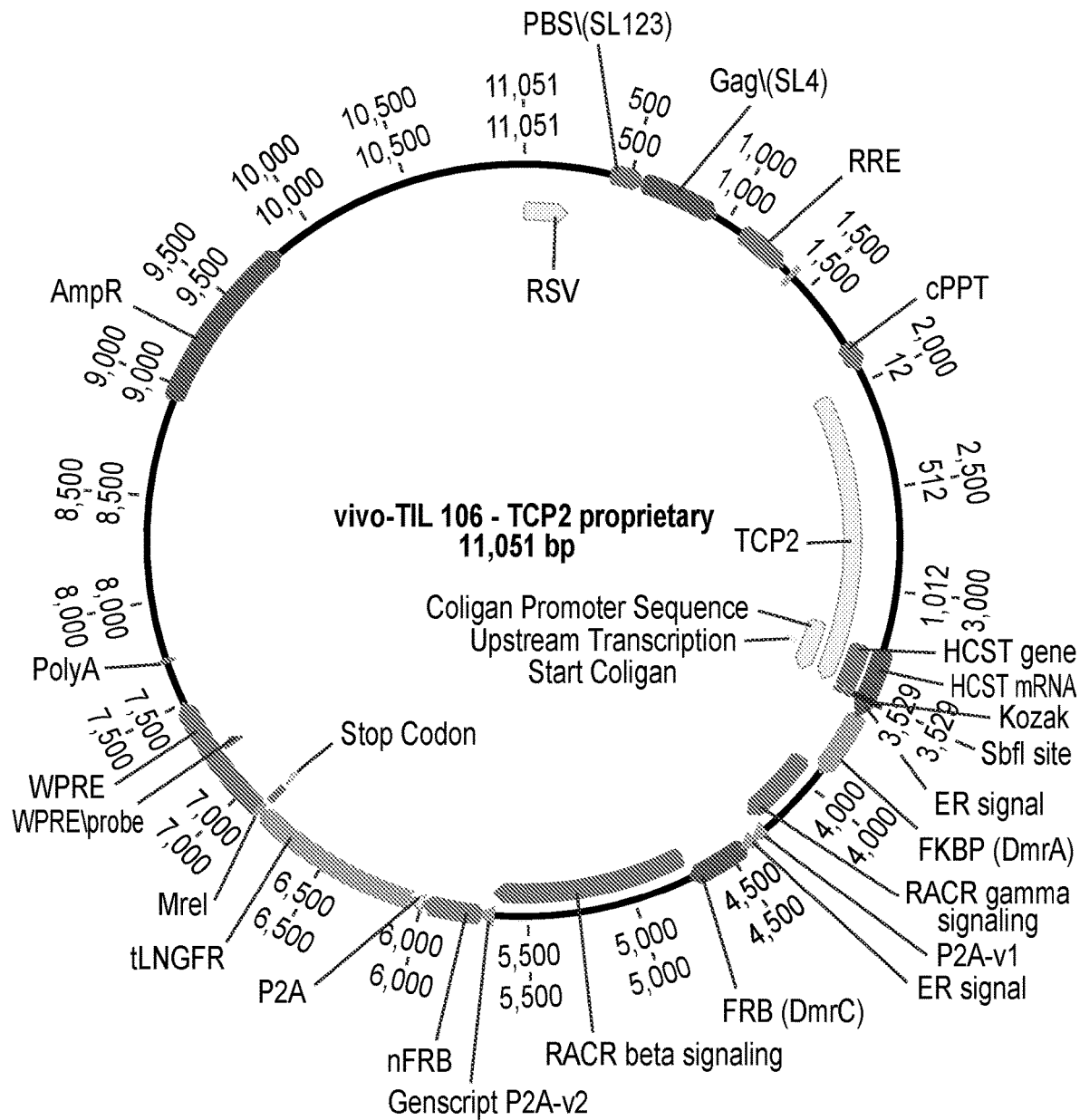
FIG. 8 depicts a vector map for vivo-TIL 106 TCP2 (SEQ ID NO: 8).
Figure 9:
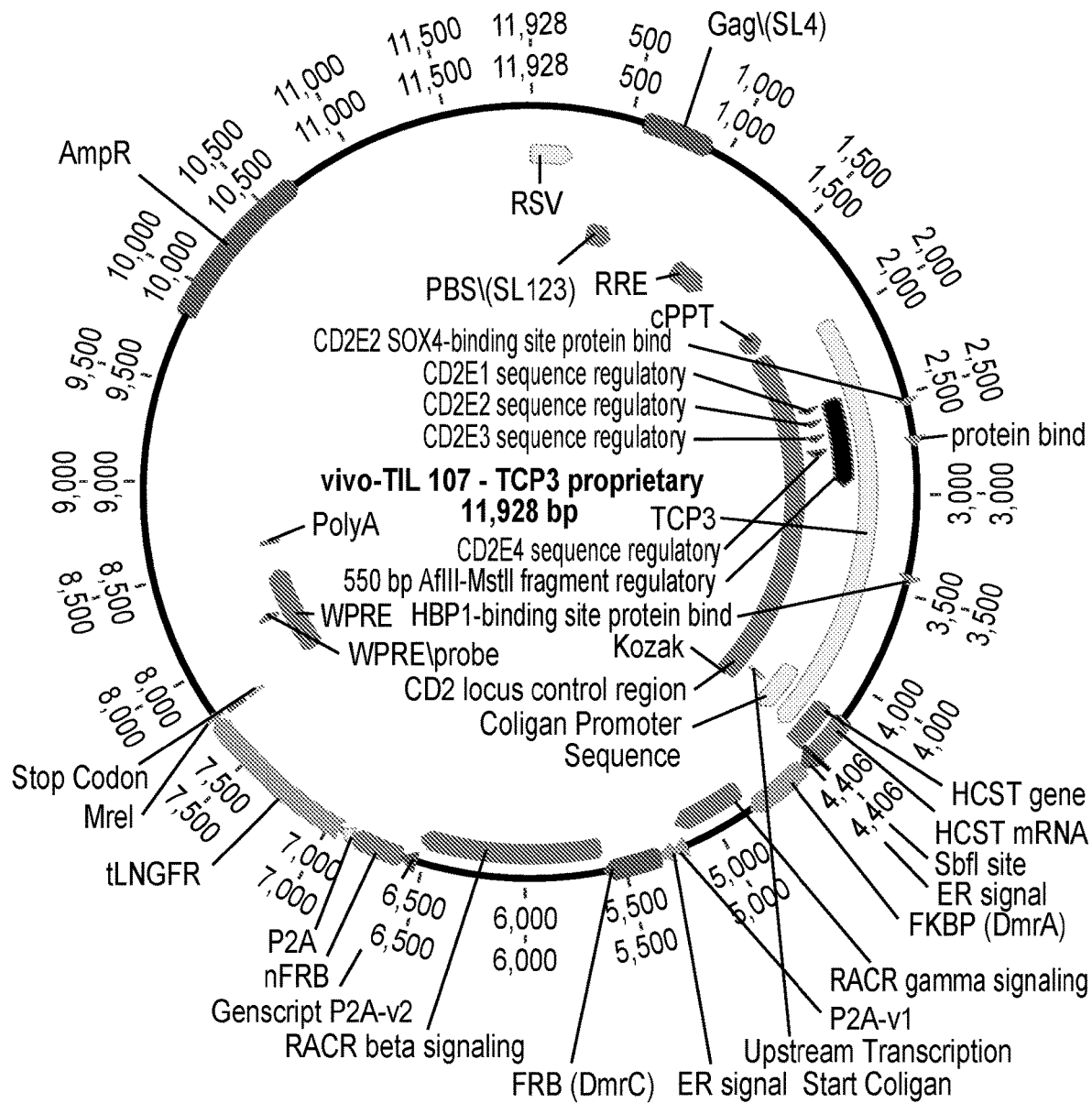
FIG. 9 depicts a vector map for vivo-TIL 107 TCP3 (SEQ ID NO: 9).
Figure 10:
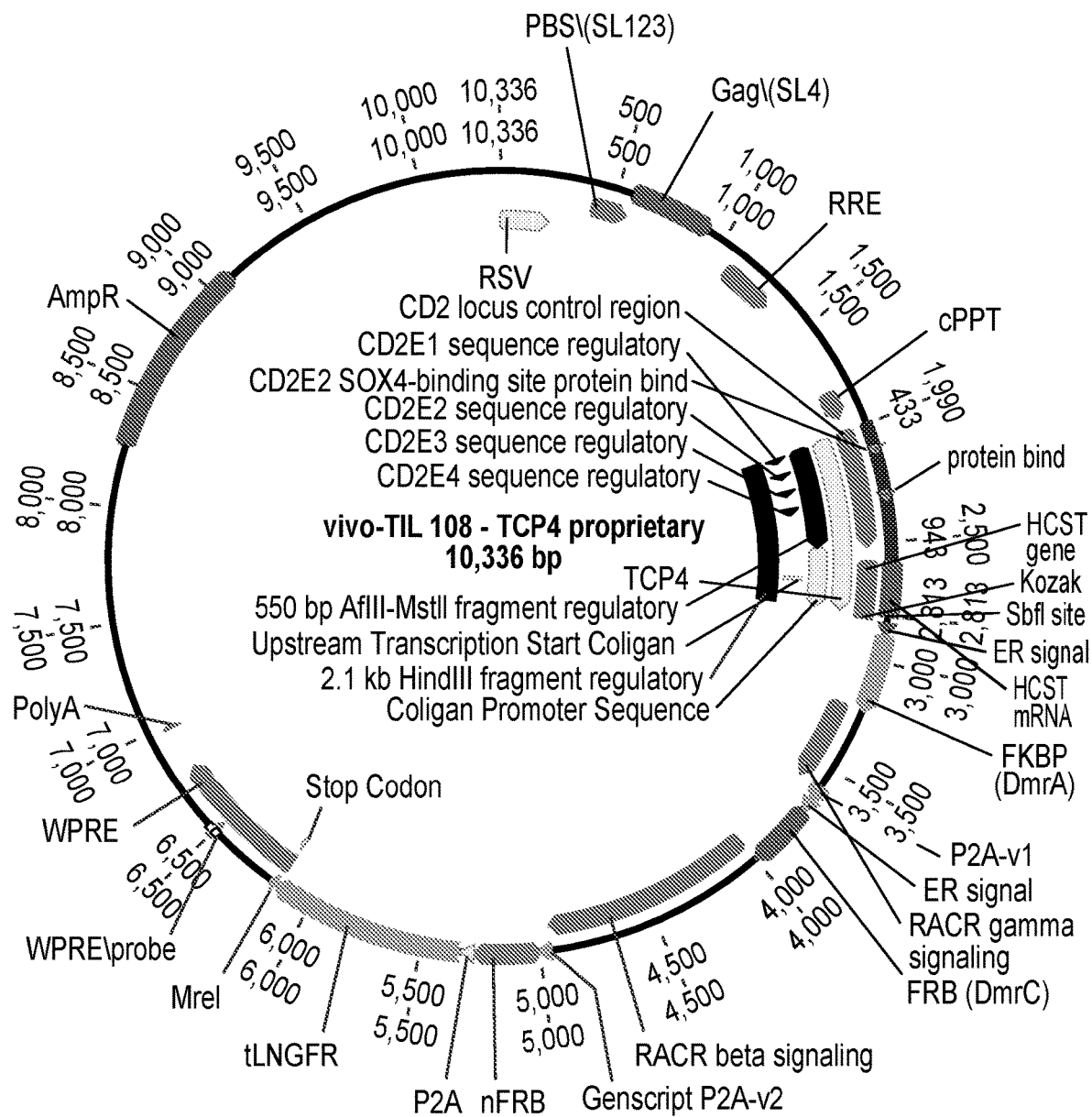
FIG. 10 depicts a vector map for vivo-TIL 108 TCP4 (SEQ ID NO: 10).
Figure 11:
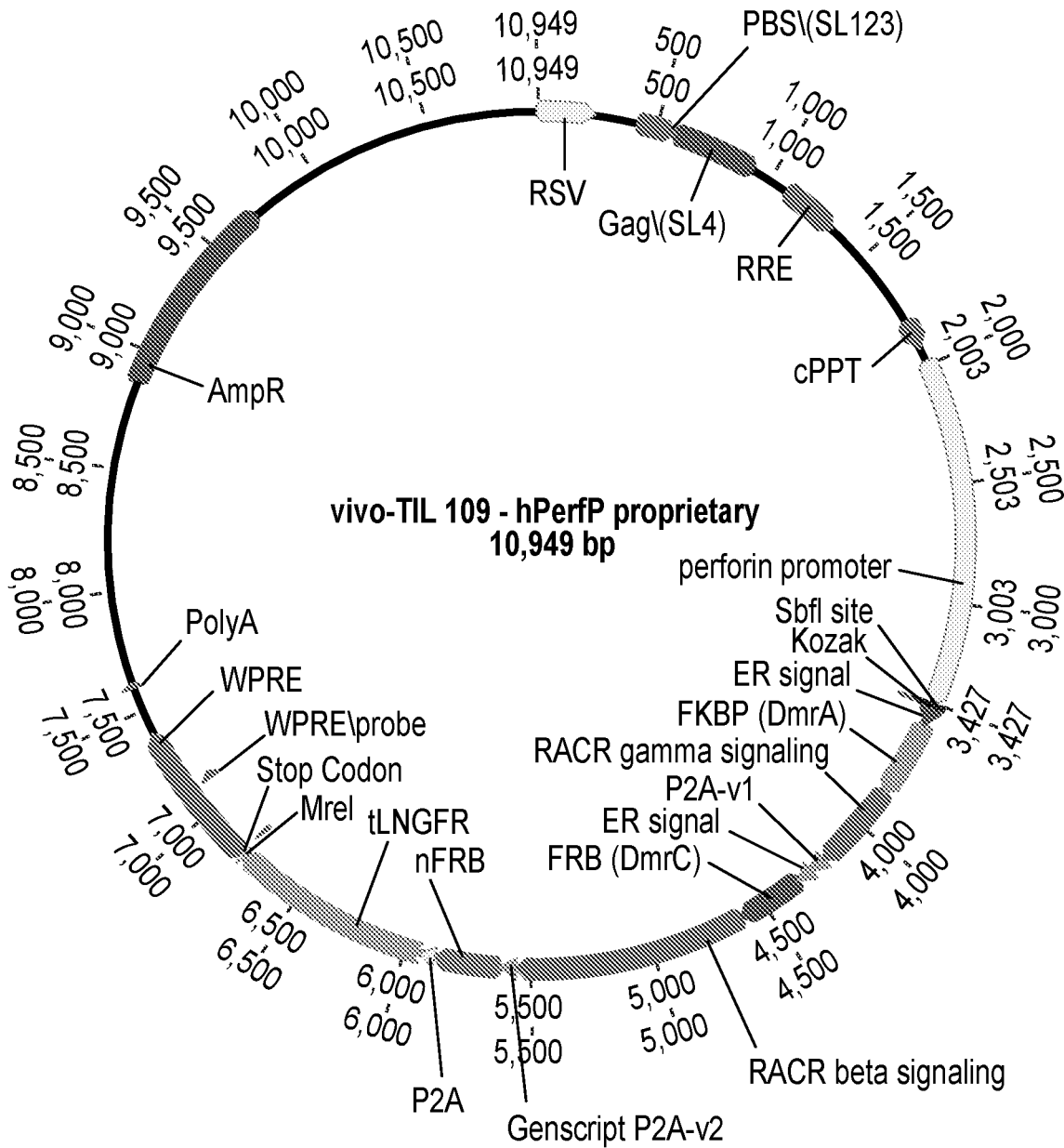
FIG. 11 depicts a vector map for vivo-TIL 109 hPerfP (SEQ ID NO: 11).

Human primary T cells (2.5×10$^5$ cells) were exposed to either HATSE particles or 293T particles, at MOI 5 or MOI 20, in duplicate, in the presence or absence of exogenous T-cell activation stimulus (Dynabeads™ Human T-Activator CD3/CD28—"stimbeads"). Growth of cells was evaluated over 7 days by an automated cell counter (Countess™ II, Thermo Fisher) (FIG. 3). Growth of cells exposed to HATSE particles was similar to bead-stimulated T cells transduced with control particles, and was roughly two times greater at 7 days than 293T control particles. GFP expression was evaluated by fluorescence microscopy (FIG. 4). Cells exposed to HATSE particles exhibit blasting and show high GFP expression similar to bead-stimulated T cells transduced with control particles, confirming efficient transduction of the HATSE-particle exposed T-cells, despite the lack of exposure to a heterologous T-cell activating stimulus (i.e., the stimulating beads).

Example 2

Lenti-RACCR

Figure 12A:
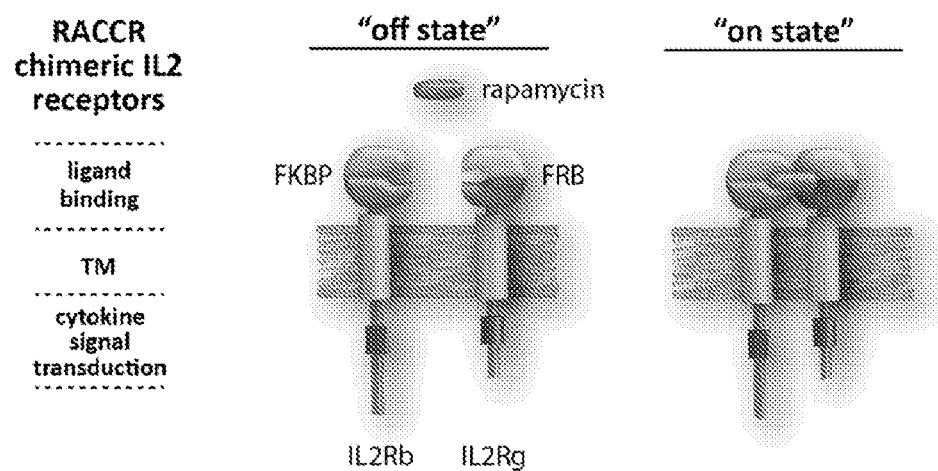
FIGS. 12A-12F show results for an exemplary small-molecule controllable T-cell/NK-cell activation receptor, termed RACCR.

Lenti-RACCR is a lentiviral vector that contains a transgene encoding a rapamycin-activated chimeric cell-surface receptor (RACCR). Specifically this exemplary RACCR is made from two fusion proteins that are designed to dimerize in the presence of rapamycin, thereby activating signalling (FIG. 12A). The first fusion protein is the result of fusing the cytoplasmic domain of the IL-2 receptor beta chain (IL2Rb) to FK506 binding protein (FKBP) so that FKBP forms the extracellular domain of the fusion protein. The second fusion protein is the result of fusing the cytoplasmic domain of IL-2 receptor gamma chain (IL2Rg) to the FKBP-rapamycin-binding (FRB) domain of mammalian target of rapamycin (mTOR) so that FRB forms the extracellular domain of the fusion protein. The extracellular domains are known to form a trimeric complex in the presence of rapamycin, resulting in dimerization of the receptor subunits to form an actively signaling receptor complex.

RACCR-beta—FKBP-IL2Rb fusion protein with signal peptide (in parenthesis) with 2A peptide (in italics):

```
                                           (SEQ ID NO: 12)
(MALPVTALLLPLALLLHAARP)ILWHEMWHEGLEEASRLYFGERNVKGMF

EVLEPLHAMMERGPQTLKETSFNQAYGRDLMEAQEWCRKYMKSGNVKDLLQ

AWDLYYHVFRRISKGKDTIPWLGHLLVGLSGAFGFIILVYLLINCRNTGPW

LKKVLKCNTPDPSKFFSQLSSEHGGDVQKWLSSPFPSSSFSPGGLAPEISP

LEVLERDKVTQLLLQQDKVPEPASLSSNHSLTSCFTNQGYFFFHLPDALEI

EACQVYFTYDPYSEEDPDEGVAGAPTGSSPQPLQPLSGEDDAYCTFPSRDD

LLLFSPSLLGGPSPPSTAPGGSGAGEERMPPSLQERVPRDWDPQPLGPPTP

GVPDLVDFQPPPELVLREAGEEVPDAGPREGVSFPWSRPPGQGEFRALNAR

LPLNTDAYLSLQELQGQDPTHLV GSGATNFSLLKQAGDVEENPG.
```

The FKBP domain has the following sequence:

```
                                           (SEQ ID NO: 13)
EMWHEGLEEASRLYFGERNVKGMFEVLEPLHAMMERGPQTLKETSFNQAYG

RDLMEAQEWCRKYMKSGNVKDLLQAWDLYYHVFRRISK.
```

The IL2Rb domain has the following sequence:

```
                                           (SEQ ID NO: 14)
GKDTIPWLGHLLVGLSGAFGFIILVYLLINCRNTGPWLKKVLKCNTPDPSK

FFSQLSSEHGGDVQKWLSSPFPSSSFSPGGLAPEISPLEVLERDKVTQLLL

QQDKVPEPASLSSNHSLTSCFTNQGYFFFHLPDALEIEACQVYFTYDPYSE
```

-continued

EDPDEGVAGAPTGSSPQPLQPLSGEDDAYCTFPSRDDLLLFSPSLLGGPSP

PSTAPGGSGAGEERMPPSLQERVPRDWDPQPLGPPTPGVPDLVDFQPPPEL

VLREAGEEVPDAGPREGVSFPWSRPPGQGEFRALNARLPLNTDAYLSLQEL

QGQDPTHLV.

RACCR-gamma—FRB-IL2Rg fusion protein with signal peptide (in parenthesis) with 2A peptide (in italics)

(SEQ ID NO: 15)
(MPLGLLWLGLALLGALHAQA)GVQVETISPGDGRTFPKRGQTCVVHYTGM

LEDGKKFDSSRDRNKPFKFMLGKQEVIRGWEEGVAQMSVGQRAKLTISPDY

AYGATGHPGIIPPHATLVFDVELLKLGEGSNTSKENPFLFALEAVVISVGS

MGLIISLLCVYFWLERTMPRIPTLKNLEDLVTEYHGNFSAWSGVSKGLAES

LQPDYSERLCLVSEIPPKGGALGEGPGASPCNQHSPYWAPPCYTLKPET*GS*

*GATNFSLLKQAGDVEENPG.*

The FRB domain has the following sequence:

(SEQ ID NO: 16)
GVQVETISPGDGRTFPKRGQTCVVHYTGMLEDGKKFDSSRDRNKPFKFMLG

KQEVIRGWEEGVAQMSVGQRAKLTISPDYAYGATGHPGIIPPHATLVFDVE

LLKLGE.

The IL2Rg domain has the following sequence:

(SEQ ID NO: 17)
GSNTSKENPFLFALEAVVISVGSMGLIISLLCVYFWLERTMPRIPTLKNLE

DLVTEYHGNFSAWSGVSKGLAESLQPDYSERLCLVSEIPPKGGALGEGPGA

SPCNQHSPYWAPPCYTLKPET.

Figure 12B:
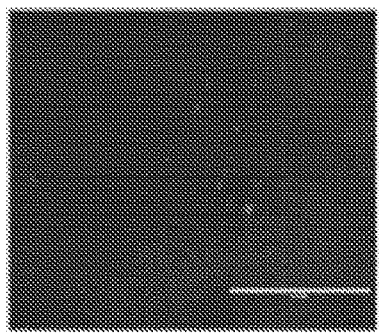

A lentiviral transfer plasmid encoding green fluorescence protein is packaged into lentiviral particles using the standard packaging plasmid pMD2.G, and the resulting lentiviral particles are used to transduce human primary T cells as a control experiment. Only low-level transduction is observed (FIG. 12B).

Figure 12C:
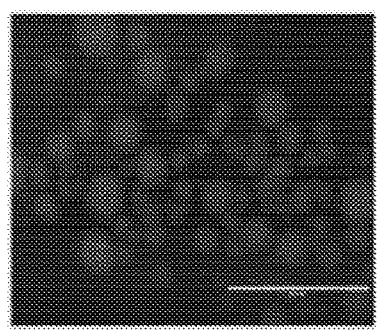

A lentiviral transfer plasmid encoding mCherry is packaged into lentiviral particles using a plasmid encoding T-cell activation and co-stimulatory molecules, thereby generating a surface-engineered lentiviral particle (SE-LVP). The resulting lentiviral particles (mCherry:SE-LVP) are used to transduce human primary T cells as a control experiment. High-level transduction is observed (FIG. 12C).

Figure 12D:
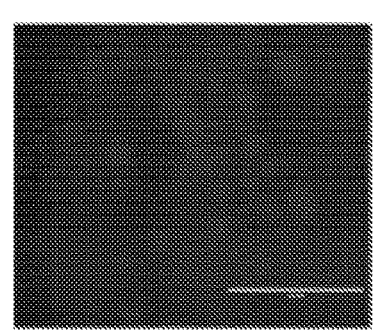

A lentiviral transfer plasmid encoding RACCR is packaged into lentiviral particles using a plasmid encoding T-cell activation and co-stimulatory molecules, thereby generating a surface-engineered lentiviral particle (SE-LVP). The resulting lentiviral particles (RACCR:SE-LVP) are used to transduce human primary T cells. High-level transduction is observed (FIG. 12D).

Figure 12E:
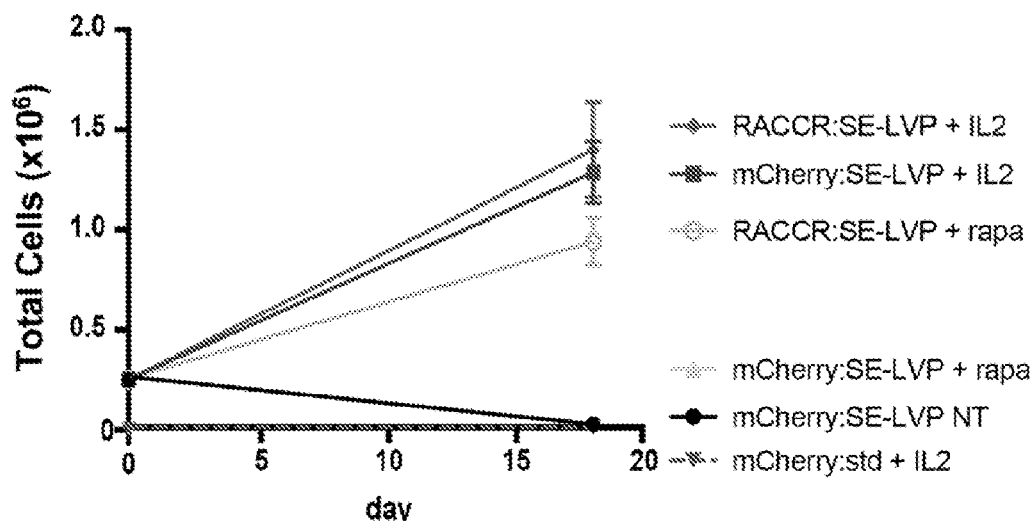
Figure 12F:
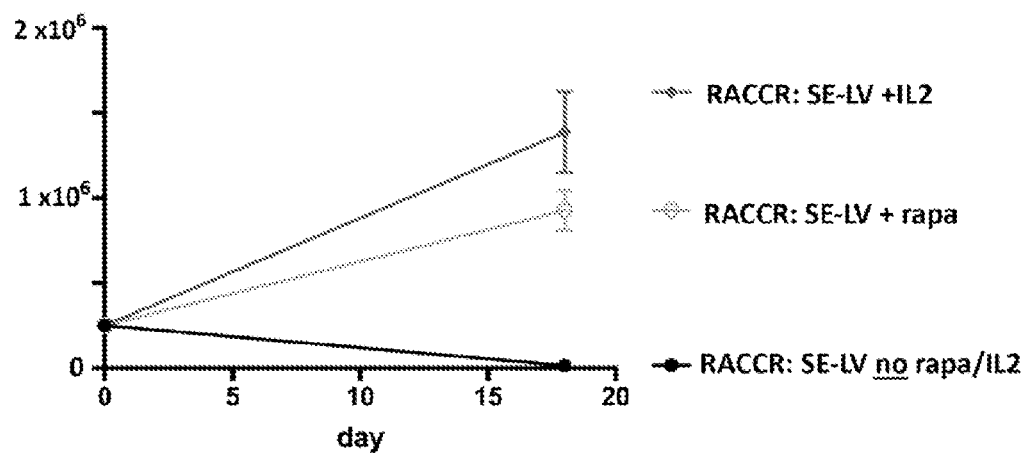

Human primary T-cell transduced with mCherry:SE-LVP or RACCR:SE-LVP are cultured in the presence of IL-2 ("IL2"), rapamycin ("rapa"), or no treatment ("NT"). As a control the mCherry contstruct packaged using the standard packaging plasmid pMD2.G is also tested with IL-2. RACCR:SE-LVP mediates sustained expansion of T-cell over 18 days in the presence of rapamycin but without exogenous IL-2 (FIG. 12E). T-cell expansion is dependent on the presence of rapamycin or IL-2 (FIG. 12F). This constitutes in vitro proof of concept that surface engineered particles can deliver a growth-stimulatory receptor payload and expand primary human T-cells. No spinoculation or other manipulations of the lentiviral particles is required for transduction. Transduction of cells at a multiplicity of infection (MOI) of 10 provided approximately 20% transduction efficiency.

Those skilled in the art will recognize, or be able to ascertain using no more than routine experimentation, many equivalents to the specific embodiments of the invention described herein. Such equivalents are intended to be encompassed by the following claims.

What is claimed:

1. A lentiviral particle for activating and efficiently transducing T cells, comprising a nucleic acid sequence encoding a small molecule controllable T-cell/NK-cell activation receptor, the nucleic acid sequence operatively linked to a promoter, wherein the T-cell/NK-cell activation receptor is capable of being activated by the small molecule;
wherein the T-cell/NK-cell activation receptor comprises two polypeptide chains that comprise extracellular domains that bind the small molecule, and wherein the two polypeptide chains each comprise a transmembrane domain and an intracellular cytokine receptor signaling domain; and
wherein the lentiviral particle further comprises a viral surface comprising an anti-CD3 antibody or scFv.

2. The lentiviral particle of claim 1, wherein the lentiviral particle is a surface-engineered lentiviral particle further comprising a T-cell activation or co-stimulation molecule.

3. The lentiviral particle of claim 2, wherein the T-cell activation or co-stimulation molecule comprises a 41bb ligand.

4. The lentiviral particle of claim 1, wherein the intracellular cytokine receptor signaling domain of a first polypeptide chain of the two polypeptide chains comprises a cytokine receptor signaling domain of a common cytokine receptor gamma chain.

5. The lentiviral particle of claim 4, wherein the intracellular cytokine receptor signaling domain of a second polypeptide chain of the two polypeptide chains comprises a cytokine receptor signaling domain of a common cytokine receptor beta chain.

6. The lentiviral particle of claim 1, wherein the extracellular domains of the T-cell/NK-cell activation receptor comprise a FK506 binding protein (FKBP) or a functional homolog thereof.

7. The lentiviral particle of claim 1, wherein the extracellular domains of the T-cell/NK-cell activation receptor comprise a FKBP12-rapamycin binding (FRB) protein or a functional homolog thereof.

8. The lentiviral particle of claim 1, wherein the lentiviral particle further comprises a nucleic acid sequence encoding a checkpoint-inhibiting ligand.

9. The lentiviral particle of claim 8, wherein the checkpoint-inhibiting ligand is capable of blocking the PD-1/PD-L1 checkpoint.

10. The lentiviral particle of claim 8, wherein the checkpoint-inhibiting ligand is capable of blocking the Tim-3 checkpoint.

11. The lentiviral particle of claim 1, further comprising a nucleic acid sequence encoding a protein that provides resistance to an immunosuppressive drug.

12. The lentiviral particle of claim 11, wherein the immunosuppressive drug is selected from the group consisting of methotrexate, rapamycin, a rapalog, tacrolimus, and cyclosporine.

13. The lentiviral particle of claim 1, further comprising a nucleic acid sequence encoding a TGFbeta dominant-negative inhibiting receptor.

14. The lentiviral particle of claim 1, wherein the sequence of the promoter is at least 95% identical to a sequence selected from the group consisting of SEQ ID NOs: 1-4.

15. A method for expanding T-cells capable of recognizing and killing tumor cells in a subject in need thereof, comprising:
   i) administering a lentiviral particle of claim 1 to the subject, and
   ii) administering the small molecule to the subject,
   wherein T-cells capable of recognizing and killing tumor cells in the subject are expanded.

16. The lentiviral particle of claim 1, wherein the viral surface of the lentiviral particle further comprises a CD28 ligand.

17. The lentiviral particle of claim 16, wherein the CD28 ligand is CD86.

18. The lentiviral particle of claim 1, wherein the viral surface of the lentiviral particle further comprises a CD28 ligand and a 41bb ligand.

19. The lentiviral particle of claim 1, wherein the sequence of the promoter is at least 95% identical to SEQ ID NO: 5.

20. The lentiviral particle of claim 1, wherein binding of the extracellular domains to the small molecule is sufficient for the intracellular cytokine receptor signaling domains of the two polypeptide chains to activate cytokine signal transduction.

21. The lentiviral particle of claim 1, wherein the T-cell/NK-cell activation receptor does not comprise an antigen binding domain.

22. The lentiviral particle of claim 1, wherein the small molecule comprises rapamycin, a rapalog, tacrolimus, coumermycin, gibberellin, abscisic acid, methotrexate, cyclosporin A, FKCsA, trimethoprim-synthetic ligand for FKBP, or a derivatives thereof.

* * * * *